United States Patent
Schaefer et al.

(10) Patent No.: US 9,901,935 B2
(45) Date of Patent: Feb. 27, 2018

(54) APPARATUS FOR PROCESSING BIOLOGICAL MATERIAL

(71) Applicant: QIAGEN GMBH, Hilden (DE)

(72) Inventors: Andreas Schaefer, Leverkusen-Schlebusch (DE); Thomas Voit, Hilden (DE); Walter Tschopp, Buetscheil (CH); Adrian Geiger, Zuzwil (CH); Markus Zbinden, Engelburg (CH); Harald Hibbing, Hamburg (DE); Andreas Karl, Seeburg (DE); Frank Eigemeier, Osterode-dorste (DE); Volker Behrmann, Langwedel-Nindorf (DE); Dietmar Kopp, Einbeck (DE); Andreas Schmiede, Wermelskirchen (DE)

(73) Assignee: QIAGEN GMBH, Hilden (DE)

(*) Notice: Subject to any disclaimer, the term of this patent is extended or adjusted under 35 U.S.C. 154(b) by 457 days.

(21) Appl. No.: 14/551,375

(22) Filed: Nov. 24, 2014

(65) Prior Publication Data

US 2015/0114123 A1    Apr. 30, 2015

Related U.S. Application Data

(62) Division of application No. 11/992,637, filed as application No. PCT/EP2006/066763 on Sep. 26, 2006, now Pat. No. 8,932,542.

(Continued)

(30) Foreign Application Priority Data

Sep. 26, 2005  (EP) .................................... 05020948
Jun. 14, 2006  (DE) ......................... 10-2006-027680

(51) Int. Cl.
*B04B 5/02*    (2006.01)
*B01L 9/06*    (2006.01)

(Continued)

(52) U.S. Cl.
CPC .... *B04B 5/02* (2013.01); *B01L 9/06* (2013.01); *B04B 5/0421* (2013.01); *B04B 7/08* (2013.01);
(Continued)

(58) Field of Classification Search
CPC .... G01V 8/10; G01S 15/04; G01N 2035/0436; G01N 2035/00801; G01N 35/0099;
(Continued)

(56) References Cited

U.S. PATENT DOCUMENTS 4,375,272 A    3/1983    Sutton, III
4,484,907 A    11/1984   Sheeran, Jr.
(Continued)

FOREIGN PATENT DOCUMENTS

DE    19926937 A1    1/2001
EP    0122772 A1    10/1984
(Continued)

OTHER PUBLICATIONS

International Search Report dated Jun. 22, 2007, issued in Application No. PCT/EP2006/066763.
(Continued)

*Primary Examiner* — Timothy Cleveland
(74) *Attorney, Agent, or Firm* — McBee Moore Woodward & Vanik IP, LLC; Susan McBee

(57) ABSTRACT

A gripper unit for handling a vessel for receiving biological material is proposed, inter alia. The vessel has a lid which can assume an open position and a closed position. The gripper unit comprises a gripper for gripping and releasing the vessel, and a lid holder, for holding a lid in a defined position in relation to the vessel. The defined position is an open position of the lid.

10 Claims, 24 Drawing Sheets

Related U.S. Application Data

(60) Provisional application No. 60/813,457, filed on Jun. 14, 2006.

(51) Int. Cl.

| | | |
|---|---|---|
| *G01N 35/00* | (2006.01) | |
| *B04B 5/04* | (2006.01) | |
| *B04B 13/00* | (2006.01) | |
| *B04B 7/08* | (2006.01) | |
| *B25J 11/00* | (2006.01) | |
| *G01S 15/04* | (2006.01) | |
| *G01V 8/10* | (2006.01) | |
| *B01L 3/00* | (2006.01) | |
| *B04B 11/04* | (2006.01) | |
| *G01N 35/04* | (2006.01) | |

(52) U.S. Cl.
CPC .............. *B04B 13/00* (2013.01); *B25J 11/00* (2013.01); *G01N 35/0099* (2013.01); *G01N 35/00712* (2013.01); *G01N 35/00732* (2013.01); *G01S 15/04* (2013.01); *G01V 8/10* (2013.01); *B01L 3/5021* (2013.01); *B01L 2300/043* (2013.01); *B04B 2011/046* (2013.01); *G01N 2035/00801* (2013.01); *G01N 2035/0436* (2013.01)

(58) Field of Classification Search
CPC ......... G01N 35/00732; G01N 35/00712; B25J 11/00; B04B 2011/046; B04B 13/00; B04B 7/08; B04B 5/0421; B04B 5/02; B01L 2300/043; B01L 9/06; B01L 3/5021

See application file for complete search history.

(56) References Cited

U.S. PATENT DOCUMENTS

| | | | |
|---|---|---|---|
| 4,735,776 A | 4/1988 | Yamamoto et al. | |
| 4,835,711 A * | 5/1989 | Hutchins ................ | B25J 9/1676 700/247 |
| 5,166,889 A | 11/1992 | Cloyd | |
| 5,472,669 A | 12/1995 | Miki et al. | |
| 5,700,429 A | 12/1997 | Buehler et al. | |
| 5,879,628 A | 3/1999 | Ridgeway et al. | |
| 6,060,022 A | 5/2000 | Pang et al. | |
| 6,277,648 B1 | 8/2001 | Coplan | |
| 6,426,044 B1 | 7/2002 | Cohen et al. | |
| 2002/0046967 A1 | 4/2002 | Romanauskas | |
| 2002/0121139 A1 | 9/2002 | Purpura et al. | |
| 2003/0103839 A1 | 6/2003 | Osborne et al. | |
| 2003/0148867 A1 | 8/2003 | Hayasaka | |
| 2003/0223916 A1 | 12/2003 | Testrut | |
| 2004/0002415 A1 | 1/2004 | Jang | |
| 2005/0158212 A1 | 7/2005 | Yavilevich | |
| 2006/0178093 A1 | 8/2006 | Hoffman | |
| 2007/0110624 A1 | 5/2007 | Lare et al. | |

FOREIGN PATENT DOCUMENTS

| | | |
|---|---|---|
| EP | 0557828 A1 | 9/1993 |
| EP | 0738541 A1 | 10/1996 |
| EP | 0979999 A2 | 2/2000 |
| EP | 1201297 A1 | 5/2002 |
| EP | 1237003 A2 | 9/2002 |
| EP | 1369179 A2 | 12/2003 |
| EP | 1659091 A1 | 5/2006 |
| EP | 1767274 A1 | 3/2007 |
| EP | 1862219 A1 | 12/2007 |
| GB | 2235639 A | 3/1991 |
| JP | H03226484 A | 10/1991 |
| WO | 9744670 A1 | 11/1997 |
| WO | 00/38046 A1 | 6/2000 |
| WO | 0224303 A | 3/2002 |
| WO | 03/040364 A1 | 5/2003 |
| WO | 03048025 A1 | 6/2003 |
| WO | 2005014226 A1 | 2/2005 |
| WO | 2005/019836 A2 | 3/2005 |
| WO | 2005/029094 A2 | 3/2005 |

OTHER PUBLICATIONS

QIAGEN, "The QIAGEN Guide to Template Purification and DNA Sequencing." 2nd Edition, 1998.
QIAGEN, "Bench Guide." 2001.
QIAGEN, "QIAprep Miniprep Handbook for Purification of Molecular Biology Grade DNA." 2nd Edition, 2005.
A. E. Fitzgerald et al.,"Electric Machinery: Torque Control." Sixth Edition, McGraw Hill, 2003, pp. 583-595.

* cited by examiner

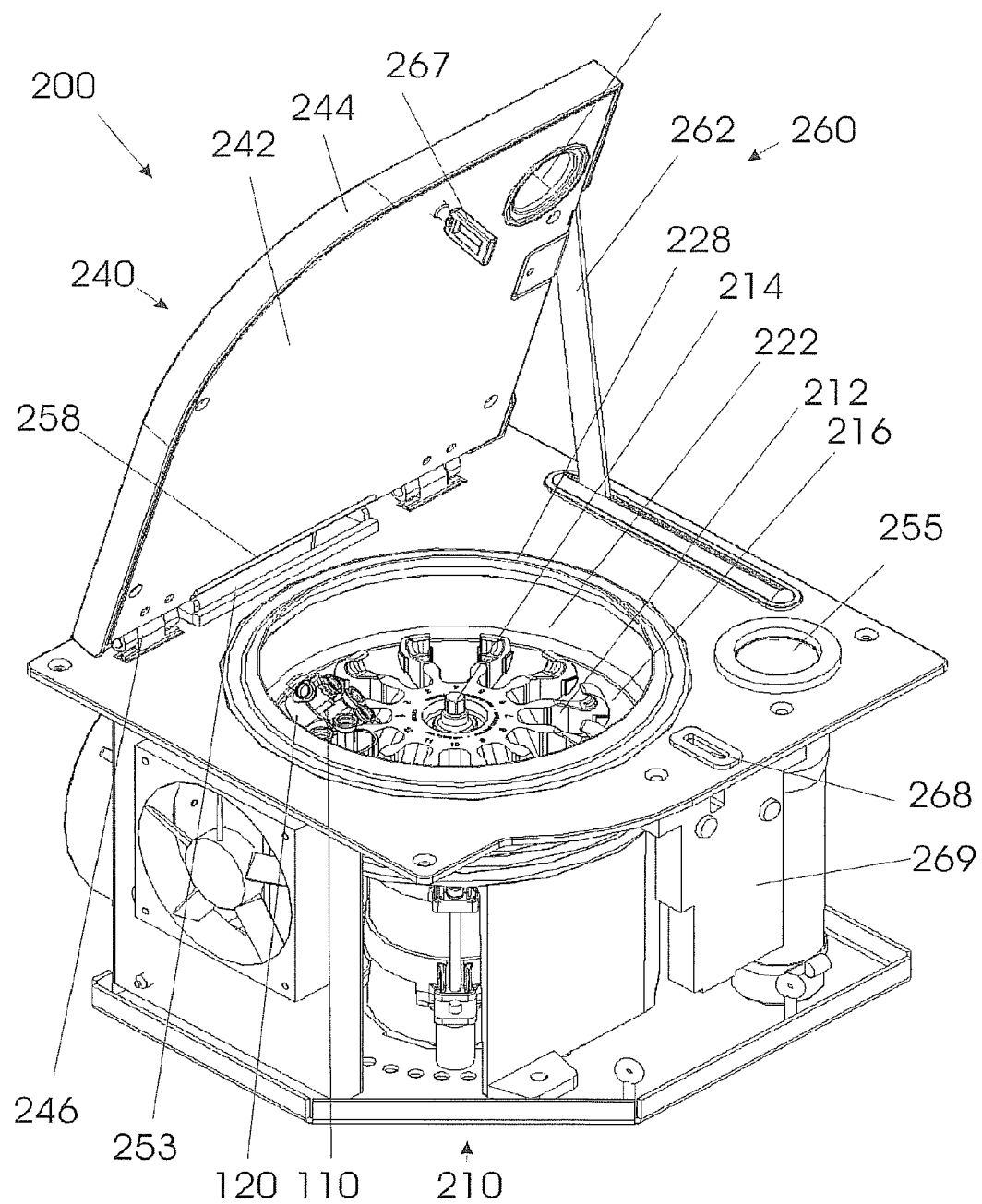

APPARATUS FOR PROCESSING BIOLOGICAL MATERIAL

This application is a divisional of pending U.S. application Ser. No. 11/992,637 filed Feb. 23, 2010, which is a United States national stage filing under 35 U.S.C. § 371 of international (PCT) application No. PCT/EP2006/066763, filed Sep. 26, 2006, and designating the US, which claims priority to European application 05020948.5, filed Sep. 26, 2005, German application no. 10 2006 0276809 filed Jun. 14, 2006, and U.S. Provisional Application 60/813,457 filed Jun. 14, 2006.

FIELD OF THE INVENTION

The present application relates to an apparatus for processing material, preferably biological material. It also relates to a centrifuge, particularly a centrifuge or an apparatus for centrifuging biological material and a process for centrifuging biological material in a centrifuge or for processing biological material in a centrifuge unit. It also relates to an apparatus for automatically processing biomolecules, particularly biomolecules from sample fluids.

The present application also relates to a gripper unit for handling a vessel, particularly a vessel for receiving biological material; to a gripper for gripping and/or releasing such a vessel; and to a vessel holder for such a vessel. It also relates to a process for gripping a vessel, particularly a vessel for receiving biological material, preferably using a gripper; and to a process for releasing such a vessel, preferably using a gripper.

The present application also relates to a process for transporting a vessel, preferably for transporting it into a vessel holder or out of a vessel holder. In particular, it relates to a process for removing the vessel from a vessel holder, particularly using a gripper unit, and preferably from a vessel holder in a centrifuge rotor, to an analogous process for placing the vessel in a vessel holder. It also relates to a process for transferring a vessel, particularly for transferring a vessel from a first vessel holder to a second vessel holder by means of a gripper unit or for transferring a vessel using a gripper from a first holding position of a vessel holder in a centrifuge rotor to a second holding position of a vessel holder in the centrifuge rotor.

The present application also relates to a process for positioning a centrifuge rotor of a centrifuge, particularly for positioning it at an angle of rotation about a rotation axis of the centrifuge rotor. It also relates to a process for positioning an angle of deflection of a vessel holder, particularly of a vessel holder for a vessel for receiving biological material.

The present application also relates to a process for cooling a centrifuge.

The present application also relates to a process for detecting the presence or absence of a vessel, particularly a vessel for receiving biological material, in a holder for the vessel. It also relates to a process for determining the height of a surface of a substance in a vessel, and to a process for detecting the nature of a vessel, particularly a vessel for receiving biological material, and most particularly for detecting the nature of a vessel in a container station for the vessel. It also relates to a process for checking the occupancy of a centrifuge and to a process for checking the occupancy of an apparatus for processing samples.

BACKGROUND OF THE INVENTION

In numerous technical fields such as chemistry, biology, medicine or environmental science, for example, it is necessary to analyse, process or react biological materials (e.g. fluids). For this purpose the fluids or materials are filtered, cooled, heated, broken down into their constituents, washed or pipetted by various methods or treated in other ways. It is frequently necessary to go through a long and complex sequence of processing steps in order to prepare the biological material. Moreover, in many cases, large collections of different materials have to be processed in accordance with the same sequence, or series of the same materials have to be processed in parallel. This can be time consuming, limits the throughput and is prone to breakdown.

The processing of biological materials is used for example in the field of the extraction and/or purification of biomolecules such as nucleic acids or proteins. For example, a well known method of purifying biomolecules is based on the steps of providing access to the contents of a biological sample ("lysis"), selectively binding the constituents of the contents of the biological sample to a solid support or carrier material ("binding"), eliminating unwanted ingredients from the solid support or carrier material ("washing"), and dissolving the desired constituent ("eluting").

In order to permit the desired absorption and desorption during the purification of the biomolecules, special filter elements have been developed which are formed from silica gel, for example, and which are porous or matrix-like on the one hand in order to allow a liquid to pass through the filter element and, on the other hand, have a surface to which the molecules bind in a specific or non specific process. In other purification processes, biomolecules are retained on filter elements simply by the effect of size exclusion. If a liquid which contains a biomolecule such as a nucleic acid, for example, passes through the filter element, the biomolecules or part thereof are retained in the filter element in any case, while the remainder passes through the filter element.

Moreover, in order to obtain the biomolecule from the filter element, an eluting liquid such as nuclease-free water is passed over the filter element in order to desorb the biomolecule. In this way the desired biomolecule is released from the filter element (eluted) and caught in a vessel. Such filter elements are frequently designed as membranes which are either arranged in individual vessels having an inlet opening and an outlet opening or are arranged in multiwell plates. The filter elements are processed either by centrifuging (spin format) or using apparatus based on vacuum technology. Individual vessels having an inlet opening and an outlet opening, which have a membrane and which can be used in a centrifuge, are also known in the form of columns, centrifuge columns, filter vessels, chromatography columns, columns, spin columns or single spin columns.

Generally, the advantages of the centrifuge process over the vacuum-based methods are the higher degree of purity, higher concentration and reduced risk of cross-contamination. In general, the best results for the purification of the biomolecules in terms of quality and concentration are obtained with the centrifuge columns (single spin tubes) which are processed under a high gravity field (>10,000×g), as this permits minimum cross contamination and maximum recovery of the desired substance from the membrane. One disadvantage, however, is the labour-intensive manual treatment of the centrifuge columns, which increases the risk of error and the processing time, especially when different samples have to be treated or processed simultaneously. A higher degree of standardisation and automation as well as a faster throughput can be achieved by using multiwell plate formats. However, this involves compromises with regard to quality and/or quantity.

QIAGEN offer a wide range of purification procedures and the necessary products for different biomolecules from a range of biological samples, based on the fundamental principle of the "bind-wash-elute" procedure. For this purpose, different filter materials and equipment are used as described for example in WO 03/040364 or U.S. Pat. No. 6,277,648. The commercially available product "QIAGEN QIAprep Spin Miniprep Kit" discloses for example a typical purification sequence and supplies standardised QIAprep columns and 2 ml collecting vessels for use in a centrifuge together with some reagents and buffers.

There are a number of publications on the subject of processing biological materials. U.S. Pat. No. 6,060,022, for example, discloses an automated system for sample processing which comprises an automated centrifuge apparatus. U.S. Pat. No. 5,166,889 describes a collecting system for blood in which a plurality of collecting vessels are positioned in a carrier wheel for direct access. US 2004/0002415 describes an automated centrifuge system for automatically centrifuging fluids which contain biological material such as e.g. nucleic acids in a general centrifuge. WO 2005/019836 describes an apparatus for processing fluid samples. WO 00/38046 describes an automated apparatus for loading a centrifuge, in which columns of the centrifuge are brought into play using an automated routing system. EP 122772 describes a chemical manipulator for use with reaction vessels. GB 2235639 describes a centrifuge with a protective jacket surrounding the rotating container.

One disadvantage of the existing automation system is that the processes which they support do not provide the high quality standard of the centrifuge columns and cannot function simultaneously with little or no manual intervention.

SUMMARY OF THE INVENTION

The present invention sets out to solve at least some of the problems outlined above.

Further advantages, features, aspects and details of the invention as well as preferred embodiments and particular aspects of the invention will become apparent from the subsidiary claims, the description and the drawings.

In one aspect of the invention a gripper unit for handling a vessel for receiving biological material is proposed. The vessel has a lid which can occupy an open position and a closed position. The gripper unit comprises a gripper for gripping and releasing the vessel, and a lid holder for holding a lid in a defined position in relation to the vessel. The defined position is an open position of the lid.

An apparatus for processing biological material is also proposed, this apparatus comprising the gripper unit and a centrifuge. The gripper of the gripper unit is suitable for placing the vessel in the centrifuge of removing it from the centrifuge.

A process for transporting a vessel into a vessel holder or out of a vessel holder is also proposed, the vessel comprising a lid attached thereto for closing off an opening of the vessel. The process comprises the steps of gripping or holding the vessel by means of a gripper unit; holding the lid in a defined position in relation to the vessel, and moving the vessel into the vessel holding or out of the vessel holder by means of the gripper unit, while maintaining the defined position of the lid relative to the vessel.

A process for removing a vessel from a vessel holder using a gripper unit is also proposed, the vessel comprising a lid attached thereto for closing off an opening of the vessel. The process comprises the steps of gripping the vessel by means of the gripper unit; holding the lid in a defined position in relation to the vessel, and removing the gripped vessel from the vessel holder using the gripper, while retaining the defined position of the lid relative to the vessel.

A process for setting a vessel in a vessel holder using a gripper unit is also proposed, the vessel comprising a lid attached thereto for closing off an opening of the vessel. The process comprises the steps of holding the vessel by means of a gripper unit; holding the lid in a defined position in relation to the vessel, and placing or inserting the held vessel into the vessel holder using the gripper, while retaining the defined position of the lid relative to the vessel. Optionally the process comprises the further step of releasing the vessel by the gripper.

A process is also proposed for transferring a vessel from a first holding position of a first vessel holder to a second holding position of a second vessel holder using a gripper unit, the vessel comprising a lid attached thereto for closing off an opening of the vessel. The process comprises the steps of gripping the vessel, which is in the first holding position, using the gripper unit; holding the lid in a defined position in relation to the vessel; removing the gripped vessel from the first vessel holder or the first holding position by means of the gripper; inserting the gripped vessel in the second vessel holder or in the second holding position using the gripper. In the steps of removal and insertion the defined position of the lid relative to the vessel is maintained. Optionally the process comprises the further step of releasing the vessel by the gripper.

A vessel holder for a vessel for receiving biological material is also proposed, having a lid attached thereto for closing off an opening of the vessel. The vessel holder is suitable for use in a centrifuge and comprises at least one holding member for holding vessel and at least one lid receptor for holding the lid attached to the vessel, which is shaped to allow access to the lid by a lid holder of a gripper unit for the vessel.

An apparatus for processing biological material is also proposed, comprising the vessel holder and centrifuge, the vessel holder being intended for use in the centrifuge.

An apparatus for processing biological material is also proposed, which comprises the following parts: a centrifuge with a rotatable centrifuge rotor having at least one vessel holder for holding a vessel for biological material, and a gripper for inserting a vessel in the vessel holder.

An apparatus for processing biological material is also proposed, which has the following parts: a centrifuge with a rotatable centrifuge rotor having at least one vessel holder for holding a vessel for biological material, and a gripper for removing a vessel from the vessel holder.

An apparatus for processing biological material is also proposed which comprises the following parts: a centrifuge with a rotatable centrifuge rotor having at least one vessel holder for holding a vessel for biological material, and a gripper for transferring a vessel from a first holding position of a vessel holder to a second holding position of a vessel holder.

A process for placing a vessel by means of a gripper in a vessel holder in a centrifuge rotor is also proposed, the vessel holder having a holding position for the vessel. The process comprises the following steps: the gripper is brought into position relative to the holding position; the gripper is moved in order to place the vessel in the holding position; the vessel is released by the gripper.

A process for removing a vessel using a gripper from a vessel holder in a centrifuge rotor is also proposed, the vessel holder having a holding position for the vessel. The process comprises the following steps: the gripper is brought into position in relation to the holding position; the vessel is gripped by the gripper; the gripper is moved in order to remove the vessel from the holding position.

A process for transferring the vessel by means of a gripper from a first holding position of a vessel holder in a centrifuge rotor to a second holding position of a vessel holder in the centrifuge rotor is also proposed. The process comprises the following steps: the gripper is brought into position in relation to the first holding position; the vessel is gripped by the gripper; the gripper is moved in order to remove the vessel from the first holding position; the gripper is brought into position in relation to the second holding position; the gripper is moved in order to place the vessel in the second holding position; the vessel is released by the gripper.

An apparatus for processing biological material is also proposed, comprising the following parts: a centrifuge rotor which is rotatable about a rotor axis, a drive for the centrifuge rotor, and a positioning element, which cannot co-rotate with the rotor, for positioning an angular position of the centrifuge rotor by interacting with a positioning counter-element co-rotatable with the rotor.

A process for positioning a centrifuge rotor of a centrifuge at an angular rotation about a rotation axis of the centrifuge rotor is also proposed. The process comprises the following steps: a positioning counter-element co-rotatable with the centrifuge rotor is brought into an operating range for interaction with a positioning element which does not co-rotate with the centrifuge rotor, and the centrifuge rotor is positioned by interaction of the positioning element with the positioning counter-element.

An apparatus for processing biological material is also proposed, comprising the following parts: a centrifuge rotor rotatable about a rotor axis, which is suitable for pivotally mounting a vessel holder for a vessel for receiving biological material, a first stop for the pivoting movement of the vessel holder, and a positioning element which is suitable for holding the vessel holder against the stop in an angle of deflection by interaction with a positioning counter-element of the vessel holder.

A process for positioning an angle of deflection of a vessel holder for a vessel for receiving biological material, which is pivotally mounted in a centrifuge rotor, is also proposed. The process comprises the following steps: a positioning element is brought into interaction with a positioning counter-element of the vessel holder; the vessel holder makes contact with a stop for the pivoting movement of the vessel holder, and the angle of deflection of the vessel holder is positioned at the stop by the interaction of the positioning element and positioning counter-element.

A vessel holder for a vessel for receiving biological material is also proposed. The vessel holder is suitable for use in a centrifuge and comprises a holding member for holding a vessel and a positioning counter-element which is shaped so as to engage with a positioning element. Thanks to this engagement it is possible to position an angular position and/or an angle of deflection of the vessel holder in the centrifuge. The actual stop is generally mounted on the centrifuge cup in which the vessel holder is inserted.

An apparatus for processing biological material is also proposed which comprises the following parts: a holder for a vessel for receiving biological material, the vessel having at least one vessel part of increased recognisability; a radiation source for irradiating a registration area in the holder, the registration area being associated with the vessel part having increased recognisability; a sensor for measuring the intensity of radiation coming from the registration area; and an evaluating unit which is designed to register the absence or presence of the vessel by comparing the intensity measured with a defined threshold value.

A process for detecting the presence or absence of a vessel for receiving biological material in a holder for the vessel is also proposed. The process comprises the following steps: a registration area in the holder is irradiated, the registration area being associated with a part of the vessel having increased recognisability; the intensity of radiation coming from the registration area is measured; the presence or absence of the vessel is registered by a comparison between the intensity measured and a defined threshold value.

An apparatus for processing biological material is also proposed, comprising the following parts: a vessel holder for receiving a vessel for the biological material; a sensor unit having an ultrasound source and an ultrasound sensor; and an evaluating unit for determining the state of opening of the vessel, as a function of sensor data of the ultrasound sensor, and for determining the possible presence of a substance in the vessel, as a function of sensor data of the ultrasound sensor and with the vessel open.

An apparatus for processing biological material is also proposed, comprising the following parts: a container station for holding a supply of vessels; a marking on the container station which contains information as to the nature of the vessels; and a radiation sensor for reading the marking.

A process for detecting the nature of a vessel for receiving biological material in a container station for the vessel is also proposed. The process comprises the following steps: a first marking on the container station which contains information as to the nature of the vessel is irradiated; and a first intensity of radiation coming from the first marking is measured; the nature of the vessel is registered as a function of the first intensity measured.

A process for checking the occupancy of a centrifuge is also proposed, comprising a plurality of vessel holding positions each intended for a vessel for biological material. The process comprises the following steps: for the vessel holding positions it registers whether a vessel is present therein; the total number of vessels registered as present in the vessel holding positions is stored; depending on the total number of vessels registered as present in the vessel holding positions, at least one condition for distributing the vessels in the vessel holding positions is determined; a check is made as to whether the distribution the vessels registered as present in the vessel holding positions complies with the condition.

The invention also relates to an apparatus for carrying out the processes disclosed and also comprises parts of apparatus for carrying out individual process steps. These process steps may be carried out by hardware components, by a computer programme using suitable software, by a combination of the two, or in any other manner. The invention is furthermore also directed to processes according to which the apparatus described above operate. It includes process steps for performing each function of the apparatus.

BRIEF DESCRIPTION OF THE DRAWINGS

Some embodiments exemplifying the invention are illustrated in the figures and described in more detail hereinafter. In the drawings:

FIGS. 3a-c show a perspective view of the centrifuge unit of an embodiment with the lid closed; with the lid open; with the lid flap of the lid removed;

FIG. 4 shows a lateral cross section through the centrifuge unit of FIG. 3a;

DETAILED DESCRIPTION OF THE INVENTION

Figure 1A:
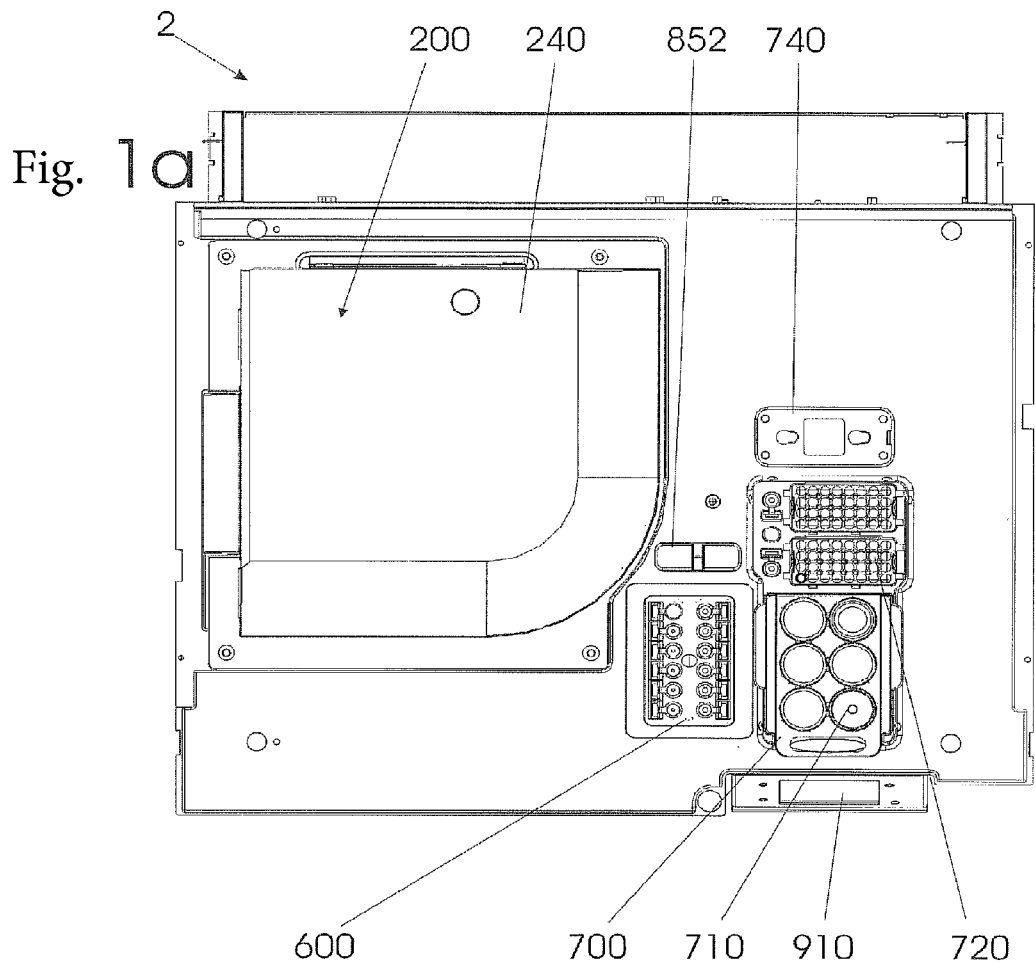
FIGS. 1a-c show a top view of the working plate with a pipette disposal station and without a gripper unit, an enlarged plan view of the pipette disposal station and a plan view of the working plate with gripper unit and with the centrifuge lid open in one embodiment.

The apparatus for processing biological materials described hereinafter permit or assist the efficient running of process or procedural steps for processing biological material. The apparatus preferably implement one or more of the following useful aspects.

One useful aspect is to run some of the process steps inside a centrifuge, and specifically not just the centrifuging of the material itself but also other steps which do not include any centrifuging. Carrying out such process steps in the centrifuge has the advantage that the apparatus of the centrifuge such as a holder for a vessel for the material can also be used efficiently for the other procedural steps. At the same time, in some cases, corresponding equipment outside the centrifuge can be dispensed with. At the same time the transfer of material in to and out of the centrifuge can be reduced. At the same time, travel distances can be shortened. As a result time can be saved and the risk of cross contamination can be minimised.

In order to carry out the procedural steps in the centrifuge it is also useful to remove material from a position in the centrifuge, introduce material into a position in the centrifuge or transfer it between different positions within the centrifuge. For this purpose there are two methods of transporting material available, inter alia:

First, if the material is liquid, it can be pipetted. For this purpose the apparatus may have a pipetting unit (c.f. for example FIG. 7). Secondly, a vessel containing the material may be transported. Such a vessel may be of any desired type. Preferably it is a column, e.g. a centrifuge column, i.e. single spin column, or a reaction or collecting vessel, e.g. an Eppendorf tube or similar vessel, i.e. a plastics vessel with our without a lid. In order to convert a vessel of this kind from a first position inside the centrifuge to a second position inside or outside the centrifuge, for example, the apparatus may have a movable gripper for the vessel.

These and similar processes for transporting material may be implemented even without the use of a centrifuge.

Some aspects of a gripper are proposed, independently of the embodiments shown. Thus, a gripper is proposed which is suitable for gripping and releasing a vessel for receiving biological material. Such a gripper comprises a gripping element which is movable in order to grip and release a vessel, a clamping element which is suitable for clamping the gripping element, a lifting element, and a drive for the lifting element, which is suitable for driving a lifting movement of the lifting element, so as to move the gripping element.

Optionally, the clamping element is suitable for clamping the gripping element in the direction of opening. As another option, the lifting movement of the lifting element moves the gripping element in the direction of closure. Alternatively, the clamping element is suitable for clamping the gripping element in the direction of closure. As a further option the lifting movement of the lifting element moves the gripping element in the direction of opening.

The clamping element is also optionally suitable for clamping the gripping element in order to release the vessel. As a further option the lifting movement of the lifting element moves the gripping element to grip the vessel. Alternatively, the clamping element is suitable for clamping the gripping element in order to grip the vessel. As a further option the lifting movement of the lifting element moves the gripping element in order to release the vessel.

Typically, the gripping element has an indentation which is suitable for engaging in a collar of the vessel. The gripping element is optionally a first gripping element, and the gripper then also has a second gripping element which has analogous properties to the first gripping element. It is also possible for the gripper to be pivotally mounted about a pivot axis. In this case, the gripping element typically defines a central axis for the vessel, and the pivot axis is different from the central axis.

A process for gripping a vessel for receiving biological material using a gripper is also proposed. The process comprises the following steps: generating a lifting movement of a lifting element; converting the lifting movement of the lifting element into a movement of the gripping element in the direction of closure or for gripping the vessel, the movement being directed counter to a force which a clamping element exerts on the gripping element; and gripping the vessel using the gripping element. Alternatively, the lifting movement of the lifting element can also be converted into a movement of the gripping element in the direction of opening in order to grip the vessel, for example if the gripper grips the vessel on a vessel surface directed towards the interior of the vessel.

A process for releasing a vessel for receiving biological material by means of a gripper is also proposed. This process comprises the following steps: generating a lifting movement of a lifting element, the lifting movement allowing movement of the gripping element in the direction of opening, producing a movement of the gripping element in the direction of opening in order to release the vessel by means of a clamping element, and releasing the vessel by means of the gripping element. Alternatively, the lifting movement of the lifting element may also allow movement of the gripping element in the direction of closure, and movement of the gripping element in the direction of closure in order to release the vessel may be generated by the clamping element.

A gripper unit for handling a vessel for receiving biological material is also proposed. The gripper unit comprises the following parts: a gripper member which is movable in a direction z, and a gripper for gripping the vessel, which is movable relative to the gripper member from a first position to a second position, and a drive for moving the gripper from the first position to the second position.

Optionally, the gripper unit is designed to insert the vessel in another vessel. Optionally, the drive is an electric drive. Optionally, the movement of the gripper from the first position to the second position takes place in a direction other than the direction z. Optionally, the movement of the gripper from the first position to the second position takes place in a direction which is perpendicular to the direction z. Optionally, the movement of the gripper from the first position to the second position is a pivoting movement about a pivot axis. Optionally, the pivot axis extends parallel to the direction z.

An apparatus for automatically processing biomolecules from sample material, preferably sample fluid, is also proposed, comprising the following elements: firstly a centrifuge which comprises a rotor for holding and rotating a plurality of containers, each of which contains at least one first opening for removably receiving and holding a filter vessel; and at least one second opening, for removably receiving and holding an additional, optionally sealed vessel; and at least one handling unit, comprising: means for removing said filter vessel from said first opening; means for combining said filter vessel with said additional vessel, so that the two vessels can rotate jointly with the centrifuge, and so that a liquid connection is provided between the volume of the filter vessel and the additional vessel.

The handling unit optionally contains means for bringing said filter vessel from said first opening on to said additional vessel which is attached to said second opening. The handling unit also optionally contains means for rotating said filter vessel or said additional vessel about a central line of the vessel, which is coaxial with said filter vessel or said sealed vessel. The means for removing said filter vessel from said first opening optionally include a first motor for separating said filter vessel from said sealed vessel in a coaxial direction. The means for placing said filter vessel on said additional vessel optionally include at least one second motor for bringing said filter vessel to said additional vessel.

A gripper unit for handling a vessel for holding biological material is also proposed. The vessel has a lid which can occupy an open position and a closed position. The gripper unit comprises a gripper for gripping and releasing the vessel, and a lid holder for holding a lid in a defined position in relation to the vessel. The defined position is an open position of the lid.

A system comprising the above mentioned gripper unit is also proposed. The system further comprises a centrifuge, and the gripper is suitable for inserting the vessel in the centrifuge or removing it from the centrifuge.

The vessel is optionally made of plastics. The lid is optionally attached to the vessel. Optionally, the gripper unit is movable in a direction z perpendicular to a plane of the working plate or in a direction x-y along a plane of the working plate. Optionally the vessel has a circular cross section, preferably a diameter of less than 2 cm, 1 cm. The lid is optionally suitable for closing off an opening of the vessel. The lid is optionally connected to the vessel via a connector. Optionally the gripper has a gripping element with a recess through which the connector of the lid can be passed when the vessel is gripped by the gripper. Optionally the lid holder comprises a mechanical stop for the lid. Optionally the lid is pressed against the mechanical stop by the connector. Optionally the gripping element is movable for gripping and releasing the vessel. Optionally the vessel holder is a device for processing liquids. Optionally the lid holder is configured so that when the gripping element picks up the vessel the lid holder is slid or guided along the lid. Optionally the handling comprises placing the vessel in a vessel holder, the vessel holder having a lid receptor; and the lid holder is then suitable for placing the lid in the lid receptor during the placing process. Optionally the handling includes removing the vessel from a vessel holder, the vessel holder having a lid receptor; and the lid holder is then capable of removing the lid from the lid receptor during the removal process. Optionally the lid receptor and the lid holder define the same position of the lid relative to the vessel.

A process for transporting a vessel into a vessel holder or out of a vessel holder is also proposed, the vessel comprising a lid attached thereto for closing off an opening of the vessel. The process comprises the steps of gripping or holding the vessel by means of a gripper unit; holding the lid in a defined position in relation to the vessel, and moving the vessel into the vessel holder or out of the vessel holder using the gripper unit, while retaining the defined position of the lid relative to the vessel.

The process for transporting a vessel is optionally a process for removing the vessel from a vessel holder using the gripper unit, while the step of moving the vessel into or out of the vessel holder is a removal of the vessel from the vessel holder by the gripper. Optionally, the step of removing the vessel from the vessel holder comprises removing the lid from a lid receptor of the vessel holder. Optionally, the vessel holder has a lid receptor for the lid of the vessel, and the step of removing the vessel from the vessel holder then comprises removing the lid from the lid receptor, while retaining the defined position of the lid relative to the vessel.

Optionally the process for transporting a vessel is a process for placing the vessel in a vessel holder using the gripper unit, while the step of moving the vessel into or out of the vessel holder comprises placing or inserting the vessel in the vessel holder. Optionally, the step of placing or inserting the vessel in the vessel holder comprises inserting the lid in a lid receptor of the vessel holder. Optionally, in the step of holding the lid the lid is held by a lid holder of the gripper unit in a defined position in relation to the vessel. Optionally, in order to place the vessel, the vessel is released by the gripper unit. The vessel optionally has a circular cross section, preferably a diameter of less than 2 cm or 1 cm.

Optionally, the vessel holder has a lid receptor for the lid of the vessel, and the step of inserting the vessel into the vessel holder then comprises inserting the lid into the lid receptor, while maintaining the defined position of the lid relative to the vessel.

A process for transferring a vessel from a first vessel holder to a second vessel holder using a gripper unit is also proposed, comprising the steps of removing the vessel from the first vessel holder or from a first holding position of the first vessel holder as described in the previous paragraphs, and inserting the vessel in the second vessel holder or in a second holding position of the second vessel holder as described in the previous paragraphs. In particular, the vessel is transferred from a first holding position of the first vessel holder to a second holding position of the second vessel holder. The first and the second holding positions are generally different. The first holding position and the second holding position may be in the same vessel holder or in different vessel holders.

A vessel holder for a vessel for receiving biological material with a lid attached thereto for closing off an opening of the vessel is also proposed. The vessel holder is suitable for use in a centrifuge and comprises at least one holding member for holding the vessel and at least one lid receptor for holding the lid attached to the vessel, which is shaped so as to allow access to the lid by a lid holder of a gripper unit for the vessel.

Optionally, the vessel holder or holders is or are mounted in a centrifuge. Optionally, the vessel holder or holders is or are pivotally mounted in the centrifuge, e.g. pivotally mounted in the centrifuge rotor. The lid is optionally open, i.e. in an open position of the lid.

An apparatus for processing biological material is also proposed, comprising the following parts: a vessel holder which is suitable for holding a vessel for receiving biological material with a lid attached thereto for closing off an opening of the vessel, and a lid holder or a gripper unit for the vessel, for holding the lid in a defined position in relation to the vessel, the vessel holder having a lid receptor for holding the lid attached to the vessel, which allows access by the lid holder to the lid. The apparatus further optionally comprises a centrifuge, the vessel holder being suitable for use in the centrifuge.

In the vessel holder or in the apparatus described in the two paragraphs immediately preceding this one, the access of the lid holder to the lid optionally includes mechanical contacting of the lid by the lid holder. A recess in the lid receptor optionally allows access by the lid holder to the lid. The apparatus is optionally designed so that access by the lid holder to the lid is obtained when the vessel is gripped by a gripper of the apparatus.

The vessel is optionally made of plastics. The lid is optionally attached to the vessel. The vessel is optionally circular in cross section and preferably has a diameter of less than 2 cm, 1 cm. The lid is optionally suitable for closing off an opening of the vessel.

An apparatus for processing biological material is also proposed, comprising the following parts: a centrifuge with a rotatable centrifuge rotor having at least one vessel holder for holding a vessel for biological material, and a gripper for inserting a vessel in the vessel holder.

An apparatus for processing biological material is also proposed, comprising the following parts: a centrifuge having a rotatable centrifuge rotor with at least one vessel holder for holding a vessel for biological material, and a gripper for removing a vessel from the vessel holder.

An apparatus for processing biological material is also proposed, comprising the following parts: a centrifuge with a rotatable centrifuge rotor having at least one vessel holder for holding a vessel for biological material, and a gripper for transferring a vessel from a first holding position of a vessel holder to a second holding position of a vessel holder. Optionally the first and second holding positions are different. The first and second holding positions may be in the same vessel holder or in different vessel holders.

In these apparatus the gripper is optionally designed to grip the vessel by engaging with a protruding vessel part. The gripper is optional for a vessel with an opening or main opening and a protruding vessel part, and the gripper is then designed to grip the vessel on a side of the protruding vessel part which is remote from the opening of the vessel. Optionally the gripping element comprises an indentation which is suitable for engaging in a collar of the vessel, and which is preferably suitable for engaging in a side of the collar remote from an opening of the vessel. The vessel is optionally for receiving biological material. The vessel holder is optionally pivotally mounted in the centrifuge rotor. The gripper optionally comprises a positioning element for positioning an angular position or a deflected position of the vessel holder. Optionally the positioning is carried out by interaction of the positioning element with a positioning counter-element. The positioning element for positioning a deflected position is optionally designed to co-operate with a stop for the vessel holder, for example with a stop which is co-rotatable with the centrifuge rotor. Optionally comprises the gripper the following parts: a gripping element which is movable for gripping and releasing a vessel, a clamping element which is suitable for clamping the gripping element, a lifting element, and a drive for the lifting element, which is suitable for driving a lifting movement of the lifting element, thereby moving the gripping element. The transferring optionally comprises a rotary movement of the vessel. The vessel holder is optionally removable from the centrifuge.

The clamping element is optionally suitable for clamping the gripping element in the direction of opening. The lifting movement of the lifting element optionally moves the gripping element in the direction of closure. The clamping element is optionally suitable for clamping the gripping element in the direction of closure. The lifting movement of the lifting element optionally moves the gripping element in the direction of opening. The clamping element is optionally capable of clamping the gripping element so as to release the vessel. The lifting movement of the lifting element optionally moves the gripping element so as to grip the vessel. The clamping element is optionally capable of clamping the gripping element so as to grip the vessel. The lifting movement of the lifting element optionally moves the gripping element so as to release the vessel.

The vessel holder is optionally movably mounted in the centrifuge rotor. In this case the positioning means are optionally capable of preventing or restricting a movement of the vessel holder during the insertion/removal/transfer. Optionally the transferring is carried out directly, i.e. the gripper holds the vessel throughout the entire period between the removal from the first holding position and insertion in the second holding position. During the transfer there is optionally also a third holding position, and the apparatus can then also additionally transfer the vessel between the third holding position and the first or second holding position. The gripping element optionally comprises at least one indentation, which is suitable for engaging in a collar of the vessel. The gripping element is optionally a first gripping element, and the gripper also comprises a second gripping element, which has analogous properties to the first gripping element. The gripper is optionally pivotally mounted about a pivot axis. The gripping element optionally defines a central axis for the vessel, and the pivot axis is then different from the central axis.

A process for placing a vessel by means of a gripper into a vessel holder in a centrifuge rotor is also proposed, wherein the vessel holder has a holding position for the vessel. The process comprises the following steps: the gripper is brought into position in relation to the holding position; the gripper is moved to place the vessel into the holding position; the vessel is released by the gripper.

A process for removing a vessel by means of a gripper from a vessel holder in a centrifuge rotor is also proposed, wherein the vessel holder has a holding position for the vessel. The process comprises the following steps: the gripper is brought into position in relation to the holding position; the vessel is gripped by the gripper; the gripper is moved, in order to remove the vessel from the holding position.

A process for transferring a vessel by means of a gripper from a first holding position of a vessel holder in a centrifuge rotor to a second holding position of a vessel holder in the centrifuge rotor is also proposed. The process comprises the following steps: the gripper is brought into position in relation to the first holding position; the vessel is gripped by the gripper; the gripper is moved, in order to remove the vessel from the first holding position; the gripper is brought into position in relation to the second holding position; the gripper is moved, in order to place the vessel in the second holding position; the vessel is released by the gripper.

Optionally the processes described above include the step of adjusting a predetermined angle of rotation of the vessel holder about the rotation axis of the centrifuge rotor. During the removal and/or during the insertion the gripper and a gripper member are optionally moved jointly in a direction z, and during the positioning of the vessel in relation to the second holding position the gripper is optionally moved relative to the gripper member. Moreover the processes optionally include the step of fixing the angular position or a deflection angle. For example the deflection angle of the vessel holder can be fixed by causing a positioning element of the gripper to interact with a positioning counter-element of the vessel holder; the vessel holder makes contact with a stop for the pivoting movement of the vessel holder, and the deflection angle of the vessel holder is fixed by the interaction of the positioning element and positioning counter-element at the stop. The stop for the pivoting movement of the vessel holder is optionally co-rotatable with the centrifuge rotor. The holding position is optionally in a vessel holder that is removable from the centrifuge.

The step of gripping the vessel optionally comprises the following partial steps: producing a lifting movement of a lifting element; converting the lifting movement of the lifting element into a movement of the gripping element, in the direction of closure or in the direction of opening, so as to grip the vessel, wherein the movement is directed counter to a force which a clamping element exerts on the gripping element; and hence gripping the vessel by means of the gripping element.

The step of releasing the vessel optionally comprises the following partial steps: producing a lifting movement of a lifting element, wherein the lifting movement allows a movement of the gripping element in the direction of opening, producing a movement of the gripping element in the direction of opening or in the direction of closure so as to release the vessel by means of a clamping element, and thus releasing the vessel by means of the gripping element.

The step of gripping the vessel optionally comprises gripping the vessel on a side of a protruding part of the vessel that is remote from an opening or a main opening of the vessel.

During the positioning of the vessel in relation to the second holding position the gripper is optionally moved relative to the gripper member in a direction which is different from the direction z. During the positioning of the vessel in relation to the second holding position the gripper is optionally moved relative to the gripper member in a plane which extends perpendicularly to the direction z. During the positioning of the vessel in relation to the second holding position the gripper is optionally pivoted relative to the gripper member about an axis that extends parallel to the direction z. Optionally the first and second holding positions are different. They may be in the same vessel holder or in different vessel holders. The gripper optionally engages in a protruding part of the vessel.

For the processes mentioned hereinbefore for transporting material it is useful to fix and/or position the centrifuge and a vessel holder mounted therein so as to enable a controlled transfer of fluids and prevent undesirable movements e.g. during the automated transfer of vessels in the centrifuge. Such movements may be, inter alia, rotation of the centrifuge rotor about its rotor axis or pivoting of a vessel holder in the centrifuge rotor about its pivot axis.

An apparatus for processing biological material is therefore proposed which has the following parts: a centrifuge rotor rotatable about a rotor axis, a drive for the centrifuge rotor, and a positioning element which is not co-rotatable with the rotor for positioning an angular position of the centrifuge rotor by interaction with a positioning counter-element which is co-rotatable with the rotor.

The positioning of the angular position is optionally carried out by mechanical engagement between positioning element and positioning counter-element. The centrifuge rotor is optionally suitable for receiving a vessel holder for a vessel for receiving biological material. The positioning counter-element is optionally mounted on the vessel holder or on the centrifuge rotor. Optionally the apparatus contains means for detecting an angular position of the centrifuge or of the centrifuge rotor. The positioning element can then be aligned as a function of the angular position detected such that the positioning element is located in an operating range of the positioning counter-element. The positioning element is optionally also suitable for positioning a deflection angle of the vessel holder, as will be explained hereinafter. The centrifuge rotor is optionally suitable for the pivotal mounting of a vessel holder for a vessel for receiving biological material and has a stop for the pivoting movement of the vessel holder. The positioning element is then capable of holding the vessel holder at a deflection angle at the stop by interaction with the positioning counter-element.

The positioning element may be attached to a gripper member of a gripper unit for gripping the vessel. Alternatively it may also be attached to a pipetting unit, for example. The positioning optionally allows the angular position to be adjusted to an accuracy of 0.1°. The apparatus optionally also comprises means for roughly positioning the centrifuge rotor which allow the angular position to be adjusted with an accuracy of 1.5°. The apparatus further optionally comprises means for detecting the angular position of the centrifuge rotor, for example means which allow the angular position of the centrifuge rotor to be detected with an accuracy of 1°. The drive is optionally an electric drive, preferably an induction motor, i.e. an Asynchronous motor. The positioning element optionally comprises a spike and the positioning counter element then comprises a recess for the spike. The positioning element is optionally attached to the gripper member in such a way that positioning is possible with the gripper obtaining access to a vessel holding position of the vessel holder. The positioning element is optionally resiliently mounted on the gripper member in the direction z. The spring mounting optionally allows travel of the positioning element which is greater than the length of the vessel. The vessel optionally has a circular cross section and is preferably made of plastics. The positioning element is optionally arranged in a fixed angular relation to a holding position of the vessel holder. The apparatus optionally comprises a plurality of positioning counter elements, preferably more than 3, more than 6 or more than 10 positioning counter elements.

A process for positioning a centrifuge rotor of a centrifuge at an angle of rotation about a rotation axis of the centrifuge rotor is also proposed. The process comprises the following steps: a positioning counter element which is co-rotatable with the centrifuge rotor is brought into an operating range for interaction with a positioning element that does not co-rotate with the centrifuge rotor, and the centrifuge rotor is positioned by interaction of the positioning element with the positioning counter element.

The positioning counter element is optionally moved into the operating range for interaction with the positioning element and by selecting an angular position of the centrifuge rotor about its rotation axis at an angular interval such that the positioning counter element is in the operating range.

The positioning counter element is optionally brought into the operating range for interaction with the positioning element by the following steps: an angular position of the centrifuge rotor about its rotation axis is detected and the positioning element is aligned, as a function of the angular position detected, such that the positioning element is located in the operating range.

By the positioning of the centrifuge rotor an angle of rotation of a holding position for a vessel in the centrifuge rotor about a rotor axis of the centrifuge rotor is optionally determined. The interaction is optionally a mechanical engagement or a magnetic interaction. By the positioning an angle of rotation of the centrifuge rotor about its rotor axis is optionally determined. Together with the positioning of the angle of rotation of the vessel holder in the centrifuge a deflection angle of the vessel holder is optionally positioned or fixed.

An apparatus for processing biological material is also proposed, comprising the following parts: a centrifuge rotor which is rotatable about a rotor axis, and which is suitable for the pivotable mounting of a vessel holder for a vessel for receiving biological material, a first stop for the pivoting movement of the vessel holder, and a positioning element which is suitable for holding the vessel holder at an angle of deflection against the stop by interaction with a positioning counter element of the vessel holder.

The pivoting movement of the vessel holder may generally also be designated as an oscillating movement or movement of deflection, as this movement generally defines the deflection angle.

The positioning is optionally carried out by means of the positioning element for angular positioning as described hereinbefore. The centrifuge rotor optionally also comprises a second stop for a pivoting movement which is caused by a centrifugal force of the centrifuge rotor. The first and/or second stop is optionally mounted on the centrifuge rotor or capable of rotating therewith. The positioning is optionally achieved by pressing the vessel holder against the stop. The stop optionally restricts a pivoting movement of the vessel holder which is opposed to a reference pivoting movement caused by a centrifugal force of the centrifuge rotor. The pivoting movement optionally takes place about a substantially horizontal axis.

An apparatus for processing biological material is also proposed which comprises the following elements: a centrifuge rotor rotatable about a rotor axis, which is suitable for pivotally mounting a vessel holder for a vessel for receiving biological material, the vessel holder comprising a positioning counter element, a stop for the pivoting movement of the vessel holder, and a positioning element which is suitable for bringing the vessel holder into contact with the stop by interaction with a positioning counter element, the angle of deflection of the vessel holder being positioned or fixed by the contact.

A process for positioning an angle of deflection of a vessel holder for a vessel for receiving biological material is also proposed, which is pivotally mounted in a centrifuge rotor. The process comprises the following steps: a positioning element is brought into interaction with a positioning counter element of the vessel holder; the vessel holder makes contact with a stop for the pivoting movement of the vessel holder, and the deflection angle of the vessel holder is positioned by the interaction of the positioning element and positioning counter element at the stop. The deflection angle may also be referred to as the pivotal position.

The positioning is optionally carried out using the positioning element for angular positioning as described above. The positioning is optionally carried out by pressing the vessel holder against a stop which is mounted on the centrifuge rotor.

A vessel holder for a vessel for receiving biological material is also proposed. The vessel holder is suitable for use is a centrifuge and comprises a holding part for holding a vessel, and a positioning counter element which is shaped so as to engage with a positioning element. This engagement allows the angular position and/or a deflection angle of the vessel holder in the centrifuge to be positioned.

The vessel holder optionally further comprises a connecting member which is suitable for connecting the vessel holder to the centrifuge. The connecting member optionally defines a pivot axis. The distance between the positioning counter element and a centre of the vessel holder is optionally greater than the distance between the positioning counter element and an edge of the vessel holder. The positioning counter element optionally comprises a cavity for accommodating the positioning element. The engagement between the positioning counter element and the positioning element is optionally suitable for preventing relative movement between the positioning counter element and the positioning element in the directions of at least one plane. A cross section of the cavity optionally decreases towards the interior of the cavity. A spacing between two opposing points of one edge of the cavity is optionally smaller than a depth or a depth of travel by which the positioning element can be inserted into the cavity. The vessel holder is optionally a device for processing liquids.

An apparatus for processing biological material is also proposed, comprising the following parts: a centrifuge; a vessel holder in the centrifuge, which has a holding member for holding a vessel for receiving biological material; and a positioning element. The vessel holder comprises a positioning counter element which is shaped so as to position an angular position and/or a deflection angle of the vessel holder in the centrifuge, by engagement with the positioning element.

It is also useful if the apparatus is easy to operate. For example, it is useful to provide a front portion or some other easily accessible portion of the apparatus for supplying with consumable material and for removing the used consumable material. In particular it is useful to provide this section as a removable or pull-out section, for example in the form of a drawer or a plurality of drawers.

It is also useful if the apparatus is able to detect typical operating or loading errors at an early stage. For example it is useful to check user inputs for consistency with one another and with a chosen procedure. It is also useful to check the loading with consumable material (e.g. with processing fluid, with vessels and/or with pipette tips) for consistency with one another and with a chosen procedure.

It is also useful to make the user guidance as uncomplicated as possible so that the processing can be started after the fewest possible input steps, which should be as intuitive as possible. It is useful, for example, to provide a structured menu guide using a graphic display. It is also useful to design the menu guide so that input fields which seldom need to be changed can be reached through optional sub-menus which can normally be missed out. It is also useful if the apparatus stores the last-used or frequently used settings and provides them for rapid access.

It is also useful to make the apparatus flexibly adaptable to a number of different procedures. In particular, it is useful if a broad spectrum of "bind-wash-elute" and other procedures can be supported, as provided for example by the firm QIAGEN. It is also useful if other procedures for processing biological material can be added by means of software updates or if existing procedures can be amended. It is also useful if the apparatus is able to recognise a variable number of samples for investigation (batch size) and/or flexibly support them.

It is also useful to adjust the temperature of a centrifuge, and in particular to cool the centrifuge. For this purpose a centrifuge for centrifuging biological material is proposed which comprises the following parts: a container, a lid for the container, a centrifuge rotor arranged inside the container, a drive for the centrifuge rotor, a first cooling device for cooling the lid and a second cooling device for cooling the container.

The first cooling device is optionally a cooling device for cooling the container by means of a cooling gas. It optionally comprises a flushing device for flushing the container with the cooling gas. The cooling gas of the first cooling device is optionally ambient air.

The second cooling device optionally comprises a flushing device for flushing an outer surface of the container with a cooling gas. The cooling gas of the second cooling device is optionally ambient air. Optionally, the second cooling device is controllable independently of the drive for the centrifuge rotor, and/or the second cooling device is also designed to cool a drive.

Optionally, the first and second cooling devices are different. Optionally, the first and/or second cooling device comprises cooling ribs. Optionally, the cooling ribs are arranged horizontally and/or vertically. Optionally the first and/or second cooling device is an active cooling device. Optionally the flushing device or devices of the first and/or second cooling device each comprise a ventilator. Optionally, the lid is suitable for closing off the interior of the container, preferably from the exterior of the container. Optionally, the container is designed so that when the lid is closed the cooling gas can no longer flow into the interior of the container or the cooling gas of the first and/or second cooling device cannot flow into the interior of the container.

A process for centrifuging biological material in a centrifuge is also proposed. The process comprises the following steps: charging a centrifuge rotor with the biological material; closing a container of the centrifuge using a lid; rotating the centrifuge rotor about a rotor axis by means of a drive; cooling the container, and cooling the lid.

Optionally the cooling of the centrifuge container is carried out by flushing an outer surface of the centrifuge container with a cooling gas using a flushing device. Optionally an inner surface of the centrifuge container or an interior of the centrifuge container is not flushed with the cooling gas. Optionally the flushing device is independent of the drive. Optionally, the centrifuge rotor is arranged inside the centrifuge container.

Furthermore, a centrifuge is proposed which comprises the following parts: a centrifuge container; a centrifuge rotor arranged in an interior of the centrifuge container, a lid for the centrifuge container, and a device for cooling the lid using ambient air. The apparatus defines a flow path for the ambient air which is separate from the interior of the centrifuge container.

Optionally, the apparatus for cooling the lid comprises a flushing device for flushing the lid with ambient air. Optionally, the lid has an inner area, and the flow path passes through the inner area of the lid. Optionally, cooling ribs are arranged in a region of the lid which is in thermal contact with the flow path. Optionally, the cooling ribs are aligned in a direction of flow of the flow path. Optionally, the lid comprises means for removing heat from the interior of the centrifuge. Optionally, the ambient air is at the temperature of the environment. Optionally, the apparatus for cooling the lid comprises means for evening out the velocity profile of the ambient air sucked in, preferably using cooling rib edges which are cut at an angle and set back to different degrees.

An apparatus for processing biological material is also proposed which comprises one of the centrifuges described, i.e. a centrifuge which is equipped in order to control its temperature, particularly in order to cool the centrifuge.

A process for cooling a centrifuge is also proposed. The centrifuge has a centrifuge container, a rotatable centrifuge rotor arranged in an interior of the centrifuge container, and a lid for the centrifuge container. The process comprises the following steps: taking in ambient air and passing the ambient air along the lid along a flow path which is separated from the interior of the centrifuge container. Optionally the process is carried out in one of the centrifuges described, i.e. in a centrifuge which is equipped in order to control its temperature.

A process for centrifuging biological material in a centrifuge is also proposed, comprising the following steps: charging the centrifuge with the biological material; rotating the rotator wheel inside a centrifuge container of the centrifuge by means of a drive about a rotor axis; flushing the drive and an outer surface of the centrifuge container with a coolant.

Independently of the embodiment described. other aspects of a centrifuge are also proposed. In particular, a centrifuge for centrifuging biological material is proposed which comprises the following components: a router wheel which is rotatable about a rotor axis for receiving at least one vessel for the biological material; a centrifuge container, and a shield which is rotatable about the rotor axis, which is disposed between the rotor wheel and the centrifuge container, the height of an outer boundary of the rotor wheel being less than the height of a position which the upper edge of the vessel or of a vessel holder for the vessel occupies during the centrifuging process.

A process for determining the height of a surface of a substance in a vessel is also proposed. The substance is optionally a liquid but may also be another substance, e.g. a powder. The process comprises the following steps: the surface of the substance in the vessel is irradiated by a radiation source; the radiation coming from the surface of the substance is measured by a radiometer; depending on the radiation measured by the radiometer the radiation source, the radiometer and the vessel are brought into a spatial relationship with one another, so that a first angle between a perpendicular to the surface of the substance and a first beam passing from the radiation source to the surface of the substance, is essentially equal to a second angle between the perpendicular to the surface of the substance and a beam reflected by the first beam which passes from the surface of the substance to the radiometer; and the height of the surface of the substance is determined as a function of the spatial relationship of the radiation source, radiometer and vessel.

Optionally the irradiation is carried out through a pencil beam with a pencil diameter in the range between 0.3 mm and 3 cm, preferably between 1 mm and 6 mm, for example about 3 mm. Optionally the surface is an interface between air and liquid. Optionally, the radiation source and the radiometer are accommodated in the same housing. Optionally, the radiation source and the radiometer are in a light sensor. Optionally the bringing of the radiation source, radiometer and vessel into a spatial relationship with one another involves tilting the radiation source. Optionally a curvature of the surface of the liquid caused by adhesion forces may be taken into account. Optionally the height of the surface of the substance is determined using the fact that the first and second angles are identical.

An apparatus for processing biological material is also proposed. The apparatus comprises a vessel holder for a vessel for receiving a substance, and a fill level meter for determining the height of a surface of the substance in the vessel. The fill level meter further comprises a radiation source for irradiating the surface of the substance; a radiation sensor for measuring radiation coming from the surface of the substance; a positioning device; and a control unit. The control unit is equipped to bring the radiation source, the radiometer and the vessel into a spatial relationship with one another as a function of the radiation measured by the radiometer, so that a first angle between a perpendicular to the surface of the substance and a first beam passing from the radiation source to the surface of the substance is substantially equal to a second angle between the perpendicular to the surface of the substance and a beam reflected by the first beam, which passes from the surface of the substance to the radiometer; and in order to determine the height of the surface of the substance as a function of the spatial relationship of the radiation source, radiometer and vessel.

Optionally, the optical sensor or the light sensor of the fill level meter is also suitable for positioning a movable sensor unit or for determining the presence of a vessel, as described in this application.

Furthermore, an apparatus for processing biological material is proposed. The apparatus comprises a movable unit to which an optical sensor and an ultrasound sensor are attached; means for detecting the presence or absence of a liquid container in a holder for the liquid container as a function of sensor data of the optical sensor; and means for determining the fill level of a liquid contained in a liquid container as a function of sensor data of the ultrasound sensor.

Independently of the embodiment described, further aspects of the sensing apparatus are also proposed. Thus, an apparatus for processing biological material is proposed which comprises the following parts: a holder for a vessel for receiving biological material, the vessel having at least one vessel part with increased recognisability; a radiation source for irradiating a registration area in the holder, the registration area being associated with the vessel part having the increased recognisability; a sensor for measuring an intensity of radiation which comes from the registration area; and an evaluating unit which is equipped to register the presence or absence of the vessel by running a comparison between the intensity measured and a defined threshold.

The vessel is optionally a centrifuge vessel, a filter vessel, a collecting vessel or a pipette tip. The centrifuge vessel and the collecting vessel, e.g. a so-called spin tube or Eppendorf tube, generally having main opening for pipetting material into or out of the vessel and optionally a lid. The centrifuge vessel generally also has an outlet opening which is arranged on a side of the centrifuge vessel opposite the main opening. The vessel part with increased recognisability is optionally a membrane, a filter, a filter membrane, a lid hinge and/or a lid of the vessel.

The sensor is optionally movable. The apparatus may then be suitable for determining a position of the sensor by irradiating an adjusting mark on the apparatus and by measuring a radiation coming from the adjusting mark. The movement of the sensor is then optionally coupled in at least one direction, preferably in two directions, with the movement of a gripper for the vessel or a pipetting unit for receiving the pipette tip.

The sensor is optionally capable of determining the presence or fill level of a substance in the vessel, as will be explained below. The radiation coming from the holding region is optionally reflected radiation from the radiation source. The radiation is typically electromagnetic radiation and is preferably in the visible or in the infrared spectral range. The evaluating unit is optionally designed to record absence for a measured intensity which is below the threshold and presence for a measured intensity which is above the threshold.

Optionally the irradiation is carried out using a spot which has a diameter of between 0.3 times and 1.3 times the extent of the vessel part with increased recognisability. The radiation source and the sensor are optionally movable jointly. The apparatus then further comprises positioning means for positioning the radiation source and sensor relative to the holding area.

The radiation from the radiation source optionally has a spot diameter of about 3 mm. The vessel part with increased recognisability optionally has an area of at least 3 mm×3 mm. The vessel part with increased recognisability is generally a vessel part with increased signal difference or intensity difference between the presence and absence of the vessel.

A process for detecting the presence or absence of a vessel for receiving biological material in a holder for the vessel is also proposed. The process comprises the following steps: a registration area in the holder is irradiated, the registration area being associated with a vessel part of the vessel with increased recognisability; the intensity of radiation coming from the registration area is measured; the presence or absence of the vessel is registered by means of a comparison between the intensity measured and a defined threshold.

The irradiation and the measurement are optionally carried out by a movable sensor unit and the process optionally comprises the following step in addition to those mentioned above: positioning the sensor unit relative to the vessel holder. Optionally, the position of the sensor unit is determined by irradiating an adjusting mark on the apparatus and by measuring the radiation coming from the adjusting mark.

An apparatus for processing biological material is also proposed which comprises the following parts: a vessel holder for receiving a vessel for the biological material; a sensor unit with an ultrasound source and an ultrasound sensor; and an evaluating unit for determining, as a function of sensor data from the ultrasound sensor, the state of opening of the vessel and for determining, as a function of the sensor data of the ultrasound sensor and, when the vessel is open, the possible presence of a substance in the vessel.

The substance is optionally a fluid. The evaluating unit is optionally suitable for or arranged for determining the fill level of the substance, possibly as a function of sensor data of the ultrasound sensor. The evaluating unit is optionally suitable or designed for determining a fill level of the substance by measuring the run time between an emitted ultrasound signal and an ultrasound signal reflected by a surface of the substance. The sensor unit is optionally movable and further comprises: a radiation sensor, and positioning means for positioning the sensor unit in relation to the vessel as a function of sensor data of the radiation sensor. The radiation sensor is optionally suitable for determining the presence of the vessel. The determination may be carried out for example using the methods of determining the presence of a vessel described elsewhere in this application (cf. for example the next page).

It is optionally also proposed that the vessel has at least one vessel part of increased recognisability; and that the sensor unit has a radiation source for irradiating a registration area in the holder, the registration area being associated with the vessel part of increased recognisability. The radiation sensor is then suitable for measuring an intensity of radiation which comes from the registration area and the evaluating unit is then equipped to register the presence or absence of the vessel by running a comparison between the intensity measured and a defined threshold.

An apparatus for processing biological material is also proposed which has the following parts: a container station for keeping a supply of vessels; a marking on the container station containing information as to the nature of the vessels; and a radiation sensor for reading the marking.

The marking is optionally an element which protrudes over an edge of the container station. The marking optionally comprises at least one marking element integrally formed with the container station. The marking optionally comprises at least two marking elements, each of which codes binary information, i.e. yes/no information. The container station is optionally configured so that it can be provided in various orientations in relation to the apparatus or can be inserted in the apparatus. The marking is optionally configured so that reading of the marking is independent of a particular orientation selected from the various orientations.

The container optionally contains a plurality of holding positions, each for one vessel, and the optical sensor is then suitable for detecting the presence of a vessel in each holding position of the plurality of holding positions. The method described in the following paragraphs may be used for this determination.

Optionally, the container station contains a radiation source. The radiation source may be used for one or more of the following functions which are described hereinafter: irradiating a registration area; irradiating a marking element. Optionally, the container station also contains a plurality of holding positions, each for one vessel, the vessel in question having at least one vessel part of increased recognisability; and the radiation source is suitable for irradiating a registration area, the registration area being associated with the particular vessel part having increased recognisability. The radiation sensor is also optionally suitable for measuring an intensity of radiation coming from the registration area; and the evaluating unit is then equipped to register the presence or absence of the vessel by running a comparison between the intensity measured and a defined threshold.

The vessels are optionally pipette tips. The nature of the vessel in question may for example be a collecting volume of the pipette tip or a material of the pipette tip or a material which is contained in the pipette tip. The optical sensor is optionally a light sensor. Together with the radiation source it is optionally part of a light sensor. The radiation source is optionally suitable for irradiating a marking element of the marking, and the apparatus is capable of irradiating a marking element by means of the radiation source in order to read the marking; to measure the intensity of radiation coming from the marking element by means of the sensor, and to compare the intensity measured with a given threshold for the intensity.

A process for detecting the nature of a vessel for receiving biological material in a container station for the vessel is also proposed. The process comprises the following steps: a first marking at the container station which contains information as to the nature of the vessel is irradiated; and a first intensity of radiation coming from the first marking is measured; the type of vessel is recorded as a function of the first intensity measured.

Optionally, a second marking at the container station is irradiated, which contains information as to the nature of the vessel; and a second intensity of radiation which comes from the second marking is measured; and the nature of the vessel is registered as function of the first and second intensity measured.

A process is also proposed for checking the occupancy of a centrifuge which has a plurality of vessel holding positions each for one vessel for biological material. The process comprises the following steps. For the vessel holding positions, it is registered whether a vessel is present therein; the total number of vessels registered as present in the vessel holding positions is stored; depending on the total number of the vessels registered as present in the vessel holding positions at least one condition is determined for the distribution of the vessels in the vessel holding positions; a check is made as to whether the distribution of the vessels registered as present in the vessel holding positions meets the condition. The sample vessel position is optionally arranged in an agitator and/or heater for the sample vessel.

A process is also proposed for checking the occupancy of a centrifuge which has a plurality of vessel holders. The vessel holders are each associated with at least one vessel holding position for at least one vessel for biological material. For each of the vessel holders an empty state is defined in which there is no vessel present in an associated vessel holding position, and a full state is defined in which at least one vessel is present in any associated vessel holding position. The process comprises the following steps: for the vessel holders it is registered whether they are empty or full; the distribution and the total number of full vessel holders is stored; depending on the total number stored, at least one condition is determined for proper distribution of the full vessel holders; and a check is made as to whether the distribution of the full vessel holders stored meets the condition. Optionally, the total number of vessels present in the vessel holding positions is also stored.

In these processes, the vessel holding positions are optionally co-rotatable with the centrifuge rotor.

In the processes a sensor optionally registers whether a vessel is present in the vessel holding position; and the process then further comprises the step of registering, by means of the sensor, the number of sample vessels in sample vessel positions. The processes optionally also include the step of checking whether the number of sample vessels can be reconciled with the total number of vessels registered as present, i.e. that the two numbers coincide or that the number of sample vessels correspond to the number of sets of vessel holding positions.

The processes also optionally include the step of establishing an association which assigns one vessel holding position to one sample vessel. In this case the association optionally assigns to each sample vessel a vessel holding position in which a vessel is registered as present, or it assigns to a sample vessel a group of vessel holding positions, wherein a vessel is registered as present in at least one vessel holding position of the group. The association is typically established by issuing instructions to bring the sample vessel into a sample vessel position which is associated with the vessel holding position. The sample vessel position is optionally assigned to the vessel holding position by means of a common designation. The sample vessel position is optionally assigned to the vessel holding position by the fact that the arrangement of sample vessel positions in a sample vessel station corresponds to the arrangement of vessel holding positions in the centrifuge. The association is optionally established by producing a table which assigns the respective vessel holding position to a sample vessel position of the sample vessel.

A process for checking the occupancy of an apparatus for processing samples is also proposed. The process comprises the following steps: the number of sample vessels prepared with samples to be processed is registered; depending on the number of sample vessels prepared the necessary number and/or quantity of consumable material for processing the samples is determined; the number and/or quantity of consumable material present in the apparatus is determined; and the number and/or quantity of consumable material present in the apparatus is compared with the number and/or quantity of consumable material required.

Optionally, the vessel holding positions are co-rotatable with the centrifuge rotor. Optionally, the necessary number and/or quantity of consumable material is determined in accordance with the protocol. Optionally, the consumable material is selected from the list comprising vessels, particularly pipette tips, filter vessels, e.g. spin tubes, and collecting vessels, e.g. so-called Eppendorf tubes. Optionally, the consumable material also includes biological substances, e.g. biological fluids, enzymes and/or buffer liquids. Optionally, from determining the actual state of the consumable materials, references for the user are generated in order to produce the desired state.

A centrifuge having a rotor for holding a plurality of vessel holders or devices for processing liquids is also proposed. Each of the vessel holders is able to hold a first vessel during centrifuging, i.e. during the rotation of the rotor about the rotor axis. The centrifuge also comprises a handling unit which is capable of removing the first vessel from the respective vessel holder. In particular, this can be done while the vessel holder is in the centrifuge. Furthermore, the handling unit can connect the first vessel to a second vessel or at least partially insert it in a second vessel, the second vessel being held in the vessel holder. Optionally the gripper can be moved in directions x and y, perform a movement in directions x and y together with a pipette unit, and/or move in direction z. Movement in direction z is generally independent of the pipette unit. The gripper can be rotated, and can reposition vessels in the vessel holder. This repositioning generally comprises rotating the gripper.

A process for processing biological material in a centrifuge unit is also proposed. The centrifuge unit comprises a centrifuge with a rotatable centrifuge rotor, a vessel holder which is arranged in the centrifuge rotor and a first holding position in which a vessel for receiving biological material is held, and a gripper unit with a gripper. The process comprises the following steps for removing the vessel from the first holding position: positioning the gripper in order to access the first holding position; gripping the vessel by means of the gripper; and moving the gripper so that the vessel is removed from the vessel holder by the gripper.

The process optionally comprises the additional step of positioning a rotational position or preventing a rotary movement of the centrifuge rotor. Optionally the vessel holder is pivotally mounted in the centrifuge rotor, and the process comprises the additional step of preventing a pivoting movement of the vessel holder in the centrifuge rotor.

The preceding and following parts of the description describe individual elements and processes which can be used in an apparatus for processing biological material. The description of the individual elements and processes shown is fundamentally independent of the apparatus for processing biological material, unless specifically stated to the contrary. The individual elements and processes described can thus be combined in a different manner from that shown in the apparatus herein or may be used differently independently of one another or of the apparatus.

Description of Individual Aspects

Overview of Parts of the System as a Whole

FIG. 1a shows a plan view of the working platform 2 of an embodiment of the invention. A number of modules are shown which are useful for carrying steps of the procedure for processing biological substances. The following modules are shown in FIG. 1a:

- a centrifuge unit 200 for centrifuging biological material (see FIGS. 3a to 5);
- a reject station 740 for waste, e.g. for used pipette tips;
- a consumable goods station 700 for various consumable materials for carrying out steps of the procedure for biological substances (see FIG. 12); the consumable goods station comprises among other things a container station 710 for holding containers with buffer liquid for carrying out procedural steps. The consumable goods station 700 for consumable materials also includes a pipette tip station 720 for receiving pipette tips through a pipette unit and other containers for other fluids for carrying out procedural steps.
- a heater/agitator 600 for heating and/or agitating biological material and/or other liquids (see FIGS. 13 and 14). The heater/agitator can be used for example for carrying out lysing steps.
- a display 910 which is used for user guidance and for the input and output of other information.

The individual elements shown are arranged as modules as far as possible. They can be individually mounted on and removed from the working platform and are preferably insertable. Additional connections, e.g. for current supply or for controlling the individual modules, are provided by means of plug-in connections. To make the individual modules easy to replace it is preferable for the modules to take up a space underneath the working platform which substantially corresponds to their cross-section shown on the working platform so that they can be pushed vertically in. For reasons of space, however, it may also be advantageous for individual modules underneath the working platform to take up more of less space than the cross-section shown on the working platform.

The modular construction of the working platform suggests alternative embodiments which differ in their arrangement of the individual modules. In this way, special space requirements can be taken into account. Moreover, alternative embodiments are possible in which individual modules are omitted, as shown in FIG. 1*a*. Thus, for example, an embodiment is possible in which the heater/agitator 600 for carrying out lysing steps is omitted if there is no need for such steps to be carried out. Similarly, alternative modules for carrying out other process steps or for better carrying out process steps which are already assisted may be added. Examples of other modules include: a UV lamp; active cooling for the heater/agitator; an apparatus for automatically loading up with consumable materials, such as e.g. vessel holders, vessels, buffer liquid and other processing fluid; analysing modules for analysing the processed fluid; an apparatus for disposing of spent consumable materials; and other modules.

Figure 1B:
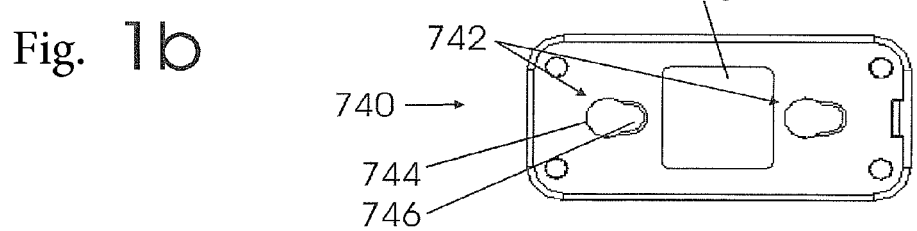
Figure 1C:
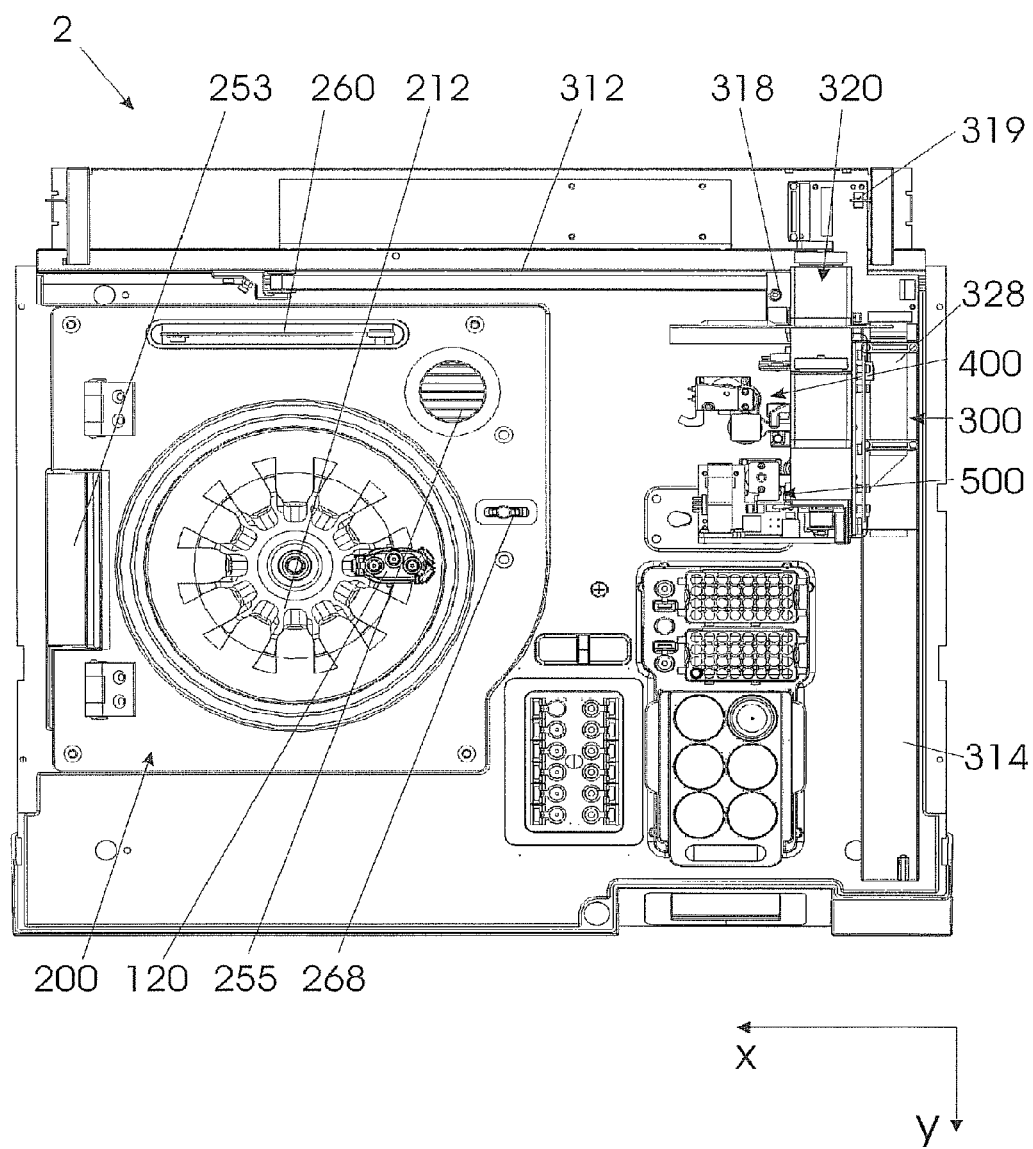

Another plan view of a working platform of an apparatus for processing biological material is shown in FIG. 1*c*. In contrast to FIG. 1*a*, in the plan view shown in FIG. 1*c* the centrifuge lid 240 of the centrifuge 200 has been removed for the purposes of illustration. This means that the centrifuge rotor 212 and a vessel holder 120 arranged therein are visible. In addition, an air inlet 253 and an air outlet channel 255 for a cooling system of the centrifuge lid are visible. In addition, a mechanism 260 for opening and closing the centrifuge lid and an element 268 for fixing the centrifuge lid in the closed position are visible. These elements are described in more detail with reference to FIGS. 3*b* and 5.

Moreover, a gripper unit 400, a pipette unit 500 and a carriage system 300 for moving the gripper and pipette unit are shown.

The carriage system 300 (cf. also FIG. 6) comprises an X-rail 312 (i.e. a rail the direction of which defines the direction X of a coordinate system) which is fixedly attached to the apparatus, e.g. to the back wall of the apparatus, and a Y-rail 314. One end of the Y-rail is mounted on the X-rail by a sliding element 318 in such a way that the Y-rail can be moved by sliding the sliding element 318 in the X-rail 312 in the direction X. The Y-rail is held by the sliding element in a horizontal position. Although the drawing does not show this, it is alternatively possible to provide a second sliding element at the other end of the Y-rail, which can slide along a second X-rail attached to the working platform 2, so that the Y-rail is held by a sliding element at each of its two ends.

A carriage member 320 can be moved along the Y-rail in direction Y, this carriage member 320 containing the gripper unit 400 and the pipetting unit 500. The gripper unit and the pipette unit can each independently be moved along the carriage member 320 in direction z (i.e. in the vertical direction, i.e. perpendicular to the plane of the drawing in FIG. 1*c*). In this way the gripper unit 400 and the pipetting unit 500 can be moved in every direction, the movement in the direction z being independent.

Depending on the complexity of the procedure followed and the arrangement of the modules alternative embodiments for moving the gripper and the pipette unit are possible. For example, an embodiment is possible in which the gripper unit 400 and the pipette unit 500 can only be moved in one direction (e.g. direction z) or can only be moved in two directions (e.g. direction x and direction z). In this case the Y-rail 314 could be omitted, for example, and the carriage member 320 could be attached directly to a fixed rail. Furthermore, one of the two rails or both rails could be replaced for example by one or more elements to produce a curved movement, e.g. by means of a pivot arm to which the carriage member 320 is attached. It is also possible for the gripper or the pipette unit to be omitted if they are not needed to carry out the desired procedural steps.

Housing, Cover

Figure 2A:
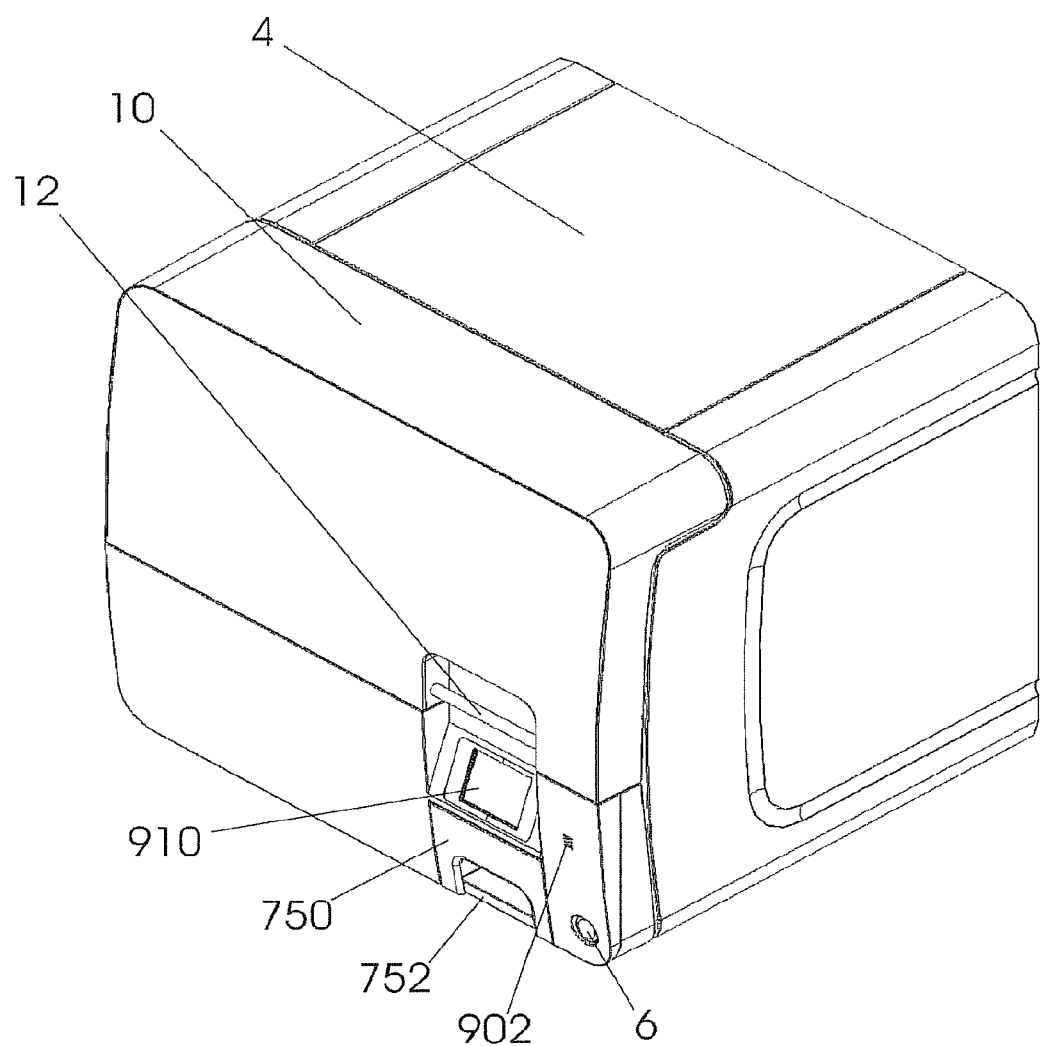
FIGS. 2a, b show a perspective view of an embodiment with the working plate of FIG. 1c and a housing.

FIG. 2*a* shows an apparatus according to the invention in perspective view. The apparatus is arranged in a housing 4. The apparatus additionally comprises a covering on the front side of the housing. The covering is closed in FIG. 2*a*. The housing 4 may be made of metal, for example, or plastics or some other robust material. The covering 10 has a handle 12 for manually opening it. The covering 10 is of transparent construction so that the interior of the apparatus can be monitored optically during operation.

It is advantageous to make the covering 10 and the housing 4 of a soundproofing construction. For this purpose the housing 4 may be provided with a sound-absorbing inner lining. Vibrating parts in the housing may also be resiliently suspended in soundproofed manner. A seal may also be provided for the covering 10. Moreover, FIG. 2*a* shows the display 910. A drawer element of a waste container 750 for consumable materials is also shown. The drawer element can be pulled out of the front side of the apparatus by means of a handle 752. In addition a loudspeaker opening 902 for a loudspeaker and an on/off switch 6 are shown. The use of the waste container is described in more detail hereinafter.

Figure 2B:
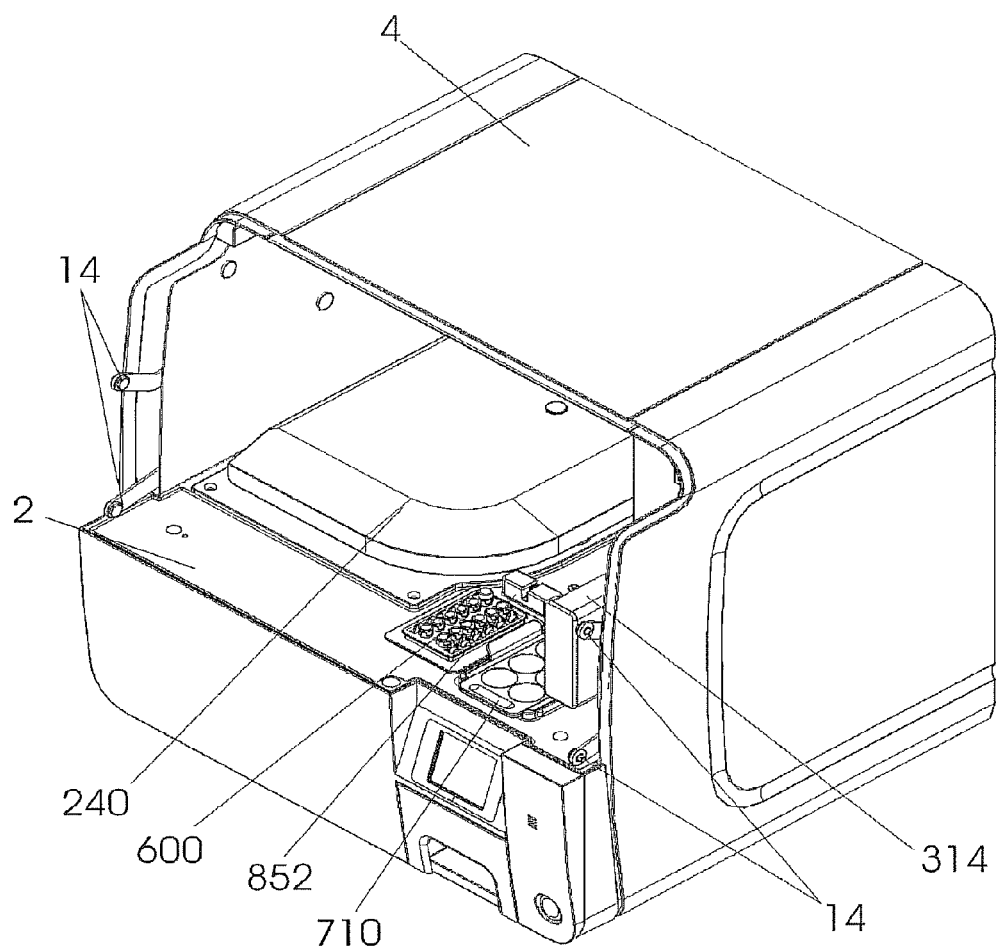

FIG. 2*b* shows the apparatus of FIG. 2*a* with the cover 10 removed. Consequently, inside the housing 4, the working platform 2 shown in FIGS. 1*a* and 1*c* with centrifuge lid 240, heater/agitator 600, fork-type light barrier 852, container station 710 and Y-rail 314 are visible. In addition, holders 14 for holding the cover 10 are shown. The holders 14 can be pivoted upwards so that the cover can be opened manually upwards.

The centrifuge and the other components are integrated into the apparatus platform in such a way that it is possible to achieve stability and substantially suppress vibration and the influence of adjacent modules.

Centrifuge

Figure 3A:
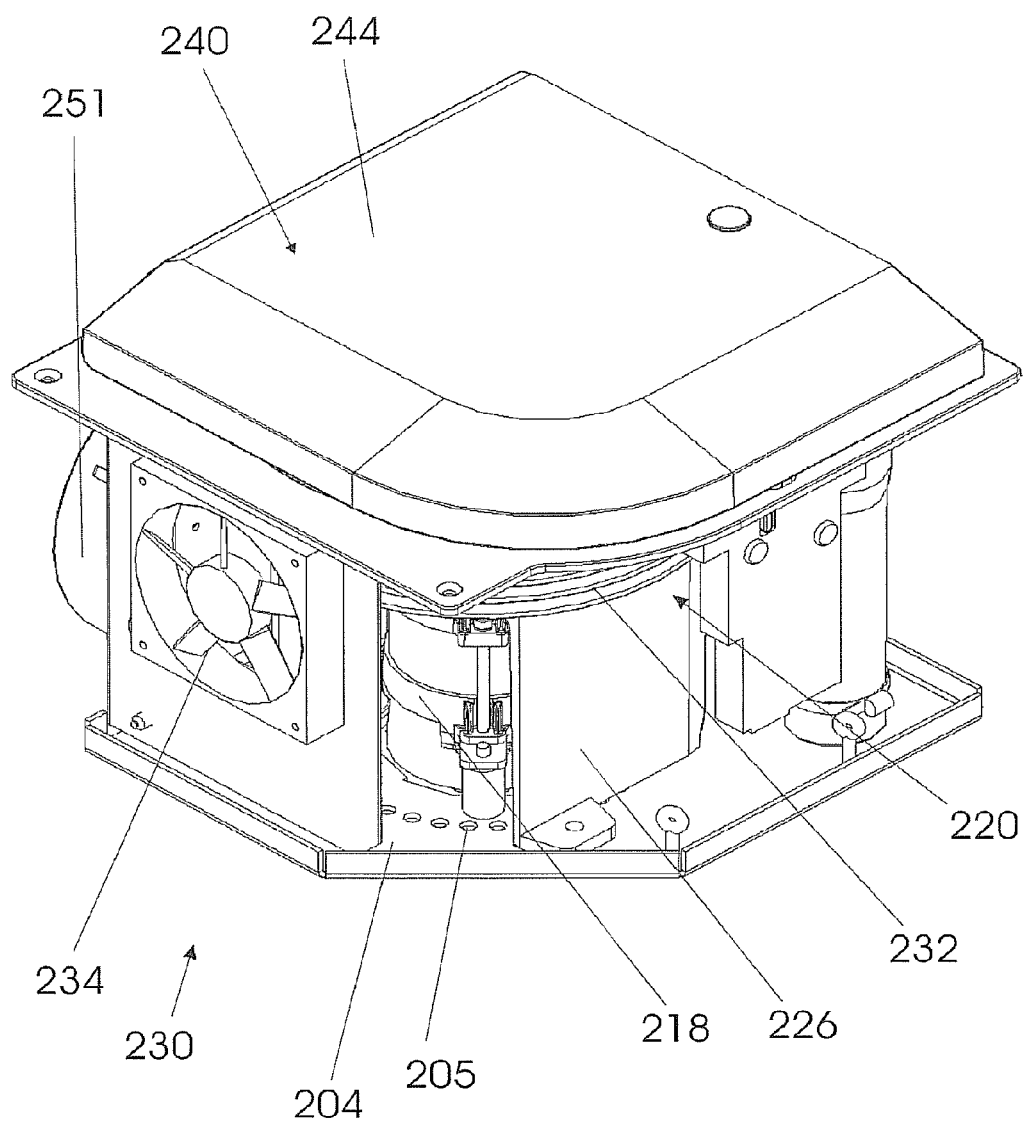

FIG. 3*a* shows a perspective view of the centrifuge 200. In this view the centrifuge lid 240 is closed so that the rotor 212 of the centrifuge cannot be seen. The centrifuge lid 240 comprises a lid cowling 244. Other parts of the lid 240 are described in conjunction with FIG. 3*c*. In FIG. 3*a* a centrifuge container 220 is shown, which surrounds the centrifuge rotor. The centrifuge container serves to screen the centrifuge rotor aerodynamically from the environment, to reduce noise and as a safety measure in the event that parts should become detached at a high rotor speed. Also visible is the centrifuge drive 218 which is in the form of an Asynchronous electric motor. Other forms of drive e.g. using a belt or a chain are also possible. The drive shown is designed for a speed of about 0-15,000 rpm.

Figure 11:
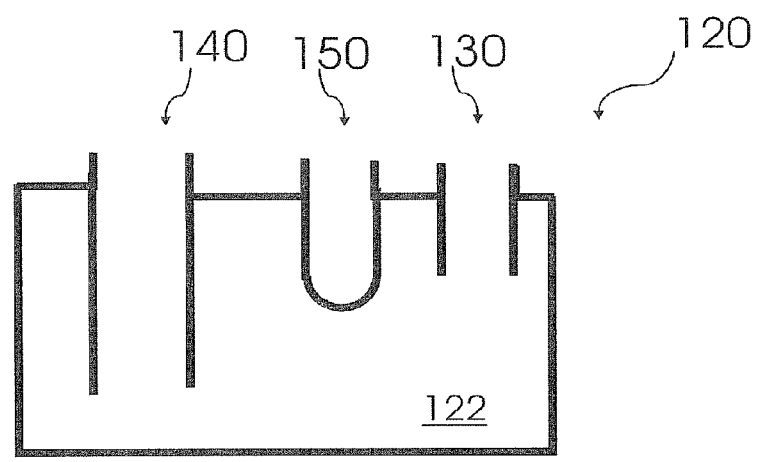
FIGS. 11a-d show a side view of a vessel holder of one embodiment.
Figure 11:
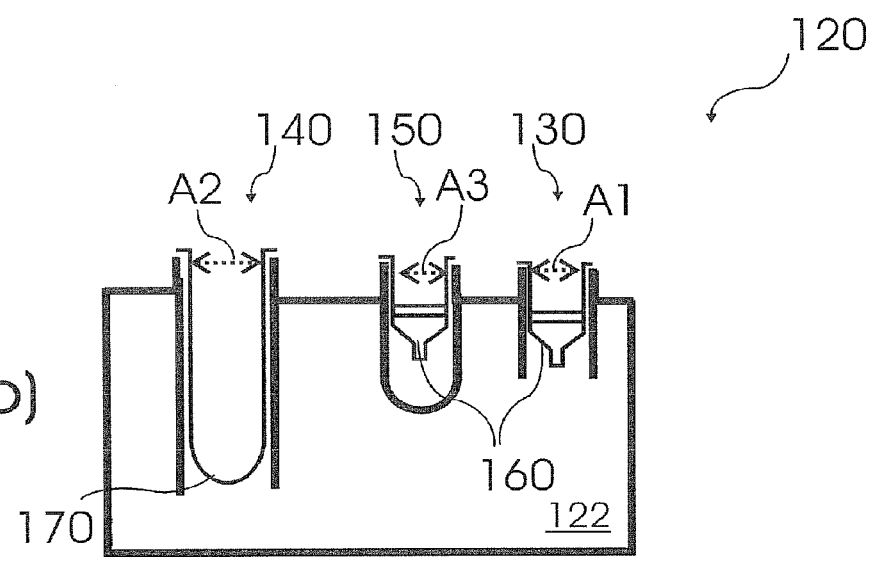
Figure 11:
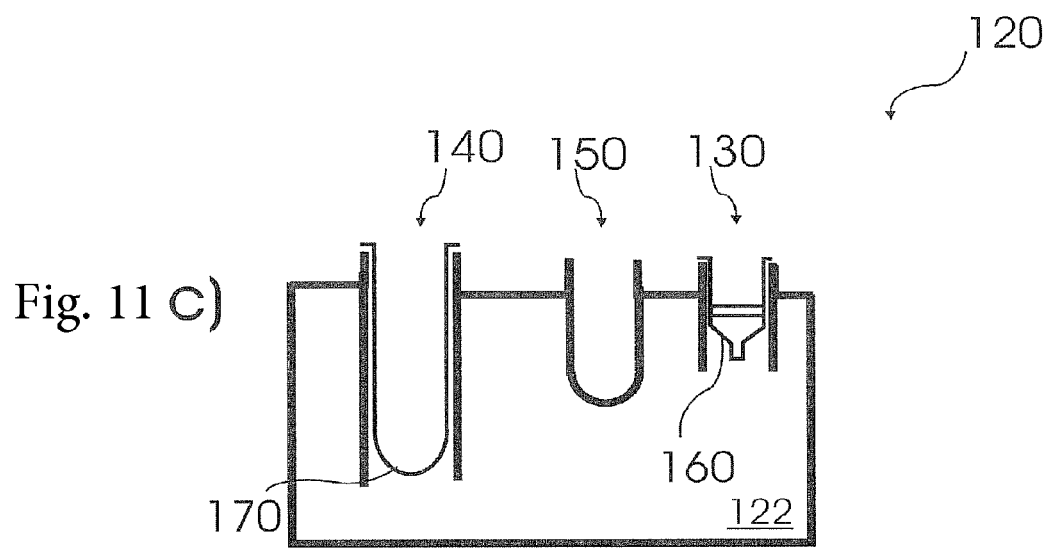
Figure 11:
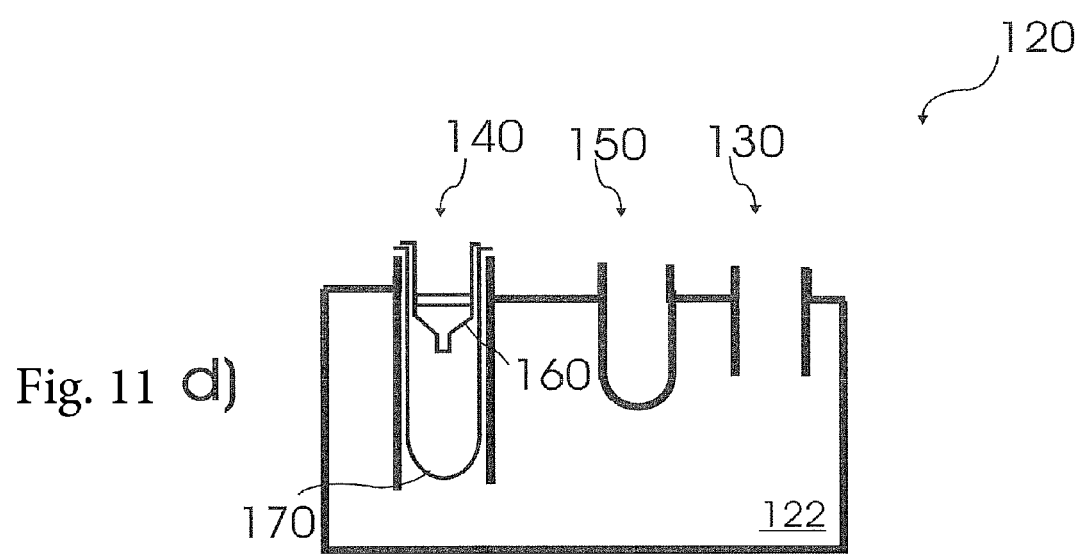

In FIG. 3*b* the centrifuge 200 is shown with the centrifuge lid 240 open. Here the centrifuge rotor 212 is shown which is rotatable about a centrifuge spindle 214. Also shown is a shield or rotor dish 216 which is rotatable together with the centrifuge rotor 212 about the centrifuge axis 214. The centrifuge rotor 212 comprises means for suspending a vessel holder 120. A vessel holder 120 of this kind is shown in FIG. 11. In principle, several of the positions provided for this purpose may be occupied by a vessel holder, while preferably attention should be paid to ensuring that the vessel holders are uniformly distributed around the centrifuge rotor so as to minimise any imbalance. In addition, an inner wall 222 of the centrifuge container is shown which does not rotate with the centrifuge rotor 212. For opening and closing the centrifuge lid 240 a transmission rod 262 is shown which is driven by a drive (not shown). Also shown is a closure member 267 of the lid which can be passed into a corresponding mating part 268 and held by means of a locking mechanism 269 so that when the lid is closed it is securely held in the closed position. A seal 228 for the centrifuge lid is also shown which at least partially seals off the interior of the centrifuge container 220 when the centrifuge lid 240 is closed. When processing biological samples it may lead to better results if the temperature in the centrifuge can be kept within a prescribed temperature range. In particular the results can be improved if any frictional heat produced during centrifuging can be minimised or discharged outwardly.

Figure 3C:
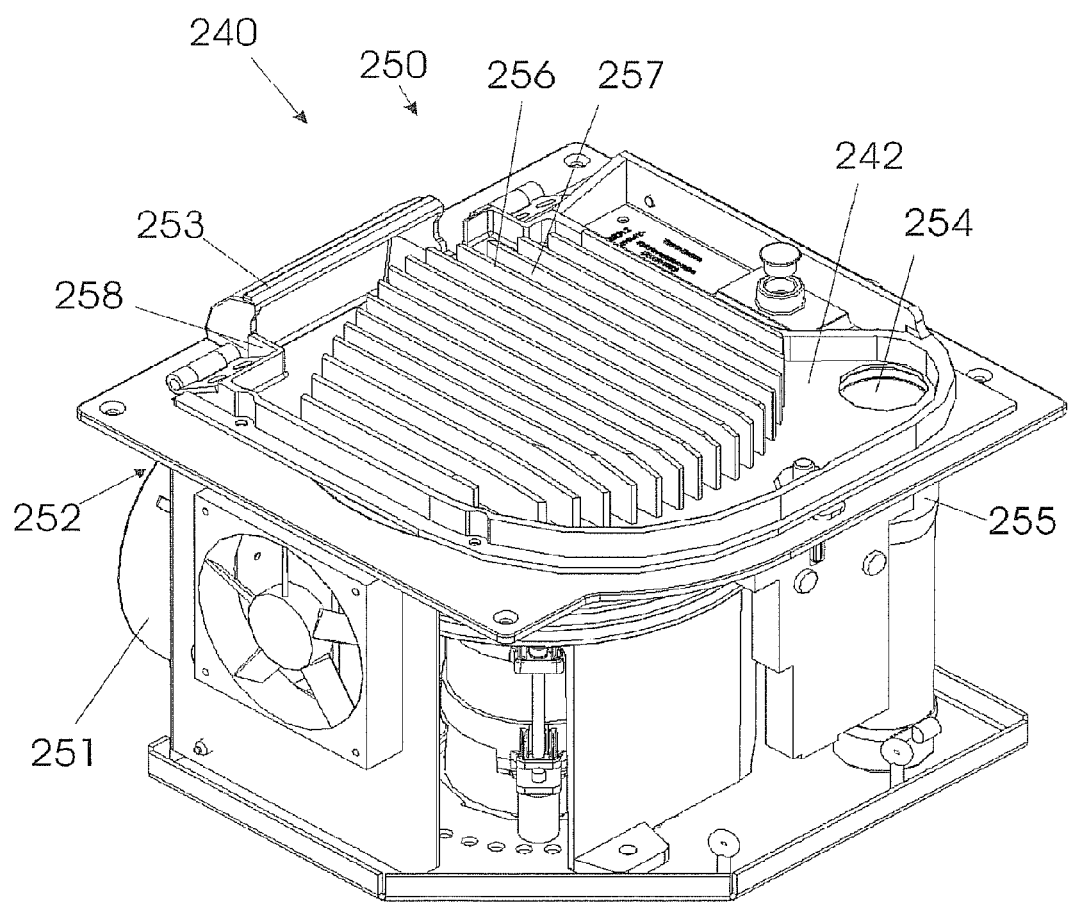

The centrifuge shown in FIGS. 3a, 3b and 3c is equipped with a cooling system which partly meets these requirements. The cooling system shown allows heat to be discharged out of the centrifuge. The cooling system shown also enables the air flow inside the centrifuge to be favourably influenced.

One element of the centrifuge cooling system is an external cooling 230 of the centrifuge container 220. The external cooling 230 is shown in FIG. 3a. The external cooling comprises cooling ribs 232 which allow heat to be efficiently given off from the centrifuge container 220 or its outer wall to the ambient air. Another form of cooling surface other than the cooling ribs 232 shown is also conceivable. For example, cooling ribs constructed in any other manner, a coating of a particularly heat conducting material or some other surface which allows heat to be given off efficiently into the ambient air is also possible. Independently of the embodiment shown a surface or an arrangement with a heat transfer coefficient of over 50 W/(m$^2$K) is preferred, while a heat transfer coefficient of more than 100 W/(m$^2$K) is particularly preferred and one of over 150 W/(m$^2$K) is most particularly preferred.

Furthermore, the ventilator 234 shown serves to externally cool the centrifuge container 220. It blows air over the outer wall of the centrifuge container. This also results in a more efficient discharge of heat into the outer air. However, the ventilator 234 could also be omitted or replaced by some other device, e.g. a device for flushing with an alternative cooling gas such as nitrogen, for example, or with a liquid coolant (e.g. water cooling).

In order to direct the air current outwards, holes 205 are provided in the bottom of the centrifuge 204. Lateral air removal slots are also possible if the centrifuge is arranged on one edge of the apparatus 1 or if suitable air outlets such as hoses are provided. In the embodiment shown the ventilator 234 has the advantage that not only the cooling ribs 232 or the exterior of the container wall 222 but at the same time also the drive 218 of the centrifuge rotor 212 can be flushed with a cooling gas.

The centrifuge cooling shown in FIGS. 3a to c avoids air or any other coolant entering the inside of the centrifuge container. Moreover, the seals 228, 229 and the protecting ring 215a and the nature of the container wall 222 help to prevent the penetrating of cooling gas. Independently of the embodiment shown it is favourable if the cooling gas does not flow over the interior of the centrifuge container 220. In other words, cooling air or another cooling gas does not enter the interior of the centrifuge container, i.e. the interior of the centrifuge container is shielded from the cooling gas or the current of cooling gas.

Another device for cooling the centrifuge or for discharging heat from the interior of the centrifuge is a lid cooling system 250 for cooling the centrifuge lid 240. Cooling the centrifuge lid 240 has the advantage that the air heated inside the centrifuge lid rises and thus has a tendency to move towards the lid. As a result the heat can be removed particularly efficiently through the lid. Various embodiments of a cooling device 250 for the centrifuge lid 240 are conceivable.

One such embodiment is shown in FIGS. 3a to 3c. It comprises a ventilator 251 which takes in ambient air in order to cool the centrifuge lid 240 and blows it towards the centrifuge lid 240. The air is guided through an air inlet channel 252 to the centrifuge lid 240. The air is introduced into the centrifuge lid by means of an introduction device which comprises an air inlet 253 and a corresponding air inlet opening 258 into the lid 240. The air is passed or blown through an interior of the centrifuge lid 240, thereby absorbing heat from the centrifuge lid and carrying it away again. In this way the air is able to discharge the heat from the centrifuge lid. The air is discharged through an air outlet opening 254; the heated air passed through the lid can escape from the lid through the air outlet opening 254 and is then guided through an air outlet channel 255 to the base of the apparatus and then out of the apparatus.

FIG. 3c shows the centrifuge lid 240 with the lid cowling 244 removed (see FIGS. 3a and 3b). This shows that the lid base 242 of the centrifuge lid has cooling ribs 256 which define channels 257 for the air current. The cooling ribs 256 and the enlarged surface of the lid ensure an efficient discharge of heat from the centrifuge lid 240 to the air flowing through the lid. Analogously to the cooling ribs in the container 232, here again it is possible to have alternative forms of the surface inside the lid.

Alternative embodiments which differ in their nature of cooling of the lid are also possible. For example, the lid cowling 244 of the centrifuge lid can be removed and/or the ventilator 251 can be omitted. In the latter case the centrifuge lid is cooled passively by the ambient air. It is also possible to cool the lid with a coolant liquid such as water, for example. In this case it is advantageous to supply and remove cooling liquid to and from the surface of the lid using flexible tubes so that the lid can be open and closed without any difficulty in spite of the tubes. Independently of the embodiment shown a surface area or an arrangement having a heat transfer coefficient of more than 50 W/(m$^2$K) is preferred, a coefficient of more than 100 W/(m$^2$K) is particularly preferred and one of over 150 W/(m$^2$K) is most particularly preferred.

FIG. 3b shows the rotor dish or shield 216 as another component of the centrifuge. As described more accurately in connection with FIG. 4, the rotor dish 216 affects the development of heat and the air flow inside the container of the centrifuge (see FIG. 4). Independently of the embodiment shown, no holes or other openings are provided outside the centrifuge spindle 214 in the rotor dish 216.

Moreover in FIG. 3b the rotor 212 of the centrifuge is shown. The rotor has 12 receiving positions for receiving vessel holders 120. The receiving positions are numbered. The first receiving position, marked with the number "1", may optionally also be marked with an easily recognisable marking, e.g. a coloured marking (not shown). The rotor comprises holders for suspending means 110 for the vessel holder 120. If the suspension means 110 with the vessel holder 120 are suspended from the holders they are pivotable about a horizontal axis relative to the rotor 212. FIG. 3b shows for example a vessel holder 120 which is suspended in the rotor 212 by the suspending means 110 and is pivoted outwards about the horizontal pivot axis. The suspension means 110 may be integrally formed with the vessel holder 120 or may be formed separately from it. In the latter case the vessel holder 120 may be designed to be insertable in the suspension means 110. In a preferred embodiment the vessel holder is made of plastics and the suspension means are made of metal, e.g. aluminium.

The rotor also represents a stop for a maximum pivoted position about the horizontal pivot axis of the vessel holder 120 or its suspension means 110. The stop defines a maximum pivot angle of the vessel, in that it comes into contact with part of the rotor 212 when the maximum pivot angle is reached. Preferably the maximum pivot angle is in an outward direction of pivoting, i.e. in a direction of pivoting produced by a centrifugal force generated when the rotor 212 rotates about its axis 214.

By the use of different suspension means 110 or different methods of mounting the vessel holder 120 in suspension means 110—for example different orientations of the vessel holder 120 in the suspension means 110—it is possible to define different stops for different maximum pivot angles. For example, pivot angles of 90°, 60°, 45°, 30° and 15° can be supported.

In addition, a stop can be provided for pivoting the vessel holder 120 inwards. Both stops may be mounted on the centrifuge rotor 212 or on some other part of the centrifuge 200. Further details of the stop and of the centrifuge rotor 212 are described on Page 39, Line 11 to Page 43, Line 6, in FIGS. 17 and 18 and in claims 61 to 68 of the Patent Application EP 05020948.5, these sections hereby being incorporated in the description of the present application.

Figure 4:
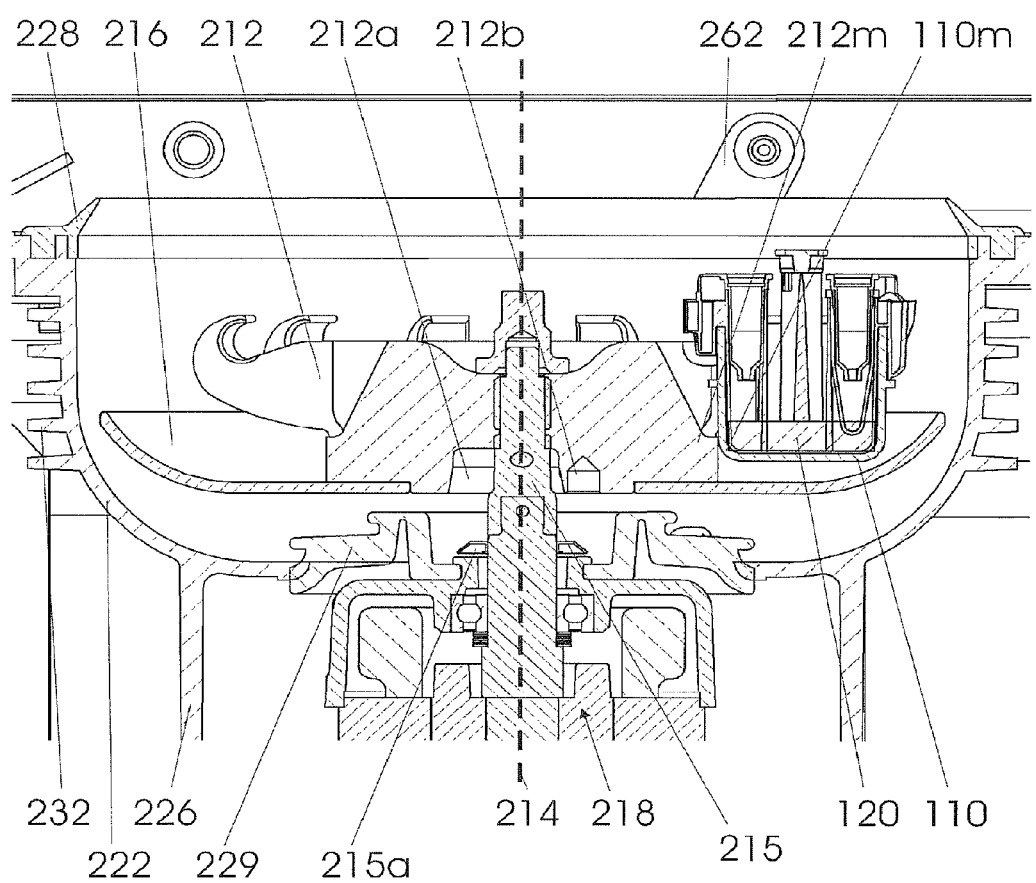

FIG. 4 shows a lateral cross-section through the centrifuge rotor along a cross-sectional plane which contains the rotor axis 214. Rotatably mounted about the rotor axis 214 are an output sections of the motor shaft 215, a rotor wheel 212, a vessel holder 120 mounted thereon, and a rotor dish 216. The motor 218 serves to drive the motor about its rotor axis. Elements shown which are not rotatable about the rotor axis comprise the container wall 222 of the centrifuge container 220, a container carrier 226 for carrying the container wall, fixed parts of the motor 218 and a sealing element 229 between the outer wall of the motor 218 and the container wall 222, as well as a sealing ring 228 for sealing the gap between the container wall 222 and a lid of the centrifuge (not shown in FIG. 4). In addition, a protecting ring 215a of the output of the motor shaft 215 serves to screen the interior of the motor 218 and the interior of the centrifuge container 220 from one another.

The output of the motor shaft 215, the rotor wheel 212 and the rotor dish 216 are joined together. The rotor wheel 212 can be changed by the user. For this purpose it is screwed to the output of the motor shaft by means of a screw element of the output of the motor shaft 215 (uppermost element of the output of the motor shaft 215) and additionally connected to the output of the motor shaft by a pin for transmitting a rotary movement. A recess 212a is provided in the rotor wheel 212 for mounting the pin. In order to ensure that the recess 212a does not give rise to any imbalance, an equalising bore 212b is also provided.

The cross-section of FIG. 4 also shows a vessel holder 120. The vessel holder is shown in more detail in FIG. 10. The vessel holder is inserted in suspension means 110, e.g. aluminium suspension means.

Figure 5:
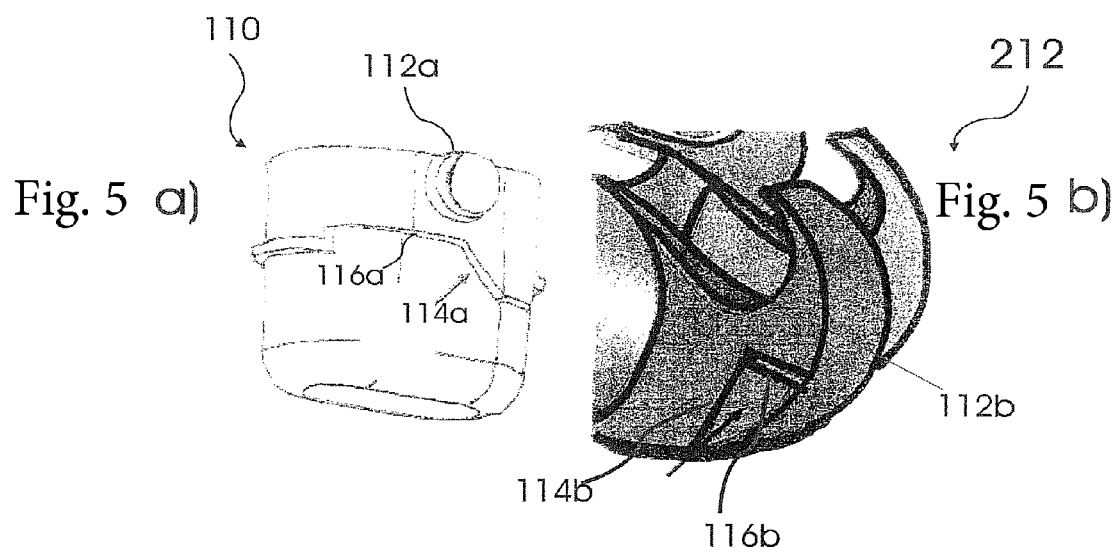
FIGS. 5a-c show a vessel holder suspended in the centrifuge rotor of the centrifuge and a stop for a maximum pivot angle of the vessel holder.
Figure 5:
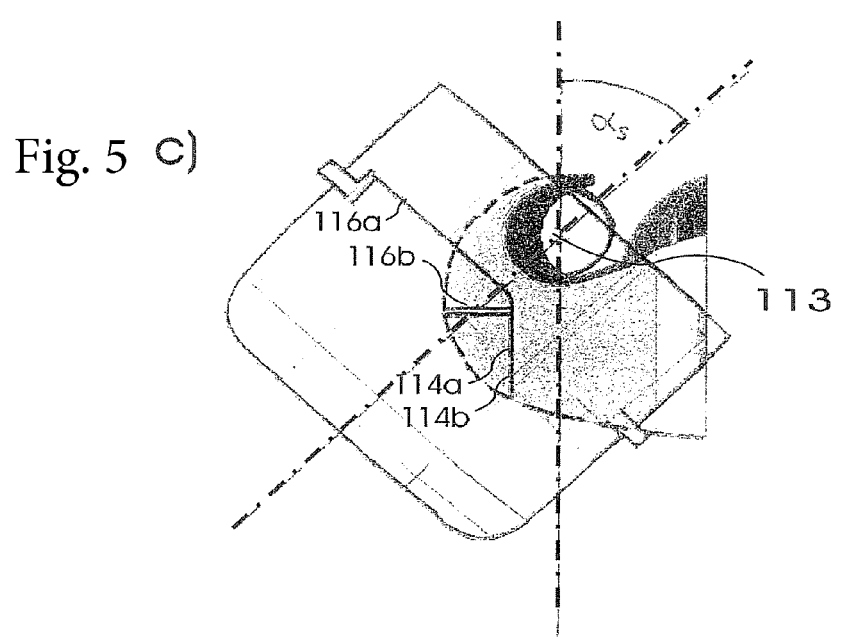

As shown in FIG. 5, the suspension means 110 can be suspended in the centrifuge rotor 212. For this purpose the suspension means 110 comprise axial portions 112a which are suitable for inserting the suspension means in suspension elements 112b of the centrifuge rotor 212 provided for this purpose. When the suspension means 110 are suspended in the centrifuge rotor 212, they and the vessel holder 120 inserted therein are pivotable about a horizontal spindle 113.

FIG. 4 shows the vessel holder in its resting position relative to the horizontal pivot axis. The centrifugal forces occurring during centrifuging cause the vessel holder to pivot outwards, i.e. a lower part of the vessel holder moves away from the centrifuge axis 214. In order to limit the outward pivoting movement, a stop is provided as shown in FIG. 5. The stop is formed by an edge 114a of the suspension means which come into contact with a mating edge 114b of the centrifuge rotor when a maximum pivot $\alpha_s$ is reached, as shown in FIG. 5c. Other details of the stop are described on Page 42, Line 7 to Page 43, Line 6 of EP Patent Application 05020948.5, these sections hereby being incorporated in the description of the present application.

The vessel holder cannot pivot inwards relative to its resting position. This is prevented by the fact that a stop 212m (see FIG. 4) and/or a stop 116b of the centrifuge rotor 212 comes into contact with a corresponding mating stop 110m or 116a of the suspension means 110, as shown in FIGS. 4 and 5, respectively.

When centrifuging the biological material it is not necessary for the vessels for biological material which are contained in the vessel holder 120 to have a closed lid. Indeed, they may have no lid at all or the lid may be open. The vessels shown in FIG. 4, for example, have an open lid which is held in a lid garage of the vessel holder 120.

The centrifuge dish 216 shown in FIGS. 3b and 4 has a bottom region extending inwardly to the centrifuge spindle 214. It also has an outer edge region which is curved upwardly. This curvature means that the outer edge of the centrifuge dish 216 is at a height which is located between a lower edge and an upper edge of a vessel holder 120 when the latter is at rest in the centrifuge rotor 212.

The centrifuge dish 216 also defines an interior, i.e. a region which extends roughly to a height of its outer edge. At the same time the outside and underside of the centrifuge dish 216, i.e. the side towards the centrifuge container 220, defines a relatively smooth surface, so that the friction of the air during rotation can be minimised. Because the centrifuge dish 216 does not extend up to the upper edge of the centrifuge container 220, however, an air exchange with the wall of the centrifuge container 220 is possible at the same time, by means of which heat can be discharged towards the outer wall 222 of the centrifuge container. This allows more efficient cooling.

Figure 10:
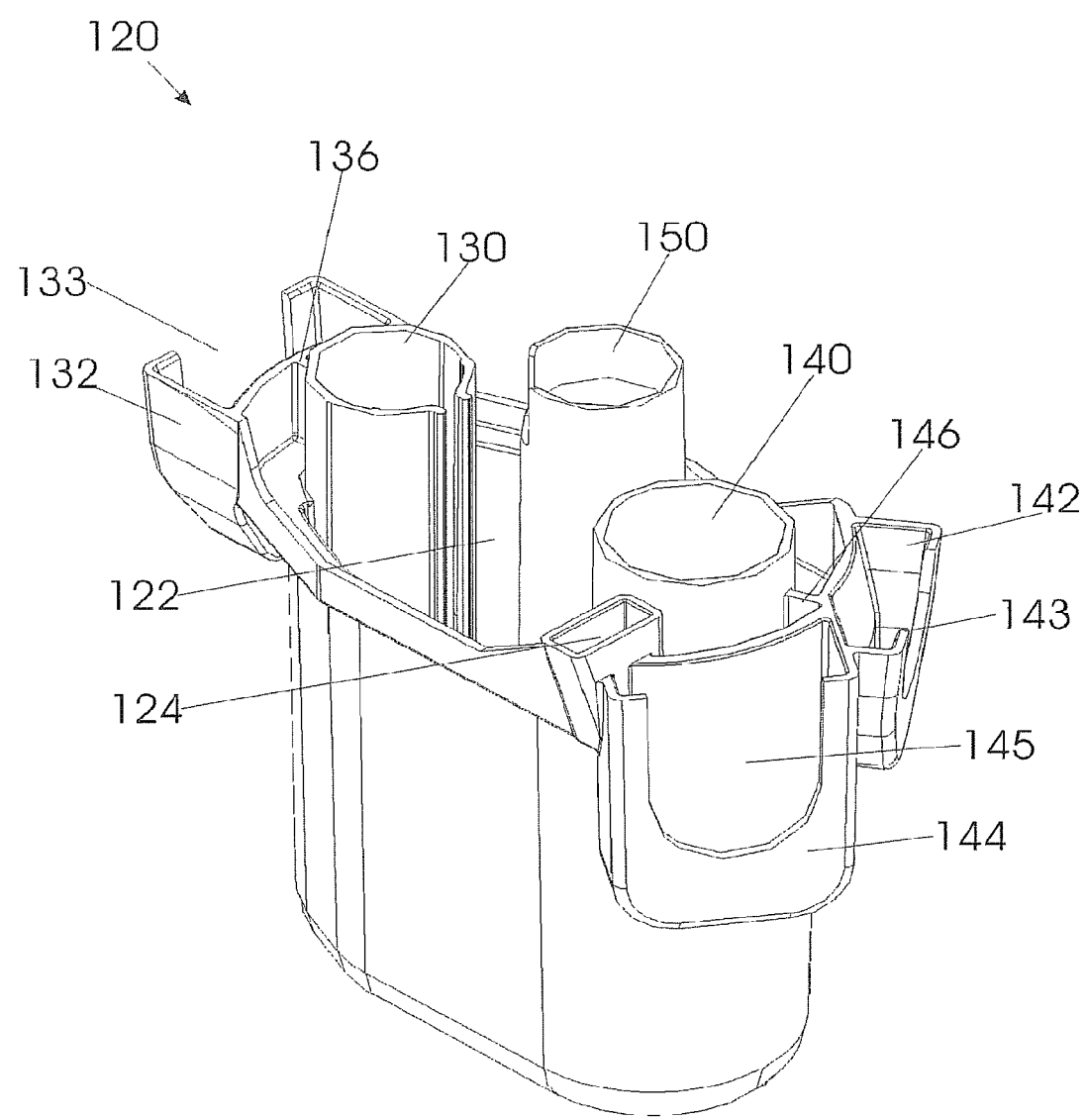
FIG. 10 shows a perspective view of a vessel holder of one embodiment.

FIG. 10 shows a vessel holder 120 for holding a vessel 160 (see FIG. 11b). The vessel holder has three holding positions 130, 140, 150 for vessels. The holding positions may each be provided for the same vessel or for different vessels. For example, in the vessel holder shown in FIG. 10, the holding position 140 for a vessel with a larger diameter than that of the holding positions 130 and 150 is provided.

The vessel holder also has a volume 122 which serves to hold liquid. The holding positions 130, 140, 150 may or may not comprise an opening for the exit of the liquid into the volume 122. Referring once again to FIG. 11a, the holding positions 130 and 140 comprise an opening through which liquid exiting through a bottom opening of a vessel held in the holding position 130 can pass into the volume 122. In the holding position 150, however, liquid leaving the vessels held cannot enter the volume 122 as these holding positions are surrounded by a solid sealed wall. Thus the holding position 150 itself can act as a vessel.

As shown in FIGS. 11a to d, the diameter A2 of the holding position 140 is greater than the diameter A3=A1 of the holding positions 130 and 150 of the vessel holder 120. As a result it is possible to insert a first vessel 170 in the holding position 140 which has an external diameter A2 which allows insertion in this holding position, and which has an inner diameter which corresponds to the diameter A3=A1 of the other two holding positions. Thus the vessel 160 for which the holding positions 130 and 150 are provided can be inserted in this vessel 170.

In particular, this arrangement enables the vessel 160 to be transferred from the holding position 130 into the vessel 170 held in the holding position 140, by means of a gripper such as the gripper 400, for example. Analogous methods of transferring vessels are described on Page 28, Line 26 to Page 31, Line 8 of EP Patent Application 05020948.5, these parts thus being incorporated hereby in the description of the present application. These methods may be carried out using the gripper 410 (see FIG. 9) or a similar gripper.

Figure 9:
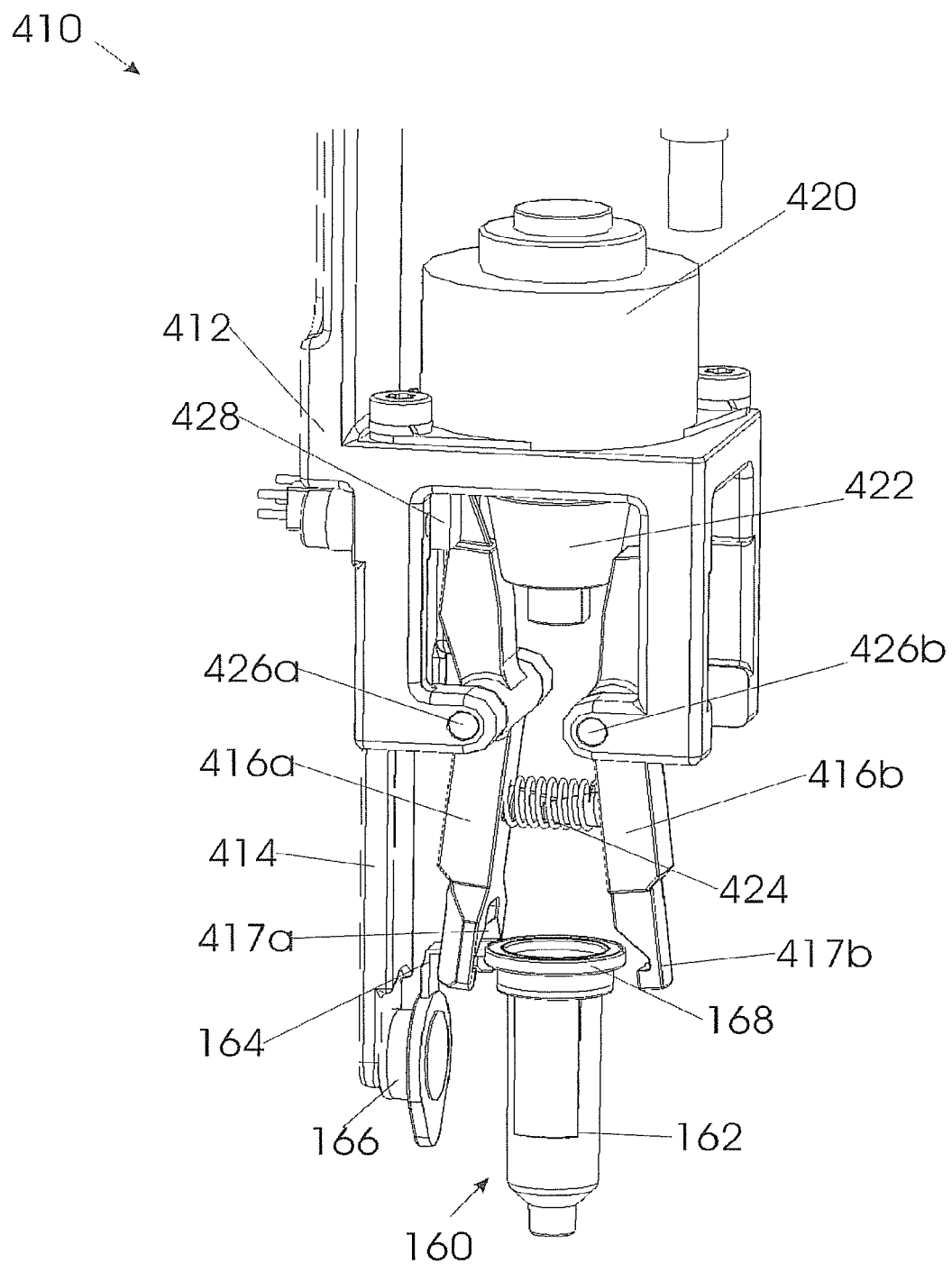
FIG. 9 shows a perspective view of the gripper of the gripper unit of FIG. 8.

The vessels to be held by the vessel holder 120 may have lids. Such a vessel 160 with a lid 166 is shown in FIG. 9, for example. Lid garages 132, 142, 144 are available for the lids on the vessel holder 120, as shown in FIG. 10. The lid garages are constructed so as to fix the lid in a secure position during centrifuging. The lid garages are constructed so as to allow access to the lid 166 by the lid holder 414 (see FIG. 9). For this purpose the lid garages comprise openings 133, 143, 145, through which the lid holder 414 can make contact with the lid and provide a stop for it, so that during removal of the vessel from the vessel holder 120 or during insertion of the vessel therein the lid can be removed from the lid garage or placed therein while retaining the position defined by the lid holder 414.

For the holding position 140, two lid garages 142, 144 are available which are provided for the respective lids of two vessels 160, 170, which are inserted together as shown in FIG. 11d.

The vessel holder also has support struts 136, 146, which serve to stabilise the holding positions 130, 140. For further stabilisation these holding positions are connected to an outer wall of the vessel holder 120. Thus the holding positions can be held in stable manner in the face of the forces occurring during centrifuging.

Figure 8:
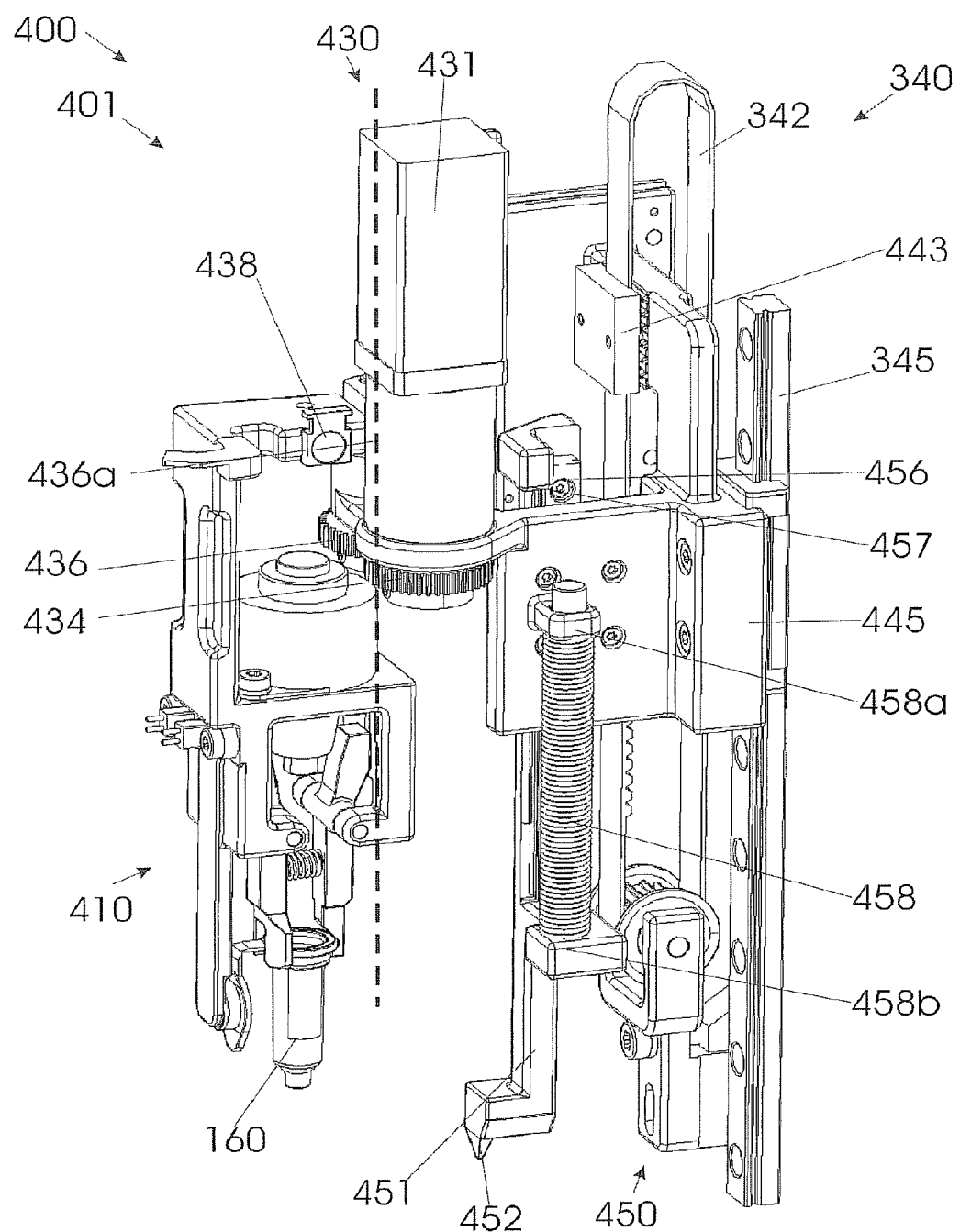
FIG. 8 shows a perspective view of the gripper unit of FIG. 6.

The vessel holder also has a positioning opening or a positioning counter-element 124. The positioning counter-element 124 is shaped so as to engage with the positioning spike or positioning element 452 of the positioning device 450 as shown in FIG. 8. As described with reference to FIG. 8 the engagement can fix or position an angular position. It can also position or fix an angle of deflection of the vessel holder in the centrifuge. The positioning counter-element 124 comprises a cavity for receiving the positioning element.

The engagement between the positioning counter-element 124 and the position element 450 is suitable for preventing relative movement between the positioning counter-element 124 and the positioning element 450 in the direction of a plane, namely the horizontal plane.

The distance between the positioning counter-element and the middle of the vessel holder is greater than the distance between the positioning counter-element and an edge of the vessel holder. The middle of the vessel holder is generally defined by the pivot axis 113 shown in FIG. 5c. The cavity tapers downwardly, i.e. the cross-section of the cavity decreases in the direction towards the interior of the cavity. A spacing between two opposing points of an edge of the cavity is smaller than a depth or a stroke depth by which the positioning element can be introduced into the cavity.

Further aspects of the vessel holder 120 are described in EP Patent Application 05020948.5 which is hereby incorporated in the description of the present application.

It is advantageous to load the centrifuge as evenly as possible so as to avoid or minimise any imbalance. For this purpose the centrifuge comprises means for ensuring that the centrifuge is loaded as evenly as possible. The means comprise Rules which contribute to substantially uniform loading even when the centrifuge rotor 212 is not fully occupied.

In one embodiment the Rules may be used for automatic loading of the centrifuge rotor 212. In an alternative embodiment the Rules may be used for checking manual loading. If in this case the loading does not conform to the Rules or does not have a sufficiently favourable distribution with regard to imbalance, a warning or error message may be emitted. At the same time suggestions for improved loading may be given.

The Rules may demand, for example, that the centre of gravity of the vessels with which the centrifuge is loaded coincides with the rotor axis 214. For this purpose each vessel may be associated with a Vector the direction of which corresponds to the angle about the rotor axis 214 in which the vessel is arranged in the centrifuge rotor. Then the Rules may require that the sum of the Vectors is zero or falls below a given threshold. If the vessels are of different weights, the Vector length may be proportional to the weight of the vessels.

For automatic loading, other Rules may be provided. For example, the Rules for automatic loading of P positions with B vessel holders or with vessels may require uniform distribution. Precisely every (P/B)th position of the centrifuge rotor is occupied if P is divisible by B. If P is not divisible by B and if B' is the next greater divisor of P compared with B, in addition (B'-B) empty vessels or vessel holders can be loaded, so that the B' vessels are evenly distributed.

Moreover, the control of the drive may permit detection of an imbalance from the data of an acceleration sensor which is part of the drive 218 of the centrifuge. In this case an error message may be generated and centrifuging may be stopped if the imbalance or a time average of the imbalance exceeds a given threshold.

If it is envisaged that material is to be loaded into the centrifuge or unloaded from it or transferred in it, or steps are to be carried out for processing or analysing the material in the centrifuge, it is advantageous if the rotor of the centrifuge can be positioned and/or if its position can be detected. The position of the rotor is an angle of rotation of a place on the centrifuge rotor (e.g. a defined element which is co-rotatable with the centrifuge rotor 212, such as a holder or holding position for a vessel or marking) relative to a reference angle which is not co-rotatable. The positioning is the recognition of the position or the bringing into the position or holding or fixing in the position.

The control of the centrifuge rotor can be used to position it. If a desired position is preset in the control, the control ensures that the position is reached and optionally held with a given degree of accuracy. In this way, for example, vessel holders or vessels needed for individual processing steps can be brought into a position for interaction with a suitable processing means, possibly a pipette unit or a gripper or an analysis device.

The drive 218 of the centrifuge may be an Asynchronous motor. This typically has the advantage that an Asynchronous motor can be robust and cheap in construction and is suitable for high speeds and smooth operation. Compared with a Servomotor, however, an Asynchronous motor has the disadvantage that it is difficult to position as the control data required for this are not immediately available.

However, the Asynchronous motor can be fitted with Vector control. Vector control is described in the prior art, e.g. in the publication by A. Fitzgerald et al entitled "Electric Machinery" (McGraw-Hill, 2003). The Vector control provides a controllability of the Asynchronous motor which is comparable with that of a Servomotor. In this way it is possible to achieve both advantageous behaviour at high speeds and positioning of the centrifuge rotor.

Therefore, independently of the embodiment described, it is proposed to provide a centrifuge for biological material, preferably a laboratory centrifuge, which has as the drive for a rotor of the centrifuge an Asynchronous motor with Vector control. The Asynchronous motor is also equipped with means for positioning the rotor at a given angle of rotation about the rotation axis of the rotor. Preferably, the means comprise a sensor for determining the angle of rotation of the rotor.

It is also possible to regulate the positioning by means of an Asynchronous motor with speed feedback. A process with modified U/f-characteristic control is proposed. In this process an actual current value is detected and fed into a speed regulator. The positioning is then regulated using active sinusoidal currents.

Mechanical Positioning of the Centrifuge with Spike

In addition, positioning may be carried out using a positioning element which is not co-rotatable with the centrifuge rotor, and which is suitable for interaction with at least one positioning counter-element which is co-rotatable with the centrifuge rotor. The interaction may be a mechanical engagement, a magnetic interaction or the reading of a marking, for example. For the interaction it is advantageous if in a first step coarse positioning has already been carried out, e.g. by controlling the centrifuge rotor, so that the positioning counter-element and the positioning element are in a range of interaction with one another. It is also advantageous to provide a plurality of positioning counter-elements. For example, it is advantageous to provide a correspondingly arranged positioning counter-element for all the positions in which the centrifuge rotor is to be positioned.

One example of a positioning element 450 and a corresponding positioning counter-element 124 is described in more detail in the description of the gripper (see FIG. 8); the skilled man will know how to implement other positioning elements and counter-elements as described herein analogously, particularly those which are not attached to the gripper but, for example, to the centrifuge container 222 or to the working platform 2 of the apparatus 1.

Carriage for Gripper and Pipette Unit

Figure 6:
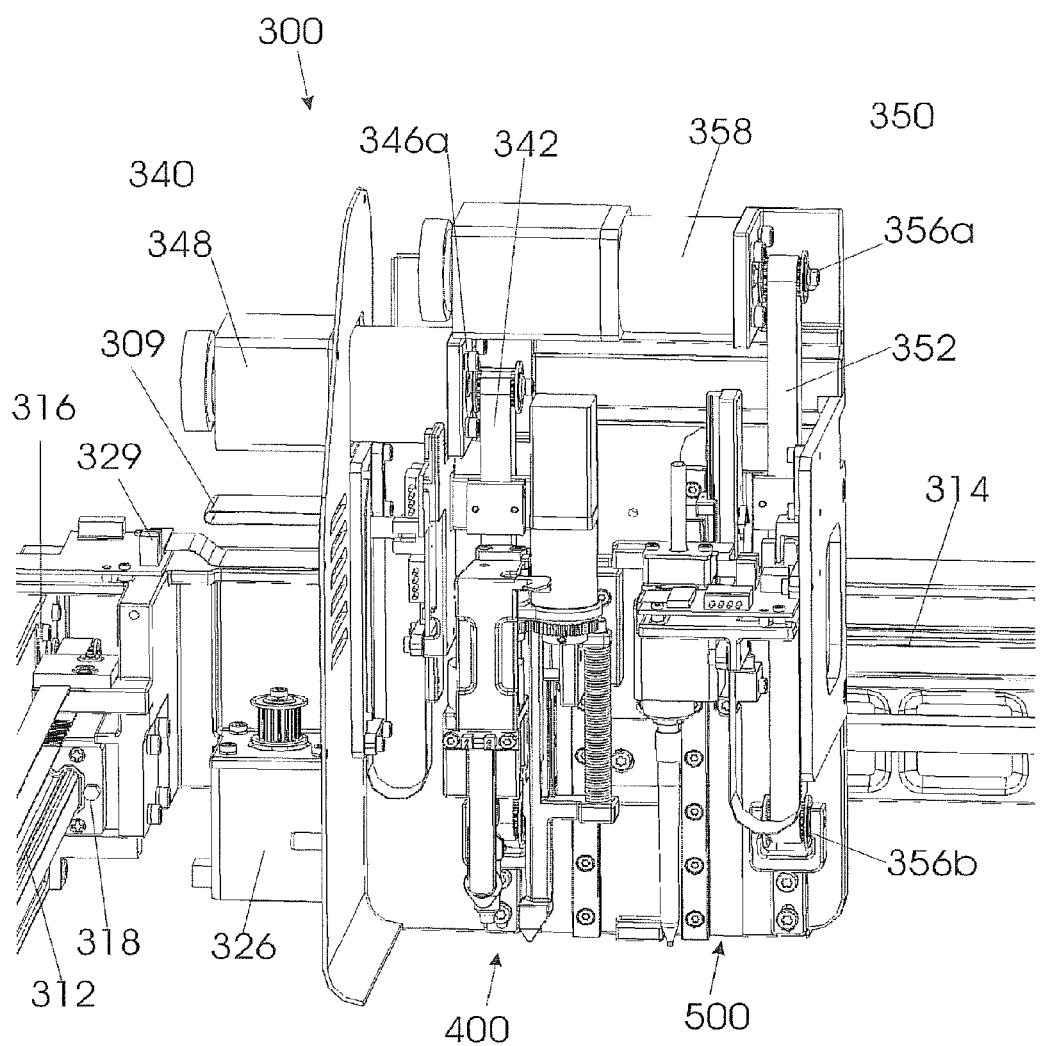
FIG. 6 shows a perspective view of the gripper slide of an embodiment with a gripper and pipetting unit.

FIG. 6 shows a perspective view of the carriage system 300 for moving the gripper unit 400 and pipetting unit 500. The carriage system 300 comprises a fixedly mounted X-rail 312 and a Y-rail 314. The Y-rail 314 is connected to the X-rail by means of a sliding element 318. The sliding element 318 can slide along the X-rail 312 in direction x and thus move the Y-rail 314 in direction x.

For moving the Y-rail 314 in direction x, a drive 316 and a drive belt are provided. The drive belt is suspended from two rollers. The drive can drive the rotation of one of the rollers; the rotation is converted into an advancing movement of the drive belt. For this purpose the rollers and the drive belt are preferably shaped so that engagement takes place between them, i.e. the drive belt is a toothed belt. The drive belt is firmly connected to the X-rail via fixing means. The fixing means ensure that the advancing movement of the drive belt bring about movement of the Y-rail along the X-rail, i.e. in direction x.

The carriage system 300 also comprises a carriage member 320 (see FIG. 1c). The carriage member 320 is movable along the Y-rail in direction y. For this purpose the carriage member is connected to a sliding element 328 (see FIG. 1c) which is able to slide along the Y-rail 314 and thereby move the carriage member in direction y. A drive 326 is provided for driving this movement. The sliding element 328 and the drive 326 are constructed analogously to the drive 316 of the Y-rail in direction x. The drive 326 is connected to the Y-rail and is not movable with the carriage member 320. The drive 316 and 326 are in the form of stepping motors, so that accurate positioning of the carriage member 320 in direction xy is possible. The control of the stepping motors is more accurately described with reference to FIG. 16. A flat band cable 309 connects the carriage system 300 to a control unit; it corresponds to the connecting cable shown in FIG. 16 between the interfaces 871a and 871b.

The carriage member 320 has a suspension means 340 for the gripper 400. The suspension means permit movement of the gripper 400 in direction z. For this purpose the suspension means 340 comprise a gripper rail 345 along which the gripper 400 can be moved in direction z (see FIG. 8). In addition a drive 348 is provided for this movement, driving a lifting belt 342 analogously to the drive of the drive belt of the Y-rail 314. The lifting belt 342 is guided over two rollers 346a, b and can be moved by means of the drive. The gripper 400 is attached to the lifting belt 342 by a clamping fixing 443 so that it moves in direction z as the lifting belt advances.

In addition, the gripper carriage comprises suspension means 350 for the pipetting unit 500. The suspension means 350 allow movement of the pipetting unit in direction z analogously to the suspension means 340 for the gripper 400. In particular, the suspension means 350 contain a lifting belt 352, a rail 355 (cf. FIG. 7) along which the pipetting unit can be moved in direction z, rollers 356a, b, around which the lifting belt is guided, and a lifting drive 358 for driving a lifting movement of the pipetting unit in direction z. These elements are analogous to the corresponding elements for the gripper unit 400.

Thanks to this construction the gripper unit 400 and the pipetting unit 500 can be moved jointly in the horizontal plane, i.e. in directions x and y. In addition, the gripper unit 400 and the pipetting unit 500 can be movable independently of one another in the vertical direction, i.e. in direction z.

The drives 316, 326 of the Y-rail and of the carriage member and drives 348, 358 of the gripper unit and pipetting unit are constructed as stepping motors. Home sensors 319 (see FIG. 1c), 329 (see FIG. 6) are provided (also for the drives 348, 358; not shown), in order to detect when the driven unit reaches a calibrated position. The stepping motors and home sensors are configured analogously to the description thereof for the gripper (FIG. 8, 9) and in relation to FIG. 16.

Pipetting Unit

Figure 7:
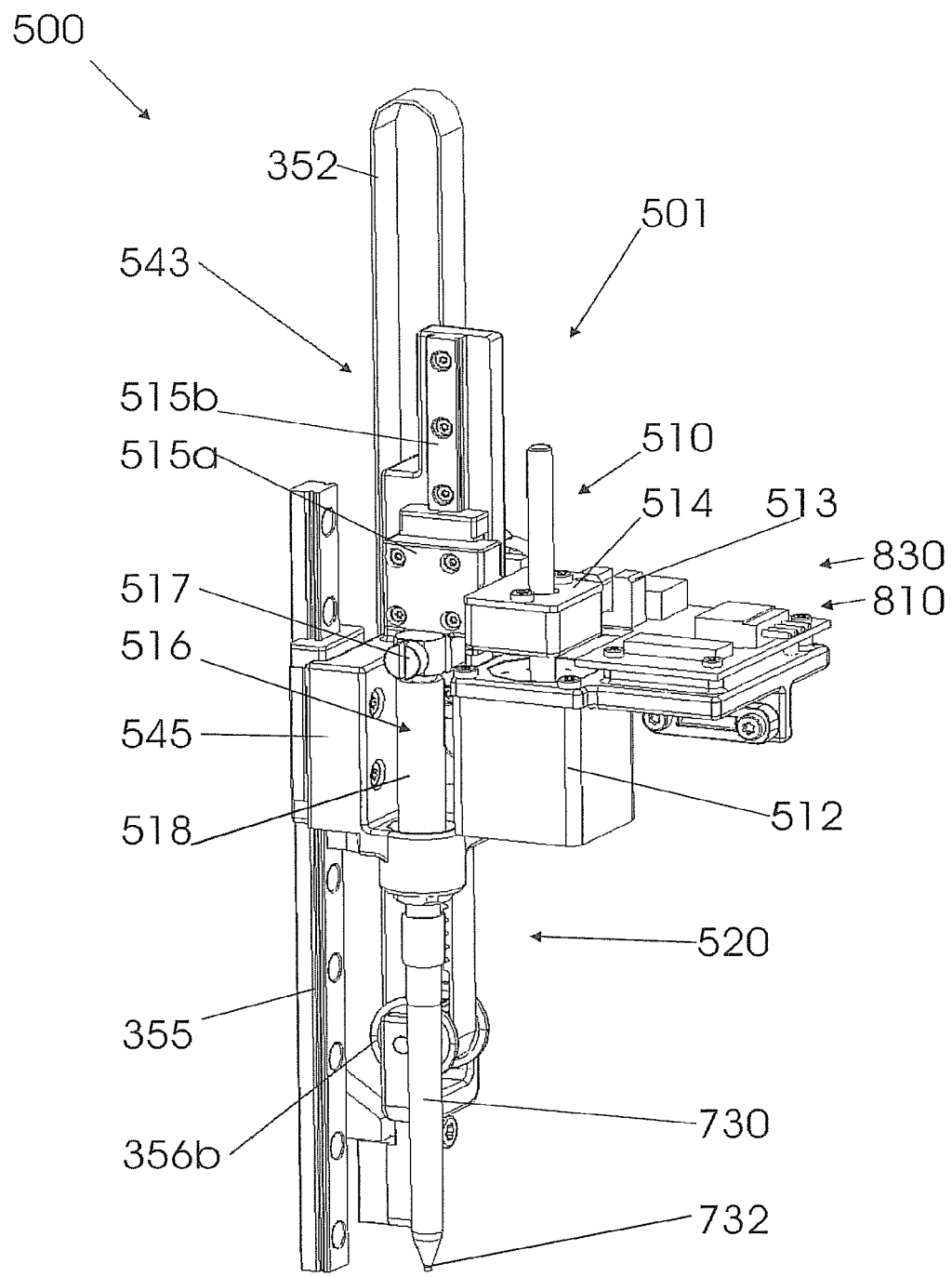
FIG. 7 shows a perspective view of the pipetting unit of FIG. 6.

FIG. 7 shows a perspective view of the pipetting unit 500. The pipetting unit comprises a pipetting member 501 which is movable along the rail 355 in direction z, as shown in connection with FIG. 6. For his purpose the pipetting member 501 comprises a carriage or a sliding or rolling element 545 which can slide along the rail 355 in direction z, and suspension means 350 for the movement of the pipetting member 501 in direction z. The suspension means 350 comprise a lifting belt 352, the rollers 356a, b and a drive 358 for driving the lifting belt 352. The lifting belt is attached to the pipetting member 501 by attachment means 543. The drive 358 is constructed analogously to the drive 316 of the Y-rail. The drive 358 is able to drive a movement of the sliding element 545 along the rail 355 and hence of the pipetting body 501 in direction z.

The pipetting unit 500 comprises a pipette tip holder 520 for pipette tips 730. In FIG. 7 a pipette tip 730 has been pushed onto the pipette tip holder 520. The pipette tips are pushed on removably, i.e. they can be removed from the pipette tip holder 520 or placed thereon. Further details of the construction of the pipette tip holder are described in EP Patent Application 06010976.6 which is hereby incorporated by reference in the present specification. It proposes a device for holding pipette tips with a coupling element having a longitudinal axis extending in the axial direction.

Above the pipette tip holder 520 is mounted a piston tube 518. The pipette tip holder 520 is constructed so that an exchange of gases or pressure is possible between the interior of the pipette tip 730 and that of the piston tube 518. The interior of the piston tube 518 and pipette tip 730 is sealed relative to the exterior so that the exchange of gases between the interior and the exterior is only possible through the pipette opening 732 of the pipette tip 730. A reduced pressure in the piston tube 518 relative to the exterior is transmitted to the pipette tip and causes gas or fluid to be sucked through the pipette opening 732 into the interior of the pipette tip 730. Excess pressure in the piston tube 518 analogously causes gas or fluid to be forced out through the pipette opening 732 out of the inside of the pipette tip 730.

In order to generate reduced pressure or excess pressure the pipetting unit 500 comprises a piston system 510. The piston system comprises a drive 512 and a piston carriage 515a which is movable along a piston rail 515b in direction z. The piston system further comprises a transmission system 514 for transmitting a rotary movement of the drive 512 into a lifting movement of the piston carriage 515a. The transmission system 514 is constructed as a worm gear. The piston system further comprises a piston 516 which is attached to the piston carriage 515a by a fixing 517. The piston 516 is thus arranged in the piston tube 518 such that it seals it off in gastight manner.

The piston system further comprises a home sensor 513 for detecting a calibrated position of the piston carriage and hence of the piston. The home sensor is constructed analogously to the home sensor 428 of the gripper described below (see FIG. 9). In a preferred embodiment the drive 512 of the lifting element is a stepping motor. If a calibrated open state can be detected in this embodiment, each lifted state of the piston can be detected by counting the steps of the stepping motor starting from the calibrated open state. There is a fixed relationship between the stroke of the piston and the volume of the fluid drawn in or expelled:

The piston 516 and the piston tube 518 provide a syringe. It is advantageous that the pipette tip holder, which is described in the above-mentioned EP Patent Application 06010976.6, is attached directly to the syringe, in particular to the piston tube 518. This arrangement allows for a particularly compact design of the pipette unit 500.

If the pipette opening 732 is immersed in a liquid and the piston 516 is raised, the increase in the gas volume in the piston tube 518 generates reduced pressure inside the piston tube 518 and the pipette tip 730. This reduced pressure causes the fluid to be drawn up through the opening 732 into the pipette tip 730. The volume of liquid drawn up corresponds to the increase in the gas volume in the piston tube 518.

If the pipette tip 730 contains a liquid and if the piston 516 is held at a fixed height, the liquid is held in the pipette tip.

If the pipette tip 730 contains a liquid and if the piston 516 is lowered, the reduction in the gas volume in the piston tube 518 generates excess pressure inside the piston tube 518 and pipette tip 730. The excess pressure causes the liquid to be conveyed out through the opening 732 out of the pipette tip. The volume of liquid expelled corresponds to the reduced volume of gas in the piston tube 518.

Figure 12:
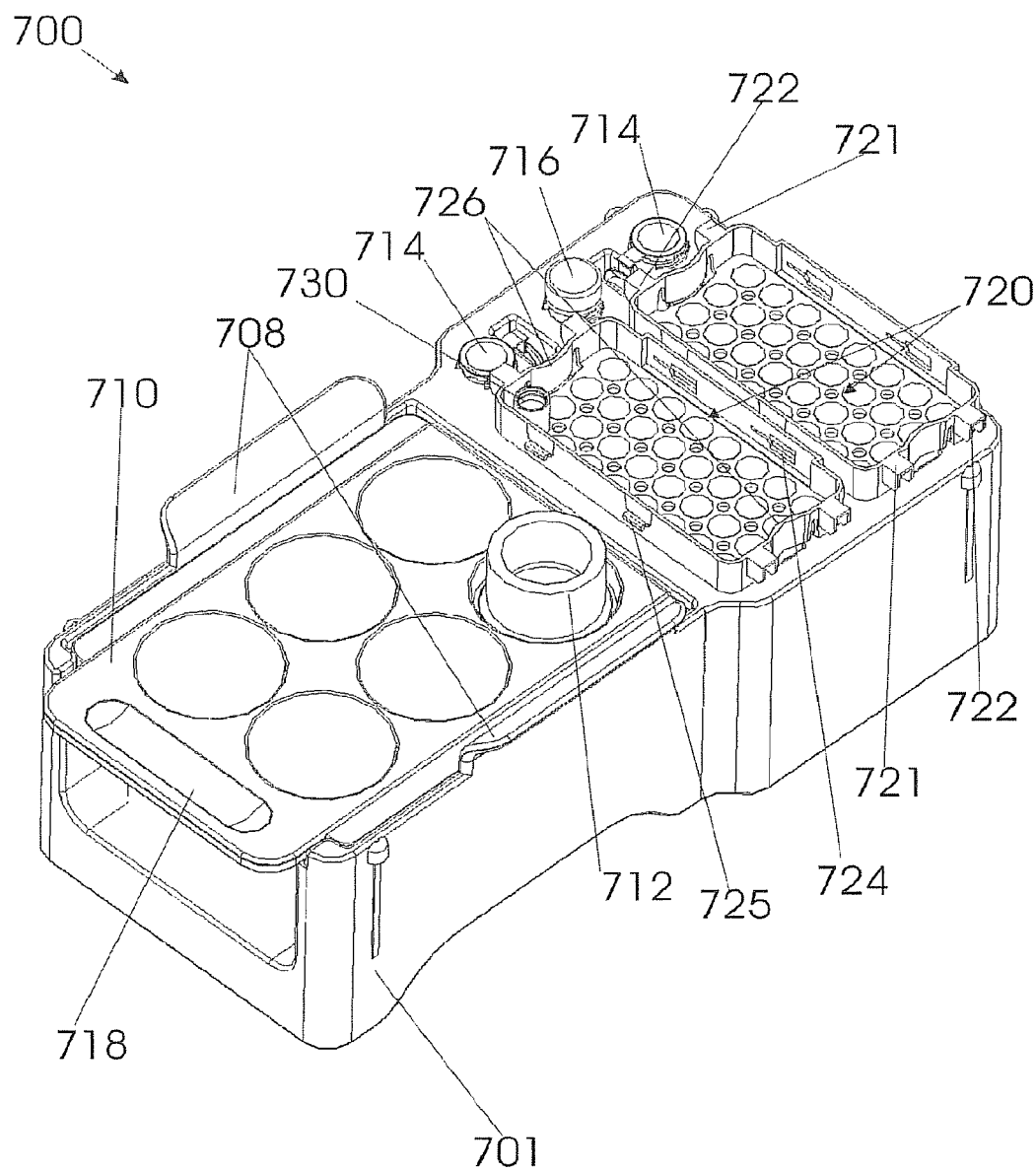
FIG. 12 shows a perspective view of a spent goods station for the spent materials in one embodiment.

In order to receive a pipette tip the pipetting member 501 can be moved with the pipette tip holder 520 over a suitable pipette tip 730 located in the pipette tip station 720 (see FIG. 1 and FIG. 12). The pipette member 501 is moved downwards so that the pipette tip holder 520 is pressed down into the pipette tip with a force of about 10-50 N. The pipette tip is then held therein, for example, by the compression of a seal around the outer circumferential surface of the pipette tip holder 520. A seal of this kind is described in EP Application 06010976.6, to which reference is made once again.

In order to discard the pipette tip 730 a disposal system 740 for waste may be provided as shown in plan view in FIG. 1b. The disposal system 740 comprises an opening 742 having an area 744 of large cross-section and an area 746 of small cross-section. The large cross-section of the area 744 is designed so that the pipette tip 730 can be pushed through it. The small cross-section of the area 746 is designed so that the pipette tip 730 cannot be pushed through it but the pipette tip holder 520 can be pushed through.

For disposal, the pipette unit 500 is moved so that the pipette tip holder 520 with the pipette tip 730 is above the area 744 of large cross-section. The pipette tip holder 520 with the pipette tip 730 is then lowered and the pipette tip is pushed into the opening 742. Then the pipette tip holder 520 with the pipette tip 730 is moved into the area 746 of small cross-section and the pipette tip holder 520 is withdrawn from the opening 742. The pipette tip 730 is held, for example, at its upper edge by an edge of the opening area 744 and thus remains below the opening 742. Once the pipette tip holder 520 has been removed completely from the opening, the pipette tip 730 detaches itself from it and drops into a container for used pipette tips provided underneath the opening 742.

The entire pipetting procedure will now be described. For pipetting, the pipette unit first of all picks up a pipette tip as described above. The pipette tip 730 picked up is then moved with the pipette body 501 over the container holding the liquid which is to be drawn up and is lowered into it.

It is advantageous during pipetting if the fill level of the container is known or is determined before the pipette tip 730 is lowered into it. This can be done using one of the methods of measuring fill level described below, e.g. using an ultrasound unit 830. Then the pipette tip 730 can be lowered generally, independently of the embodiment described, into the vessel depending on the fill level. This has the advantage, for example, that the dependency can be selected so as to substantially avoid the formation of droplets on the pipette tip.

Then a desired quantity of liquid is sucked into the pipette tip 730, the pipette tip 730 is moved over the target vessel and a desired quantity of the liquid is released from the pipette tip into the target vessel. If contamination of the pipette tip with the liquid in the target vessel is to be avoided, it is advantageous if the pipette tip is at a height above the target vessel which rules out contact with the liquid in the target vessel or with the wall or edge of the target vessel.

Basically, it is advantageous to change the pipette tip 730 to prevent contamination as otherwise there would be the risk of contamination or cross-contamination of the samples. For this purpose the pipette tip is discarded in the waste disposal station 740, as described above, and a new pipette tip is picked up as described above.

Gripper Unit

FIG. 8 shows a perspective view of the gripper 400. The gripper comprises a gripper member 401 which is movable, as shown in FIG. 6, along the rail 345 in direction Z. For this purpose the gripper member 401 comprises a carriage 445 for a rail 345, and suspension means 340 with lifting belt 342, rollers 346*a*, *b* and a drive 348 analogously to corresponding elements of the pipetting unit 500 (see the description of FIG. 7).

The gripper unit 400 comprises a gripper 410 for gripping the vessel 160. A detailed view of the gripper is shown in FIG. 9. The gripper comprises a rigid gripper housing. The gripper further comprises two gripping arms 416*a*, 416*b*. The gripping arms are each suspended from a spindle 426*a*, 426*b* in the gripper housing 412 and can be pivoted about their respective spindles. When the gripping arms are pivoted in a direction of closure the two arms 416*a*, 416*b* move together in a gripping area for the vessel and are thus able to grip the vessel 160 at its collar 168. In order to grip the vessel at its collar 168, recesses 417*a*, *b* which fit the collar 168 are provided in the respective gripping area of the gripping arms 416*a*, *b*.

For gripping the vessel 160 a drive 420 is provided. The drive drives a stroke of a lifting element 422. The stroke of the lifting element presses the two upper limbs of the gripping element apart so that the lower limbs, i.e. the limbs located on the other side of the spindles 426*a*, *b* from the upper limbs, are pressed together. The lower limbs contain the gripping area for the vessel. Thus the movement described is a movement in the direction of closure and the compression of the lower limbs enables the vessel 160 to be gripped.

For releasing the vessel 160 the drive 420 is able to move the lifting element 422 in an opposite direction, i.e. upwards in FIG. 9. In this way the two upper limbs of the arms 416*a*, 416*b* are pressed less far apart by the lifting element 422. As a result the spring or the elastic element 424 is able to press the two upper limbs further together and thus the two lower limbs further apart. In this way the gripper is moved in the direction of opening and the vessel is released.

In the Figure, the elastic element 424 is shown as a compression spring in a lower limb area of the gripping arms 416*a*, 416*b*. However, alternative embodiments are possible in which, for example, the spring takes the form of an elastic tension element in an upper limb area. Care must be taken to ensure that the elastic tension element does not collide undesirably with the lifting element 422. This is possible for example by making the tension element in the form of an elastic ring which spans the two upper limbs.

For detecting the state of opening of the gripper, the gripper 410 also comprises a home sensor 428 which delivers a sensor signal containing information as to whether the gripper is open or closed. For this purpose the home sensor 428 may for example contain a light beam the optical path of which is interrupted or not interrupted by a limb of the gripper depending on the state of the gripper. In this way a calibrated open state can be detected in which the home sensor changes its state, i.e. wherein for example the optical path of the light beam changes between the pass-through state and the interrupted state. In one possible embodiment the calibrated open state is for example the open state at which the gripper is opened to its maximum extent.

Figure 16:
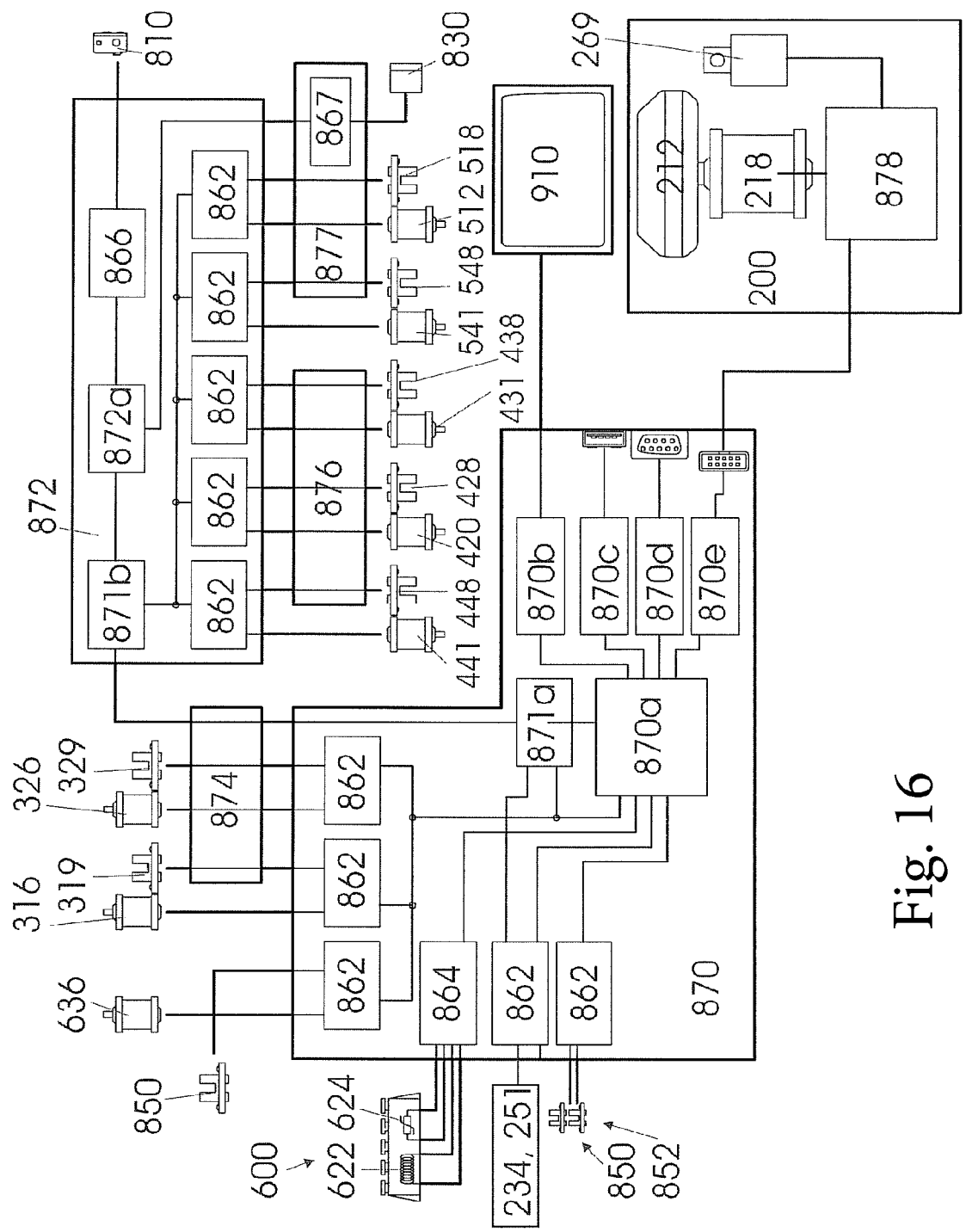
FIG. 16 shows a detailed diagrammatic representation of the sensory functions and control functions of one embodiment.

In a preferred embodiment the drive 420 of the lifting element is a stepping motor. If a calibrated open state can be detected in this embodiment, each open state of the gripper can be detected by counting the steps of the stepping motor starting from the calibrated open state. Other home sensors as shown in FIG. 16, for example, have an analogous function.

The gripper 410 further comprises a lid holder 414. The lid holder 414 is rigidly connected to the gripper housing 412. The lid holder 414 provides a stop for a lid 166 of the vessel. The lid 166 is pressed against the stop by the elastic force of a connecting element 164 which connects the lid 166 to the vessel 160 and thus positions or holds it in a fixed position. The gripping arms 416*a* further comprises a recess designed so that the connecting member 164 can extend through this recess. By means of this recess and the lid holder 414 it is possible to orient the vessel 160 relative to the gripper 410. However, the gripper may also grip a vessel 160 which does not contain a lid 166. In such a case no orientation is provided.

Referring once again to FIG. 8 the gripper 410 is rotatably mounted about a spindle 436*a*. The gripper 410 can be rotated about the spindle 436*a* by the rotary device 430. The rotary device 430 comprises a rotary drive 431, a drive gear 434, a further gear 436 and a home sensor 438. The rotary drive 431 is arranged so as to drive the drive gear 434. The drive gear 434 engages with the other gear 436. The gripper 410 is fixedly connected to the other gear 436 and is rotatable together with it about the rotation spindle 326*a*.

The rotary drive 431 is preferably constructed as a stepping motor so that a desired angle of the gripper 410 can be adjusted about the rotation axis 436*a*. The home sensor 438 supplies information as to whether the gripper 410 has been rotated into its original or calibrated position and thus constitutes a calibration point for controlling the stepping motor 431. The function of the calibration point is analogous to the function of the calibrated open state of the gripping arms 416*a*, *b* described above.

The gripper 400 is preferably constructed so that it can be rotated by the rotary device 430 of the gripper 410 through at least 120°.

The gripper 400 further comprises a positioning device 450 for a vessel holder 120 of the centrifuge 200. The positioning device 450 comprises a position spike 452. The positioning spike is constructed so that it can engage in a corresponding positioning opening 124 of a vessel holder 120. More generally, a positioning element 452 is constructed so that it can engage in a positioning counter-element 124 of the vessel holder 120 or interact therewith, e.g. by electromagnetic force. A vessel holder of this kind with positioning opening for a positioning spike is shown in FIG. 10, for example. This engagement ensures that the gripper member 401 is in a defined position in relation to the vessel holder 120.

The positioning device further comprises a positioning member 451 connected to the positioning spike 452. The positioning member 451 is movable along a positioning rail 456 independently of the grippe member 401 in direction Z. For this purpose the positioning member 451 is connected to a positioning carriage 457 which can slide along the positioning rail 456 in direction Z. In addition, the positioning member is connected to the gripper member 401 by a positioning spring 458 using fixings 458*a*, *b*. The positioning spring 458 provides a resetting force for the movement of the positioning member 451 relative to the gripper member 401. The positioning spring ensures that during the gripping of the vessel a sufficient force is applied by the positioning spike 452 to the positioning counter-element 124 so that the engagement between these two elements is ensured. Preferably the force is between 1 and 10 N, preferably between 1 and 5 N.

Independently of the embodiment shown, the lifting range of the spring (i.e. the height interval of the gripper member 401 in the direction z relative to the vessel holder 120 in which the positioning spring 458 presses the positioning element 452 onto the positioning counter-element 124) is such that it meets the requirements during the removal or insertion of a vessel 160 from or into a vessel holder 120. For example, it is advantageous if the lifting range is selected so that engagement between the positioning element 452 and positioning counter-element 124 can take place throughout the entire phase of removal or insertion of a vessel 160 out of or into a holding position, during which the vessel is in contact with the vessel holder or has not been fully removed from the vessel holder or is only partly inserted.

The gripper 410 is suitable, for example, for gripping the following vessels for biological fluids:
- spin tube 160, Eppendorf tube 170 or similar vessels without lids: these vessels are gripped from the outside by the gripping arms 416a, 416b. Optionally, one or more recesses 417a, 417b engage in a collar of the vessels.
- spin tube 160, Eppendorf tube 170 with lids 166, 176; analogously to the vessels without lids and in addition the optional lid holder 414 secures the lids 166, 176 as described above.

A vessel for biological fluids is defined here as a component for receiving such a fluid and which comes into contact with this fluid.

Additionally, the gripper 410 and a vessel holder 120 can be configured so that the gripper is able to grip the vessel holder. For this purpose a portion of the vessel holder is designed to grip by means of the gripper. For example, in contrast to the vessel holder shown in FIG. 10, a holding position 150 may be equipped with a collar such that the gripper is able to grip it in the same manner as a vessel. The vessel holder meanwhile is preferably designed so that an optional lid holder 414 does not interfere with the gripping. The lid holder may also be used, with a suitable configuration of vessel holder, to define the orientation of the vessel holder, e.g. an angle of rotation about an axis defined by the holding position 150.

The gripper is suitable for placing a vessel 160 in another vessel 170. This insertion is carried out analogously to the placing of the vessel 160 in a holding position 130, 150. Preferably, the other vessel 170 is in a holding position 140 of the vessel holder 120. Preferably the vessel holder 120 is located in a centrifuge 200.

The gripper is suitable for removing a vessel 160 from another vessel 170. The removal is carried out analogously to the removal of the vessel 160 from a holding position 130, 150. Preferably the further vessel 170 is located in a holding position 140 of the vessel holder 120. Preferably the vessel holder 120 is located in a centrifuge 200. Additionally it is advantageous to provide an apparatus for fixing the further vessel 170 in the holding position 140 during the removal operation. Such an apparatus may take the form of a pressing element (not shown), for example, which makes contact with the further vessel 170 on an upper side or on an edge of the vessel and presses it downwards. Such a pressing element can be pre-tensioned by means of a spring, for example, analogously to the positioning element 452 or may be formed integrally with the positioning element 452.

As described above, the drives 420, 431, 441 of the gripper are designed as stepping motors. Home sensors 428, 438 and 448 are provided for detecting when the driven unit reaches a calibrated position. By counting the steps of the stepping motor it is thus possible to detect every position of the driven unit starting from the calibrated position. The home sensors 428, 438, 448 are designed as light beams. When the calibrated position is reached the optical path of the light beam is broken.

The home sensors may alternatively also be designed as light beams in which, when the calibrated position is reached, the optical path of the light beam is opened up, or they may be constructed as contact sensors or other sensors.

Heater/Agitator

Figure 13:
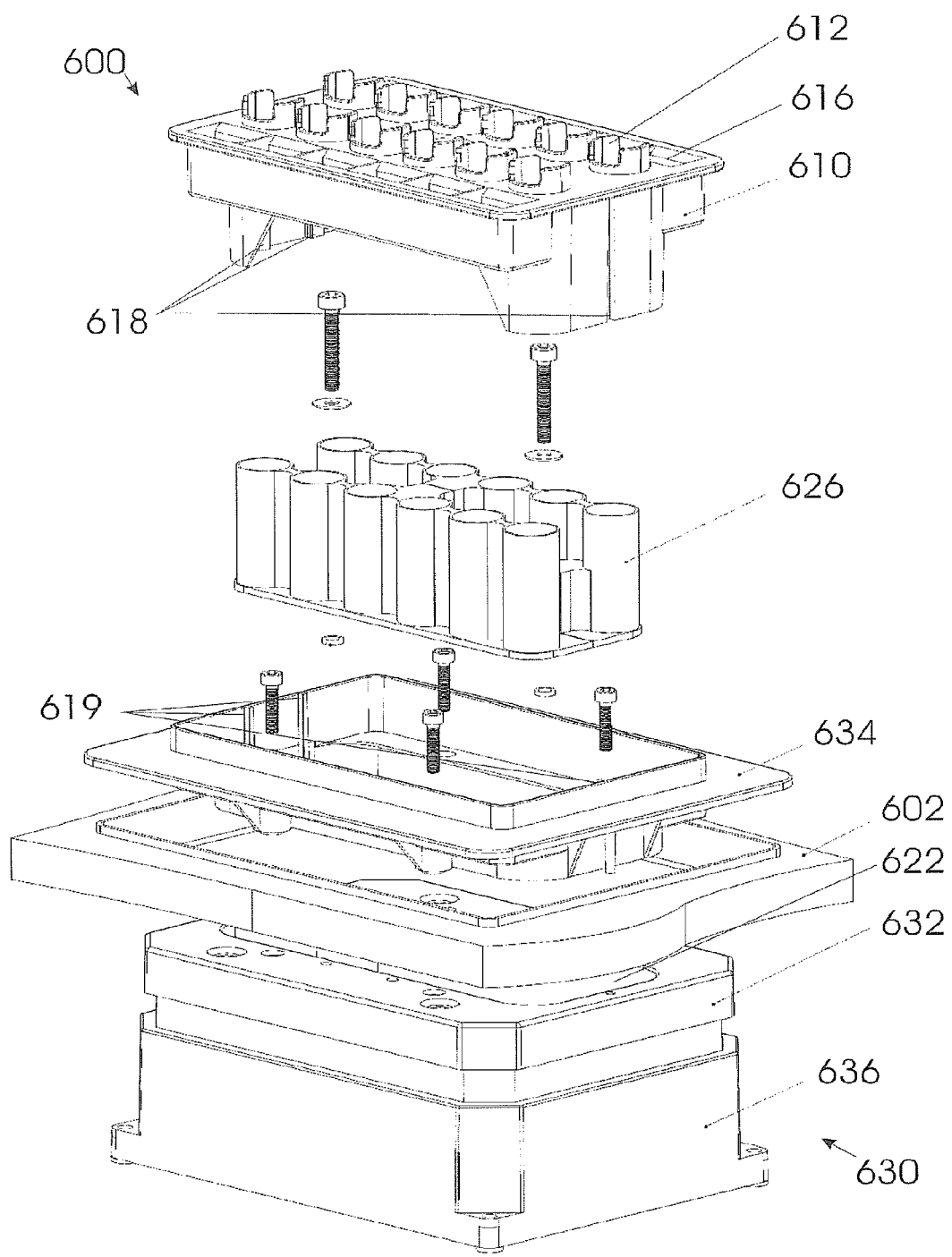
FIG. 13 shows a perspective view of a unit for heating a shaking one embodiment.
Figure 14A:
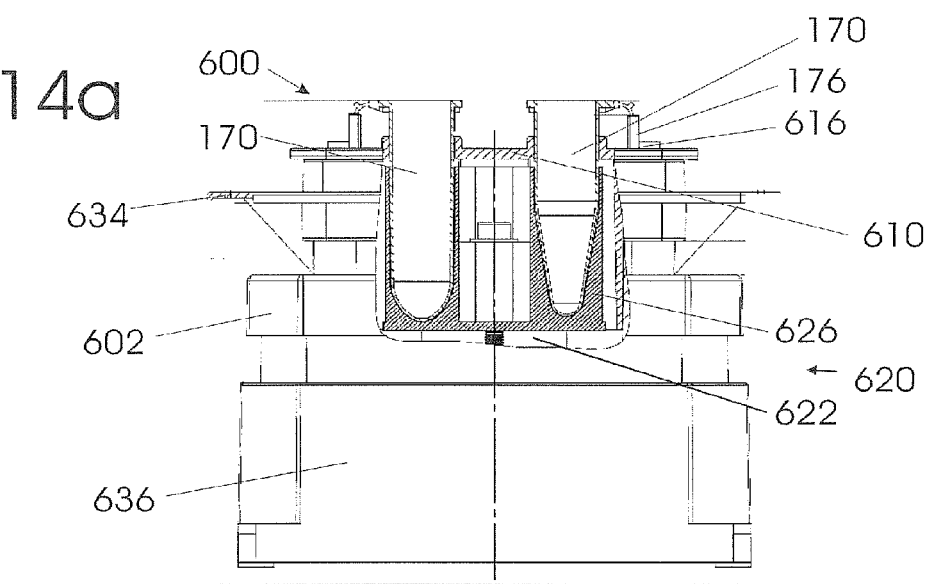
FIGS. 14a, b show a side view and top view, respectively, of a unit for heating and shaking one embodiment.

FIGS. 13 and 14 show representations of a unit 600 for heating and agitating samples or liquids. Such a unit may be used for example to carry out the lysing steps of a procedure. It may also be used for other procedural steps in which the sample has to be heated and/or agitated. At the same time the unit provides defined holding positions for the biological material. Thus the unit 600 for heating and agitating may also serve as a sample holder in the apparatus.

The unit 600 for heating and agitating is equipped, as shown in FIG. 13, with an insert 602 for the working platform which is provided for the height of the working platform. The unit 600 further contains a vessel carrier 610 with 12 vessel holding positions 612. The vessel carrier is adapted to the vessel which is to be held and can be inserted in the unit 600 by hand. If a number of other types of vessels are used, different types of vessel carriers may be provided. The particular vessel carrier which is suitable for a given procedure can then be placed in the unit 600. For easier classification in this case the vessel carrier is provided with numbering (see FIG. 14b in which the vessel carrier bears the number "2").

The vessel carrier 610 shown is designed for 12 reaction vessels (e.g. Eppendorf cubes or other vessels) with an optional lid, arranged in two rows of six vessels. As shown in cross-section in FIG. 14a, one row, i.e. six of the holding positions, is designed for a 1.5 ml format and the other row for a 2 ml format. The vessel carrier 610 has lid holding positions 616 for receiving the lids of the reaction vessels. The lid holding positions 616 may also take the form of slots, grooves or pockets, for example. The vessel carrier 610 can be inserted and removed together with the vessels held therein or samples contained therein. As a result the vessel carrier 610 can be loaded outside the apparatus. The vessel carrier may be constructed so that the vessels can be put in and taken out using one's bare hands. Alternatively it may be constructed so that the vessels can be inserted and removed using two laboratory gloves worn one over the other. It may also be constructed so that the vessels are inserted or removed by machine. In this case it is advantageous to design the lid holding positions 616, if provided, such that any lid holder 414 provided in the gripper 410 (see FIG. 9) can obtain access to the lids.

Figure 14B:
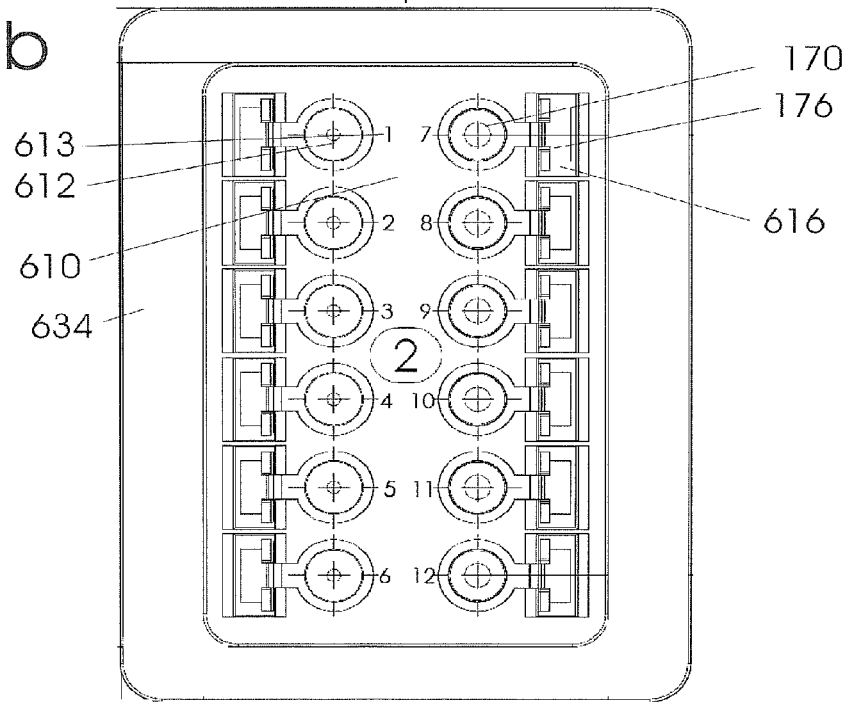

The vessel carrier 610 with 12 holding positions allows parallel processing of up to 12 different samples. If different samples are processed in parallel, it is advantageous, in order to avoid errors of allocation, if the vessel carrier can be clearly positioned. An apparatus for clear positioning is shown in FIG. 13, for example. In that apparatus, an orientation element 618, e.g. a rail, a recess or a slot is provided in the vessel carrier 610, and in the oscillating frame 634 a corresponding counter-element 619 is mounted such that the vessel carrier 610 can only be inserted in the oscillating frame 634 in one orientation. It is also advantageous to label the holding positions 612, e.g. by means of numbering 613, as shown in FIG. 14b, to avoid errors of allocation.

FIG. 13 also shows a heating system which comprises a heating element 622 and a heat transfer element 626. It increases the efficiency of the heating system if the heat transfer element 626 and the vessel carrier 610 are constructed so that the heat transfer element 626 makes direct contact with a vessel inserted in the vessel carrier 610, as shown in the embodiment of FIG. 13. Preferably the heat transfer element 626 has a heat conductivity of $\lambda > 30$ W/(m×K), most preferably $\lambda > 100$ W/(m×K).

The heat transfer element 626 is connected to the heater 600 by means of a screw connection, for example. If the vessel format changes, the element 626 can be changed. The heat transfer element 626 may alternatively also be constructed as part of the vessel carrier 610. This part of the vessel carrier can then comprise a thermally conductive material, e.g. a thermally conductive metal. Then when the vessel format changes only the vessel carrier 610 has to be changed.

In the embodiment shown the samples can be heated up to a temperature of 70° C. The heating time for the range from room temperature to 55° C. is about five minutes. The temperature accuracy required for a fluid in a vessel inserted in the vessel carrier 610 is +/−3 K (at 55° C.). The accuracy of temperature relates to different deviations from the target temperature of the fluid, e.g. as a result of deviations of the heater from the target temperature or a temperature difference inside the heater.

The heating element 626 is an electrical heating element with an output of about 100 W. Two separate heating circuits are provided therein. An advantageous subdivision of the power of the heating circuits is 70 W for the first heating circuit and 30 W for the second heating circuit.

The temperature regulation is capable of reading a temperature sensor, e.g. of the type PT1000. The heating is of such dimensions that the above-mentioned specifications regarding heat up time and temperature accuracy can be achieved. In the power circuit is a temperature safety device which is connected in series. This is not self-resetting. In the embodiment shown there is no active cooling.

The vessel carrier 610 may also be designed as a hand protector and as thermal insulation relative to the heating system 620. In this way the risk of burns to the user can be avoided or reduced. For example, the vessel carrier may have a handle part which has a heat conductivity of $\lambda < 5$ W/(m×K), more preferably $\lambda > 2$ W/(m×K).

In addition the vessel carrier 610 may be made of a thermally insulating material, e.g. ceramics or plastics. This has the additional advantage that the insulating properties attenuate the heat loss. The plastic used may be, for example, an autoclavable plastic which tolerates autoclaving for 20 minutes at 121° C.

The lysing step of a number of procedures requires the samples to be mechanically agitated. The embodiment of FIG. 13 comprises for this purpose an agitating system 630 which is integrated in the agitator/heater 600. The agitating system 630 comprises a drive block 636 which is attached to the apparatus 1, and an oscillating platform 632 which is movable and can be set to oscillate relative to the working platform 2 by the drive block 636. The heating system 620 described above and the vessel carrier 610 are mounted on the oscillating platform so that these elements are oscillated together with the oscillating platform.

The drive block 636 is described for example in the publication EP 1 201 297. It contains an electric drive for producing the agitating movement, comprising a cruciform arrangement of four separate coils. They are actuated as a stepping motor. However, the drive could also be any other desired electric drive. By the agitating movement is meant a reciprocating oscillating movement or a rotating movement about a centre of gravity or a combination of these or similar movements.

In the present embodiment the agitating system 630 is constructed as a rotary agitator. It allows amplitudes of the agitating movement of about 2 mm (peak to peak) and a maximum agitation period or rotation speed of more than 2000 rpm. The agitating movement is designed so that splashing and hence also cross-contamination between the samples are avoided as far as possible. For this reason the agitating movement takes place in one plane and has only a slight or no vertical component. In the agitating system the drive block 636 and the insert 602 for the working platform are fixed relative to the working platform; the other elements shown in FIG. 13 are agitated.

It is advantageous to provide a screen or shield for the sample vessels so that any splashes which might be produced during the agitating movements are caught and do not lead to cross-contamination. A shield can be obtained by a suitable design of the vessel carrier 610 with separating elements, e.g. separating walls. Separating elements of this kind are not shown in FIGS. 13 and 14. They may be produced as separating walls between adjacent vessel holding positions 612, integrated in the vessel holder 610. The separating walls may have a height which corresponds to at least the height of an upper edge of a vessel provided for the vessel holding positions 612 when the vessel is inserted in one of the vessel holding positions. Preferably the height of the separating wall is 3 to 7 mm higher than the height of the upper edge of the vessel. Alternatively, a screen may also be produced by means of another added part which can be placed on the vessel carrier 610 and provides separating elements. Preferably the separating elements are constructed so that it is still possible for the pipette unit 500 and/or the gripper 400 to gain access to the vessels.

It is also useful if the oscillating platform can be stopped in a defined resting position. For example, an electromagnet may be arranged in the agitator, which is capable of bringing the oscillating platform up to a stop and to position it against this stop in the defined resting position. Alternatively, the drive block may for example be provided with means for positioning in the defined resting position, e.g. with stepping motors having home sensors analogously to the drive of the gripper.

Other alternative embodiments for the heater/agitator 600 are possible. For example, only the heating element without the agitating system or only the agitating system without a heating element may be used if the other system in each case is not needed. Other functions may also be added. For example, cooling may be used, e.g. cooling by air, water or thermoelectric cooling. The cooling may also be combined with the cooling for 230, 250 of the centrifuge (see FIG. 3).

In addition, the arrangement of the holding positions 612 can be varied. FIGS. 13 and 14 show a matrix of 6×2 holding positions but other arrangements with n×m holding positions are also possible. Other possible alternative arrangements include for example a circular or hexagonal arrangement.

It is particularly advantageous to arrange the holding positions 612 of the vessel carrier 610 in such a way that they correspond to the arrangement of the holding positions in the centrifuge 200. The advantage of this is that it is particularly easy to coordinate the holding positions 612 of the vessel carrier 610 with the holding positions in the centrifuge. Particularly when the vessel carrier 610 is used as a sample holder for samples which are to be processed and when the centrifuge provides the processed samples, the risk of allocation errors is thus reduced.

The arrangement of the holding positions 612 is predetermined by the heat transfer element 626 in the embodiment shown in FIGS. 13 and 14. An alternative heating system using a liquid bath, for example, or a heat transfer element integrated in the vessel carrier may however also allow greater flexibility for the arrangement of the holding positions 612.

Consumable Goods Station

FIG. 12 shows a perspective view of the consumable goods station for consumable goods 700. The consumable goods station comprises a container station 710 for processing fluids, a pipette tip station 720 for pipette tips 730 and other holders for vessels 714, 716 with processing fluid.

The container station for processing fluid 710 comprises six holding positions for containers 712 with processing fluid. Different processing fluids may be used depending on the procedure. Examples of processing fluids used are buffer fluids for carrying out bind-wash-elute steps. The container station 710 further comprises a handle 718 for removing the station 710 from the consumable goods station for consumable goods 700. The handle 718 also lays down a clear orientation in which the container station 710 can be inserted in the station 700.

The consumable goods station 700 also comprises holding positions for containers 716, 714 which also contain processing fluid. These containers are analogous to the containers 712 but a provided for processing fluid which is used in only small amounts. The stations 714 and 716 differ in that the station 714 contains lid holders for a lid of the vessel. Thus, for example, Eppendorf tubes can also be used therein as vessels. By contrast the station 716 has no lid holders and can therefore only be used for vessels which have no lid or a screw closure.

Moreover, FIG. 12 shows the pipette tip station 720. It can be taken out of the consumable goods station for consumable goods. The pipette tip station 720 comprises a plurality of holding positions for pipette tips 730. The Figure shows two pipette tip stations 720 which may differ for example in the nature of the pipette tips which they hold. For example, the pipetting volume of the pipette tips in the two pipette tip stations may be different.

To allow recognition of the type of pipette tips the pipette tip station 720 has markings 721, 722. These markings are constructed as prominent elements which can be detected for example using an optical sensor. Each marking can carry one bit of information depending on whether the prominent element is present (1) or not present (0). Thus the elements 721, 722 carry two bits of information, i.e. information corresponding to a number between 1 and 4. Thus, in the embodiment shown, four different readable states can be distinguished. Three of these states are associated with different types of pipette tips; the fourth state indicates "no pipette tips present".

An alternative form of markings 721, 722 is possible. For example the marking could be provided by having parts of the container coated with a surface with different absorption or reflection of light. The nature of the marking may also be replaced for example by colour coding or by a magnetically readable coding. The number of coded bits in FIG. 12 shown is also variable. For example, one, three, four or another number of markings to be read could alternatively be provided.

The elements 721, 722 are designed to be point-symmetrical along the two short sides of the pipette tip stations. Consequently the marking is mounted to be proof against turning, i.e. it can be read regardless of which of the two possible orientations the pipette tip station 720 is occupying in the consumable goods station 700. FIG. 12 shows the type of marking corresponding to the bit sequence 1-1, i.e. both markings are present.

The pipette tip station 720 further comprises recesses 724 and strips 725. The strips 725 are designed so that they can be inserted in the recesses 724 and can thus join together two adjacent pipette tip stations 720, as shown in FIG. 12.

The pipette tip station 720 further comprises two opposing handle elements 726, by which it can be gripped for manual insertion and removal into or from the consumable goods station 700. During insertion, hook portions arranged underneath the handle elements 726 latch into the consumable goods station 700. For removal the hook elements can be released again by pressing the handle elements 726 together.

The consumable goods station 700 also comprises holders 708 which make it easy to remove the station from the working platform or insert it therein.

Waste Station

Underneath the waste disposal system 740 shown in FIG. 1 is a receiving container for waste, e.g. used pipette tips or columns or other vessels. A receiving container for waste fluids is optionally also provided, which can be reached through its own opening in the working platform (not shown).

The disposal of pipette tips is described with reference to FIG. 7. In order to dispose of any other waste it can be thrown through the opening 748 into the receiving container. For example, fluid used for the processing and no longer required can be released through the opening 748, e.g. pipetted out. In addition, vessels which are no longer required, e.g. filter vessels, can be disposed of through the opening 748.

Various receiving containers are preferably arranged together in a receiving apparatus for waste, either as separate containers or as a common container. The receiving apparatus may be constructed so that it can be taken out in one piece. For example, it may be in the form of a drawer which can be removed from underneath the display 910, as illustrated for the waste station 750 in FIG. 2a.

Control and Sensors

Figure 15:
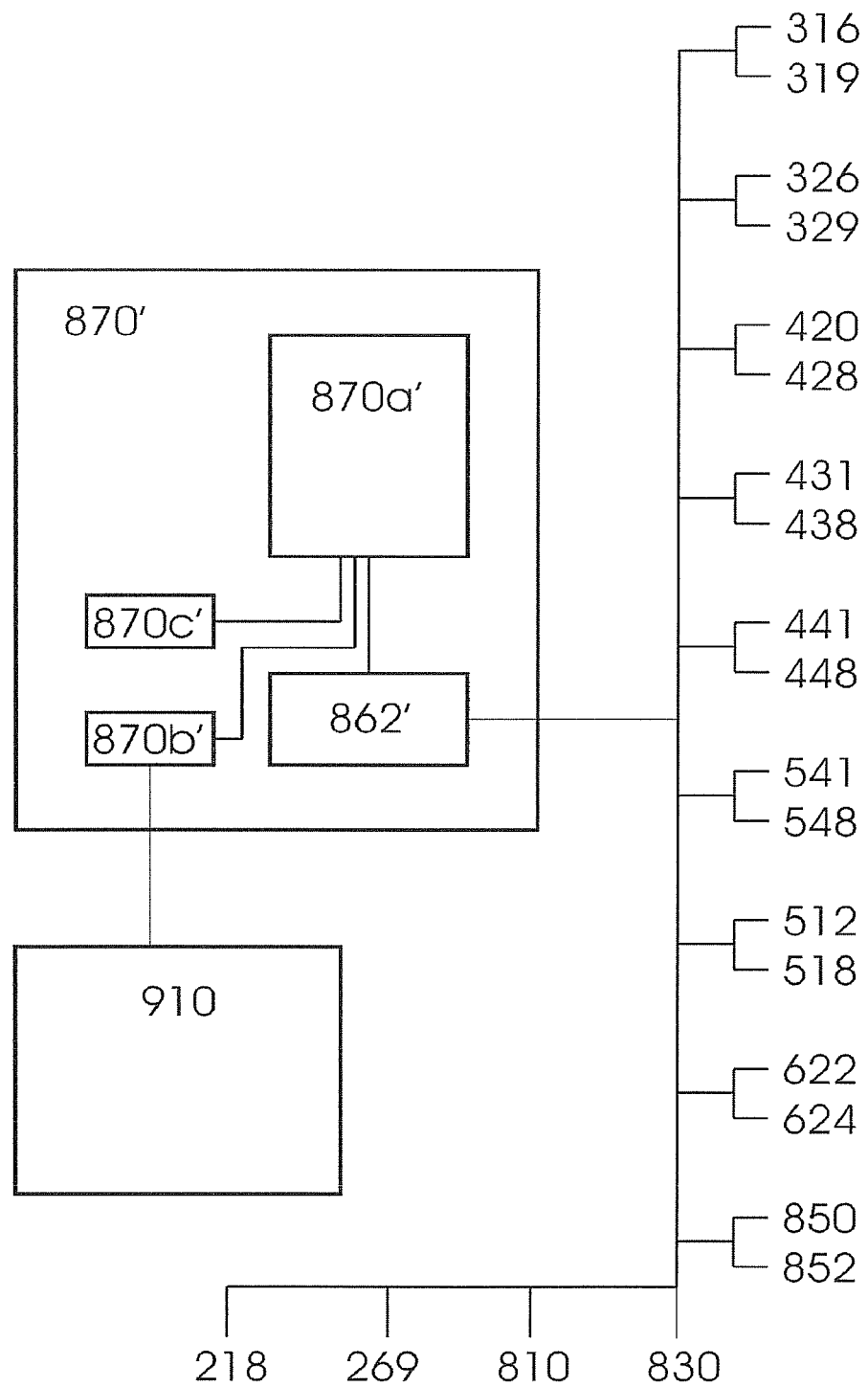
FIG. 15 shows a simple diagrammatic representation of the sensory functions and control functions of one embodiment.

FIG. 15 shows in a highly simplified schematic drawing the actuation of the apparatus for processing biological material. The control comprises a computer 870a', an input and output unit 870b', interfaces 870c' for communicating with external equipment, and interfaces 862' for controlling parts of the apparatus 1, e.g. motors, stepping motors, light beams, all these components being distributed over a board 870' or several boards.

The computer 870a' comprises a processor, working memory, operating system, preferably an embedded OS, and programs for running various control functions. In the working memory one or more protocols and parameters for running the protocols are stored, inter alia.

The input and out unit or user interface 870b' comprises a graphic controller for controlling a display 910 and an input interface, e.g. for receiving inputs using keys and/or the graphic display which can be in the form of a touch screen. The interface 870c' may for example be an Ethernet interface, a USB interface, an RS232 interface or some other conventional interface. The interface 870c' may also comprise a Web server.

The interfaces 862' comprise suitable control interfaces for various pieces of equipment to be controlled, such as stepping motors. The various controllable units shown in FIG. 15 are listed in the description of FIG. 16.

FIG. 16 shows by way of example a more detailed view of the control of an apparatus for processing biological material. The control unit of FIG. 16 may for example be used in the apparatus shown in FIG. 1c. In this case the main board 870 is accommodated in the main body of the apparatus, i.e. under the working platform 2. The Y-board 874 is arranged on the Y-rail 314. The carriage board 872 is arranged on the carriage 320. The gripper board 876 is arranged on the gripper unit 400, and the pipetting board 877 is arranged on the pipette unit 500. The centrifuge board 878 is arranged in the centrifuge unit 200. The above-mentioned boards correspond to the computer board 870' of FIG. 15. The main board 870 contains a main computer 870a, a graphic controller 870b and interfaces 870c, 870d, 870e. It also contains interfaces 862, 864 for various units of the apparatus which are to be controlled. It further contains an interface 871a for communicating with the carriage board 872 via a counter-interface 871b mounted on the carriage board.

The main computer 870a, the graphic interface 870b and the interfaces 870c-e correspond to the elements 870a', 870b' and 870c' shown in FIG. 15. The interfaces 870c-e having the following functions: interface 870c is a USB host interface which controls a USB master protocol. Thus the interface 870c allows new protocols to be loaded into the memory of the main computer 870a, for example through USB memory sticks. 870d denotes a serial interface (RS232) which can be used for maintenance purposes, for example. Alternatively it is possible to combine interfaces 870c and d and use any desired protocol, e.g. Ethernet or TCP/IP. The interface 870e (RS232) serves to communicate with the drive board 878 of the centrifuge.

The main computer 870a controls various interfaces 862 for stepping motors and light beams, either directly or via the interfaces 871a and 871b. The light beams generally act as home sensors for the stepping motors, i.e. there is a signal or a signal change in the sensor when the part to be driven by the stepping motor is located at a defined calibrated position, for example when a blocking part secured to the part which is to be driven breaks the light beam. Alternatively, the light beam may also be attached to the part which is to be moved. In this way the main computer 870a controls in particular the respective stepping motors and home sensors for the movement of the Y-rail in the X-rail 316, 319; for the movement of the carriage in the Y-rail 326, 329; for the movement of the gripper along the Z axis 441, 448; for the rotary movement of the gripper 420, 428; for the gripper movement of the gripper arms 431, 438; for the Z movement of the pipetting member 541, 548; and for the movement of the pipette piston drive 512. The main computer 870a also controls the movement of the motor for the heater/agitator 636. No home sensor is needed for this movement; an optional light beam 850 controllable by the interface may however be used for other purposes. Other light beams 850, 852 may be actuated via other interfaces, e.g. for consistency checks and other fault detection.

Moreover, the main computer controls the motors 234, 251 for ventilating the centrifuge and, via another interface 864, the heating element 622 and a temperature sensor 624 of the heater/agitator 600. The various interfaces for the different stepping motors are distributed over different boards 870, 872, 874.

In addition, the main computer 870a controls the drive electronics 878 of the centrifuge 200 via the interface 870e. The drive electronics 878 comprise essential control means for controlling the motor 218 of the centrifuge, for opening the centrifuge lid 240 by a suitable opening mechanism 260 (not shown) and the door lock 269, for example.

Also provided on the gripper board 872 is a separate computer 872a which communicates with the main computer 870a. The computer 872a serves to control a light sensor 810 (see also FIG. 7) which comprises an optical sensor 810a and a light source 810b, and an ultrasound unit 830 which comprises an ultrasound sensor 830a and an ultrasound source 830b, via corresponding interfaces 866, 867. The computer 872a further comprises drivers for controlling other stepping motors 441, 420, 431, 541, 512 and associated home sensors 448, 428, 438, 548, 518 via respective interfaces 862.

It is advantageous to equip the apparatus with sensors for detecting various states of the apparatus and its load. The sensors may for example be suitable for performing one or more of the following functions:

detecting pipette tips 730 in holding positions provided for them, e.g. in a container 720 for pipette tips;

detecting vessel holders 120 in positions provided for them in the centrifuge, i.e. to detect which places in the centrifuge are occupied by a vessel holder;

detecting columns 160 or vessels 170 or containers 712, 714, 716 in holding positions 130, 140, 150, 612 provided for this purpose, for example in a vessel holder 120 in the centrifuge 200 or in a heater/agitator 600 or in a container station 710;

adjusting the position of movable parts, e.g. the carriage 300 or the gripper 400 or the pipette unit 500 in order to compensate for any mechanical tolerances, for example;

detection of a zero or home position of a stepping motor;

measuring the fill level of liquid or other substances in a container 712, 714, 716 or vessel 160, 170;

detecting the nature and/or capacity of a vessel, e.g. a column 160 or a pipette tip 730.

checking the state of the equipment, e.g. the state of opening of lids such as the centrifuge lid 240 and the cowling of the apparatus, or the fill level of a waste container.

In particular it is advantageous to provide sensors which are suitable for performing several of the above-mentioned functions or other functions.

In a preferred embodiment one or more of the above-mentioned functions are performed by a light sensor 810 which can be attached to the carriage 300, the gripper 400 or the pipette unit 500. In the embodiment in FIG. 6, for example, the light sensor 810 is attached to the pipette unit. As a result the light sensor is movable over a part of the work surface 2 and adjustable in height.

Preferably the light sensor has a light frequency in the red or infrared range and has a laser or light cone as its method of radiation and/or is equipped with means for suppressing extraneous light by signal modulation and background fading by triangulation. Thus the light sensor is able to detect the presence of material with specific reflective properties, particularly with regard to diffuse reflection in the range of the light frequency of the light sensor, in a detection range of the light sensor.

By the recognition of items such as pipette tips, columns, vessel holders or other consumable materials is meant the recognition of their presence or absence in positions of the apparatus intended for the item in question or of their type.

A continuous movement of the light sensor may optionally be carried out for the recognition of a number of items. The sensor spot is then moved line by line over the various positions, for example. During the movement, measurements are carried out at the appropriate positions. If the mechanical tolerances between the positions for the items and the sensor are too great, the sensor position can first be adjusted, as described hereinafter. If the measurement is taken during movement, the measuring time has to be short, preferably in the region of a few milliseconds, possibly between 2 and 100 ms. Alternatively the movement of the sensor may be stopped for the detection process.

The movement of the sensor is selected so that its recognition range covers points or positions which are provided for a particular item, e.g. a pipette tip or a part of a pipette tip. If possible it should be ensured that the spot of the sensor strikes the feature which is to be recognised as accurately as possible during the measurement. In the case of pipette tips, for example, the spot should not make contact with the edge of the pipette tip but should fall as perpendicularly as possible onto the pipette tip.

The recognition range is preferably directed to a part of the item which has increased recognisability. Increased recognisability is defined as an increased signal difference between the state of "item present" and "item absent". The part having increased recognisability thus has reflection characteristics or some other signal behaviour which differs from the signal behaviour detected in the respective position when no item is present there. The light beam of the light sensor or some other radiation source preferably has a spot size which does not exceed 1.5 times, preferably 1 times or 0.7 times the area of the part with increased recognisability which is visible in the direction of the sensor. It is also preferable for the part with increased recognisability to be located at a defined height relative to the sensor.

In the case of pipette tips the part with increased recognisability may be a fleece which is mounted in the pipette tip. The fleece is usually white but may also be of some other colour. In the case of a vessel holder the part with increased recognisability may be part of the vessel holder which is provided for example with a particularly reflective material. In the case of columns (spin tubes) the part with increased recognisability may be a membrane, a filter membrane or a fliess. In the case of vessels, e.g. Eppendorf tubes, the part with increased recognisability may be a lid, e.g. a flip lid, or a hinge element or fixing element for the lid.

In the case of vessels or columns it is advantageous to bear in mind that they may also be filled with a liquid of any desired colour and to any desired liquid level. A felt in the columns may also have any desired colour. It is therefore preferable to use a light sensor with background fading for the detection process. This is trained to a first distance and then moved over the column or vessel at a second distance which is shorter than the first distance.

The methods described above and other methods are suitable for checking the loading of an apparatus such as the one shown in FIG. 1c. For example, the apparatus can be checked for completeness or consistency. Thus, for example, the loading of centrifuge 200 or of the sample holder in the heater/agitator 600 can be checked.

In order to check the loading of the apparatus it is advantageous to register, for different vessel holding positions, whether a vessel is present therein. Thus, the total number of vessels registered as present in the vessel holding positions can be determined and stored. For example, the total number of vessels in corresponding holding positions of vessel holders 120 in the centrifuge rotor 212 can thus be determined. From the total number of vessels and their positions it is possible for example to draw conclusions as to the number of vessel holders 120 in the centrifuge 200, or this may be registered separately. Depending on the total number of vessels registered as present in the vessel holding positions, a condition for the distribution of the vessels in the vessel holding positions is then determined. A condition may set out, for example, to minimise any imbalance in the loading of the centrifuge 200, as described hereinbefore. A check is then made as to whether the distribution of the vessels registered as present in the vessel holding positions complies with the condition laid down.

As described above, an optical sensor may also be used to register whether a vessel is present in the vessel holding positions. Thus, in addition, the optical sensor can register the number of sample vessels in sample vessel positions. The sample vessel position may be in the agitator/heater 600. Thus it is possible to check whether the number of sample vessels can be reconciled with the total number of vessels registered as present. An allocation can also be established which allocates to each sample vessel a vessel holding position, e.g. a vessel holding position in the centrifuge 200.

The allocation may for example assign to a sample vessel a vessel holding position in which a vessel registered as present, or it may assign to a sample vessel a group of vessel holding positions, in which a vessel is registered as present in at least one vessel holding position of the group. The allocation may also be established by issuing instructions to bring the sample vessel into a sample vessel position which is assigned to the vessel holding position. The sample vessel position may for example be allocated to the vessel holding position by a common name or be allocated to the vessel holding position by the fact that the arrangement of sample vessel positions in a sample vessel station corresponds to the arrangement of vessel holding positions in the centrifuge. The allocation may also be established by issuing a table which allocates the respective vessel holding position to a sample vessel position of the sample vessel.

The optical sensors also make it possible to check the loading of the apparatus with consumable goods. Such consumable goods may be vessels or biological substances. In particular they may be pipette tips, spin tubes, Eppendorf tubes and biological fluids, enzymes, and/or buffer fluids. For this purpose the number of prepared sample vessels with samples for processing is registered; depending on the number of sample vessels prepared, the necessary number and/or quantity of a consumable material for processing the samples is determined, in certain cases depending on the protocol; the number and/or quantity of consumable materials present in the apparatus is determined; and the number and/or quantity of consumable materials present in the apparatus is compared with the number and/or quantity of consumable materials required. By determining the actual state of the consumable materials references for the user are generated and displayed on the monitor 910 in order to produce the desired state.

To adjust the position of movable parts, one or more light sensors may also be used. Preferably the light sensor is used for detecting items for positioning. One or more light sensors are attached, in one possible embodiment, to a movable unit, e.g. the carriage 300 or the gripper 400 or the pipette unit 500 and are thus movable jointly with the unit.

During the movement of the unit the sensor is moved over a marking, the position of which is defined and known. In this way the position of the sensor and hence of the movable unit is determined.

The marking is an element which triggers a signal or a signal difference in the light sensor at a defined position of the light sensor. For example the marking may be formed by an edge on the operating surface 2, so that on one side of the edge the working surface 2 is within the detection range of the light sensor and on the other side it is not. Alternatively, the marking may be formed by a boundary between two surfaces with different diffuse reflection characteristics. To allow positioning in several directions, a number of edges or boundaries which extend in several directions (e.g. two directions perpendicular to each other) may be used. However, in the case of a sensor which is nonrotationally symmetrical in construction, e.g. a light sensor, the positioning in difference directions is typically of different degrees of accuracy. In this case a plurality of light sensors may be used, oriented in different directions, or a rotatable sensor may be used.

The position of the movable part relative to the position marking can be determined by counting the number of steps of a stepping motor. For example, the positioning may be designed to be redundant. The positioning may compensate mechanical tolerances.

Other sensors and markings may also be used for the positioning. For example, the sensor may be a magnetic coil, a camera or a light beam. The marking may then, for example, be an inductive conductor element, a colour marking or a blocking member for the light beam. For example, a light beam can be used to detect whether a part moved by a stepping motor is in a defined calibrated position (home position). A sensor 438 of this kind is described with reference to FIGS. 8 and 16.

Alternatively, the sensor may also be fixedly mounted and the position marking may be provided on the movable part. Referring to FIG. 1c, for example, a position marking may be provided on the centrifuge rotor 212 or on the vessel holder 120. Then the angle of rotation of the centrifuge rotor 212 can be positioned using the optical sensor.

In order to position the centrifuge rotor 212 or some other movable part with a positioning marking it is also possible to use a movable sensor. For example, a sensor may be used which is mounted on a sensor unit movable by a stepping motor, such as the pipette unit 500, for example. The positioning of the movable part is then carried out by the following steps:

Calibrating the position of the sensor unit movable by the stepping motor, i.e. establishing a home position of the sensor unit, e.g. by reading a fixed marking by means of the optical sensor. The marking may be provided on the working platform 2, for example.

Moving the sensor unit to a defined position in a movement area of the movable part (e.g. in the case of the centrifuge 200); the defined position is reached by counting the number of steps of the stepping motor of the sensor unit.

Moving the movable part, i.e. for example rotating the centrifuge rotor 212 until the optical sensor detects that a marking on the movable part, possible a marking which is co-rotatable with the centrifuge rotor, is in a defined relationship with the optical sensor.

Calculating the position of the movable part from the relationship defined.

Alternatively, the position of the movable part can also be detected by moving the sensor unit over the area of movement of the movable part. The position of the sensor unit meanwhile is updated by counting the number of steps of the stepping motor. As soon as the optical sensor has determined that a marking on the movable part is in a defined relationship to the optical sensor, the position of the movable part can be calculated from this defined relationship.

A fill level monitoring device for checking the fill level of vessels for biological materials, particularly liquids, is advantageous since without a fill level monitoring device of this kind the responsibility for providing the apparatus with sufficient amounts of buffer is left to the user. The risk of error and the work involved in checking by the user can thus be reduced.

It is also possible to check fill levels of other liquids or solid substances such as powders. In particular it is possible to ensure that the respective fill levels are within a given interval. The presence of such substances can also be checked using the methods described below.

Using a fill level monitoring device, for example, it is possible to ensure that the fill level of filter vessels (spin tubes) in the centrifuge is not too high. Consequently a warning can be given if the filter vessels are overfilled. In this way it is possible to prevent blockage of the filter vessels during centrifuging.

Various methods can be used to measure the fill level of a liquid. To avoid cross-contamination a contact free method is particularly advantageous. Some methods of contact free measurement of fill levels are described by way of example below:

In optical measurement of transit time, light impulses are fed into the container through an optical fibre. The reflected light from the surface of the liquid is detected by a photodiode. The time lag between the impulse and the echo is a measurement of the depth of the fill level.

During ultrasound measurement an ultrasound impulse is emitted by a piezo element, e.g. a piezo ceramic element. The impulse reflected by the surface of the liquid is received by the same piezo element after a time lag. The transit time measured is a measurement of the distance between the sensor and the surface of the liquid. It is preferable to use a sensor with a resolution of about +/−1 mm, preferably at a transmission frequency of about 250 kHz. It is also preferable to calibrate the system using a reference surface.

During capacitive measurement a capacitive sensor head is moved towards the surface of the liquid until a switching point of the sensor is reached. The switching point is reached when the capacitor electrodes of the sensor head are close to the surface.

During optical measurement of transmission the wavelength of a laser is selected so that the light of the laser is absorbed depending on the fill level. A wavelength in the region of about 1300 nm is advantageous, for example. The absorption then constitutes a measurement of the fill level.

In optical measurement of angles a laser beam is reflected by the surface of the liquid. The angle of reflection and hence the surface of the liquid are determined using an optical line sensor. In this process the surface of the substance is irradiated in the vessel by the laser or some other source of radiation; the radiation which is reflected or diffusively beamed back by the surface of the liquid (or of a solid substance) is measured by a radiometer; depending on the radiation measured by the radiometer the radiation source, the radiometer and the vessel are brought into a spatial relationship with one another (e.g. by tilting the radiation source), so that a first angle between a perpendicular to the surface of the substance and a first beam passing from the radiation source to the surface of the substance is substantially identical to a second angle between the perpendicular to the surface of the substance and a beam reflected by the first beam which passes from the surface of the substance to the radiometer; and then the height of the surface of the substance is determined as a function of the spatial relationship of the radiation source, radiometer and vessel.

The level of the surface of the substance is generally determined using the fact that the first and second angles are identical. The irradiation is typically carried out using a pencil beam with a pencil diameter of 3 mm. For angular measurement it is also advantageous to use a light sensor which is also used for other purposes, e.g. for positioning and/or for checking the load.

When a light sensor is used, particularly an optical reflected light sensor for optical angle measurement, the following error sources must be taken into consideration, in particular: first, there may be surface waves which can cause light to be reflected in all directions. This may lead to faulty signals over the entire range. Therefore, it is advantageous to carry out the determination over a sufficiently long period or area over several wave crests of the surface waves. In this way the surface waves are averaged out so that a signal maximum is obtained at an angle of reflection which largely corresponds to the angle of reflection of a smooth surface. It is also preferable to filter reflections from the walls and base of the vessel as otherwise these could falsify the measurement. This is possible if the shape of the vessel is known.

It is also preferably to take account of adhesive forces, preferably depending on the particular liquid the level of which is being investigated. Adhesive forces cause a lens-like surface to form at the walls inside the vessel. If this surface is not taken into account, this may lead to errors in the case of narrow vessels. To take account of the adhesive forces it is advantageous if the spot size is significantly below an internal vessel cross-section. Then the angle of reflection can be measured as a function of a horizontal position. By comparing the dependency with a model which takes account of adhesive forces the curvature of the surface can be determined and compensated. Alternatively, if the spot is small enough, it may also be directed to the centre of the vessel where the surface is substantially horizontal. For this purpose it is preferable for the area of the spot to be less than one tenth of the internal cross-section of the vessel.

In order to detect the nature and/or capacity of a vessel a marking can be read which is attached either to the vessel itself or to a container for the vessel. For example, such a marking may be in the form of the marking projections 721, 722 shown in FIG. 12. This marking can be read by means of a movable light sensor or with a light beam or some other sensor.

As a further example the size of the vessel may depend on the size of a grip portion of the vessel. In this case the size of the vessel during the gripping of the vessel can be determined by measuring the amplitude of the closing movement of a gripping arm.

As a further example the size of the vessel may depend on its length. In this case it is advantageous if the vessel is gripped by a gripper such that it is held vertically along its length and if the gripper is moved at a defined height above one or more light beams 852 (see FIG. 1a) with a horizontal beam path. Depending on the length of the vessel and the height of a particular light beam the beam path of the light beam may or may not be broken by the vessel. The length can be narrowed down or determined from the information as to whether the light beam has been broken or which light beam has been broken. If this is necessary to determine the length the gripper may also be moved several times over the light beam or beams at different heights. The gripper may also be positioned above the light beam and be moved in the vertical direction until the optical path is broken.

User Interface, Operating Concept

The operating concept of the apparatus is directed towards simple and intuitive operation. The user guide of the apparatus particularly contributes to this. It is designed so that as few as possible input steps are needed to carry out a procedure, these steps being as intuitive as possible, and that relevant information needed by the user is displayed in a form which is as easy to understand as possible. For example, a contribution to this is made by the fact that the settings of frequently used procedures can be stored and called up directly and input fields which seldom need modifying are typically bypassed.

The apparatus is essentially operated using a TFT touch screen. For example a touch screen with a resolution of 240×320 pixels may be used. Other operating elements such as keys and switches are optionally possible, e.g. for emergency off function or for the standalone operation of individual modules. The apparatus also comprises interfaces for digital data exchange in order to load or store protocols and parameters, for example, to transfer diagnosis data, run software updates or permit remote operation of the apparatus. FIG. 16 shows a USB interface 870c and an RS232 interface 870d for this and similar purposes.

Figure 17A:
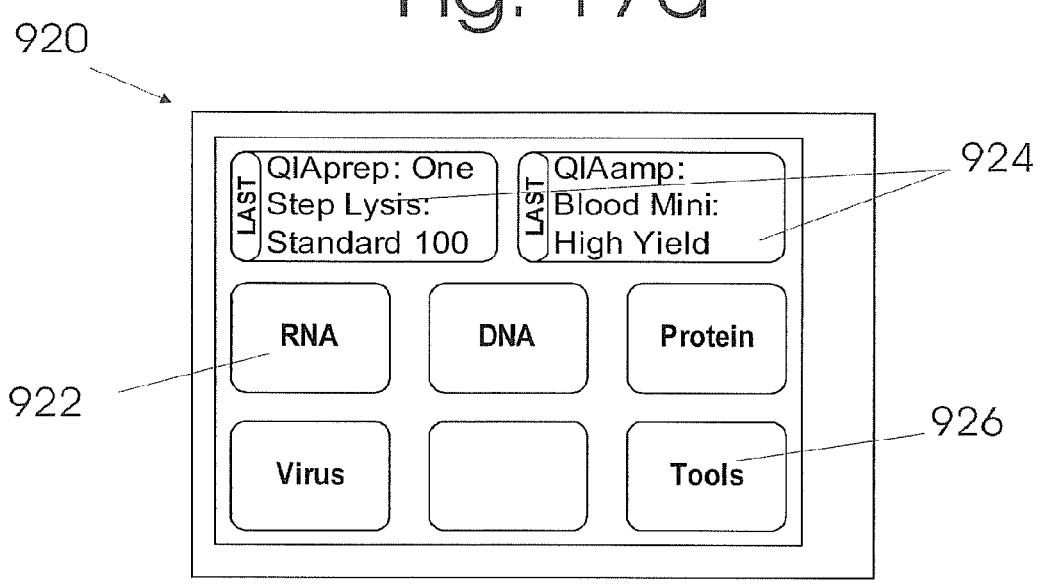
FIGS. 17a, b show picture screens for guiding the user of one embodiment.
Figure 17B:
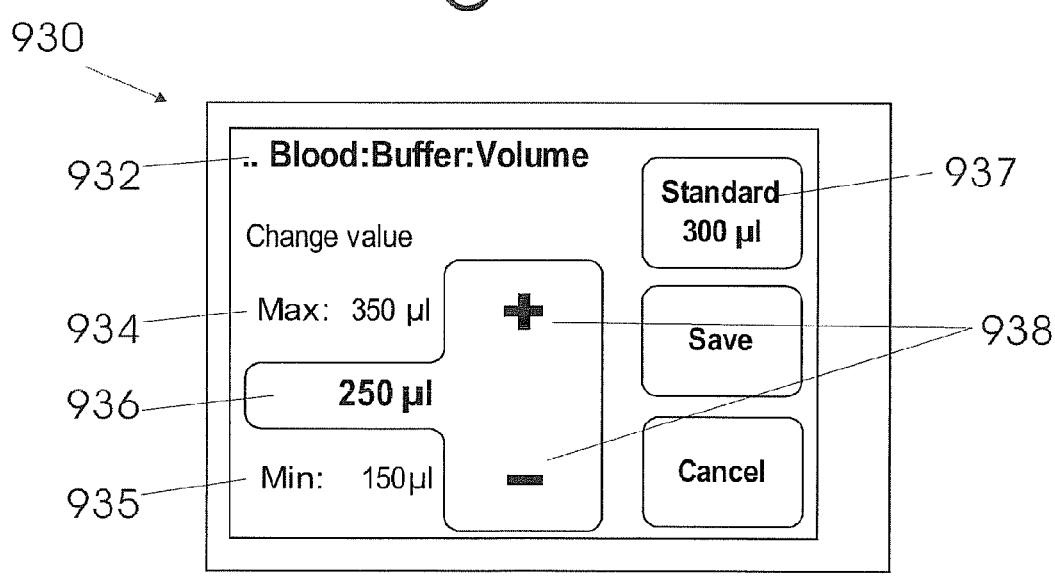

A typical screen design for the user guide shown in the display 910 is shown in FIG. 17b. The screen 930 shown has a heading 932, a value field and various other keys ("standard" 937; "save"; "cancel").

The heading 932 serves as an orientation for the current location in the user guide, e.g. in a menu. In the heading 932, excessively long texts are abbreviated. This is indicated by a series of dots. Depending on whether the left or right-hand side of the text is more important it is cut off on the right or left.

The value field is used to amend values, in this instance a buffer volume. It comprises an on/off control element 938. By pressing the "+" key of the control element 938 the value is increased and by pressing the "−" key it is reduced. The possible threshold values 934, 935 are shown. When a threshold value is reached the corresponding key of the control element 938 becomes inactive.

Analogously to the value field shown it is also possible to have a list field (not shown) for selecting an element from a fixed number of elements; e.g. for choosing a protocol from a number of protocols. Like the control element 938 the list field has arrow keys for selecting a desired element. The current element at any one time is shown in bold within a frame and in larger font. The list field also includes an action key which describes what is to happen with the selected element. The most likely action is carried out when the representation of the selected list element is pressed directly.

When the apparatus is used first, a start screen 920 is shown, as represented in FIG. 17a. The start screen 920 does not totally correspond to the screen in FIG. 17b described above. It contains two quick start keys 924, protocol keys 922 and a tools key 926 for accessing equipment settings and other functions. As soon as a key on the start screen is operated the user is directed to the corresponding menu.

The quick start keys 924 show the protocol which was started last (left-hand key) and the next-to-last protocol (right-hand key). More than two quick start keys may be provided. The caption of the quick start keys 924 varies once a protocol has been start. If a protocol has to be allocated to a quick start key the corresponding quick start key 924 can be operated for a long period.

Individual displayed parameters of the protocols can be varied. A protocol with adapted sets of parameters can be stored and then selected using a list field. The set of parameters can then be adapted using an options key.

Figure 18A:
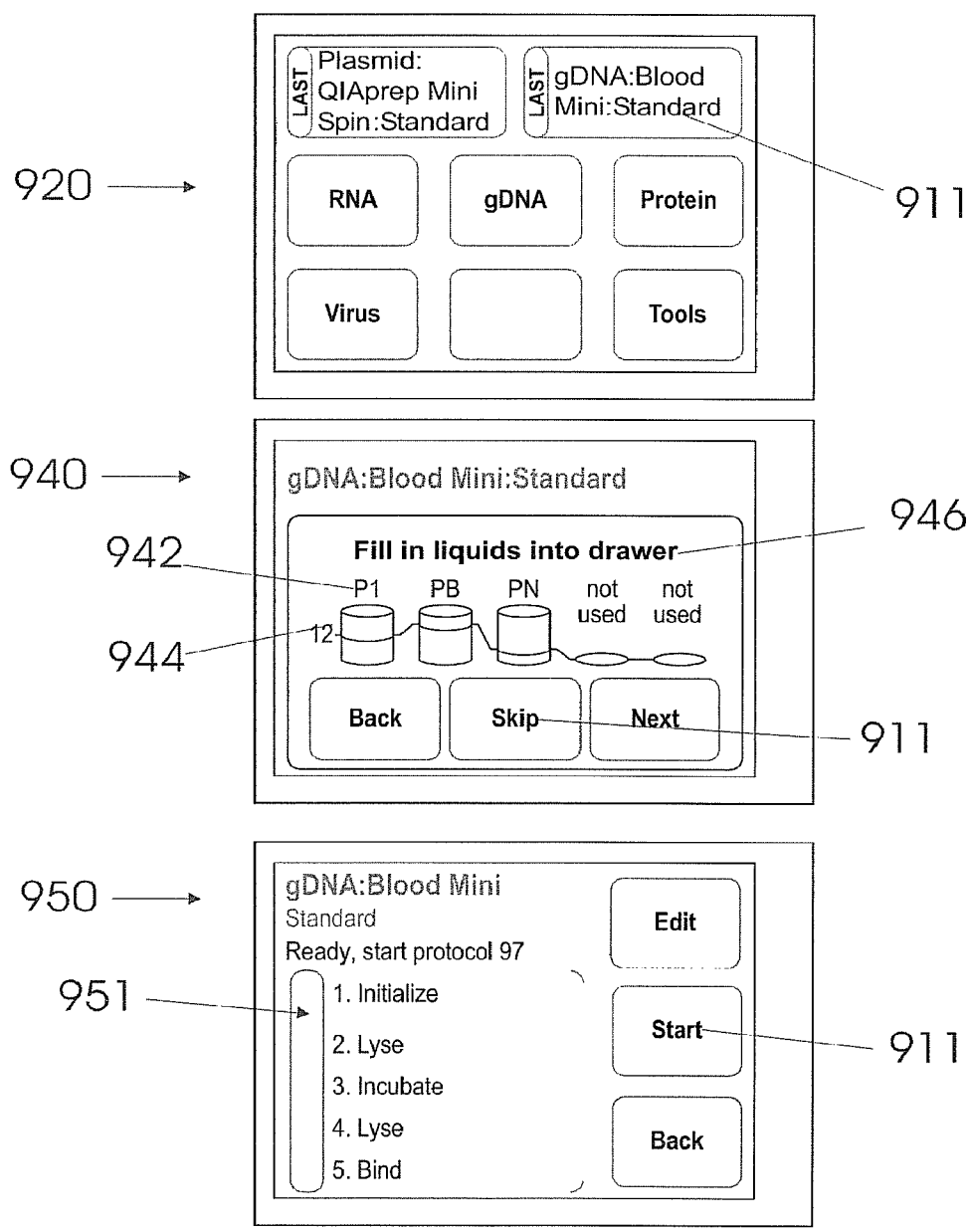
FIGS. 18a, b show picture screens of an embodiment for guiding the user to select, prepare and run a procedure.
Figure 18B:
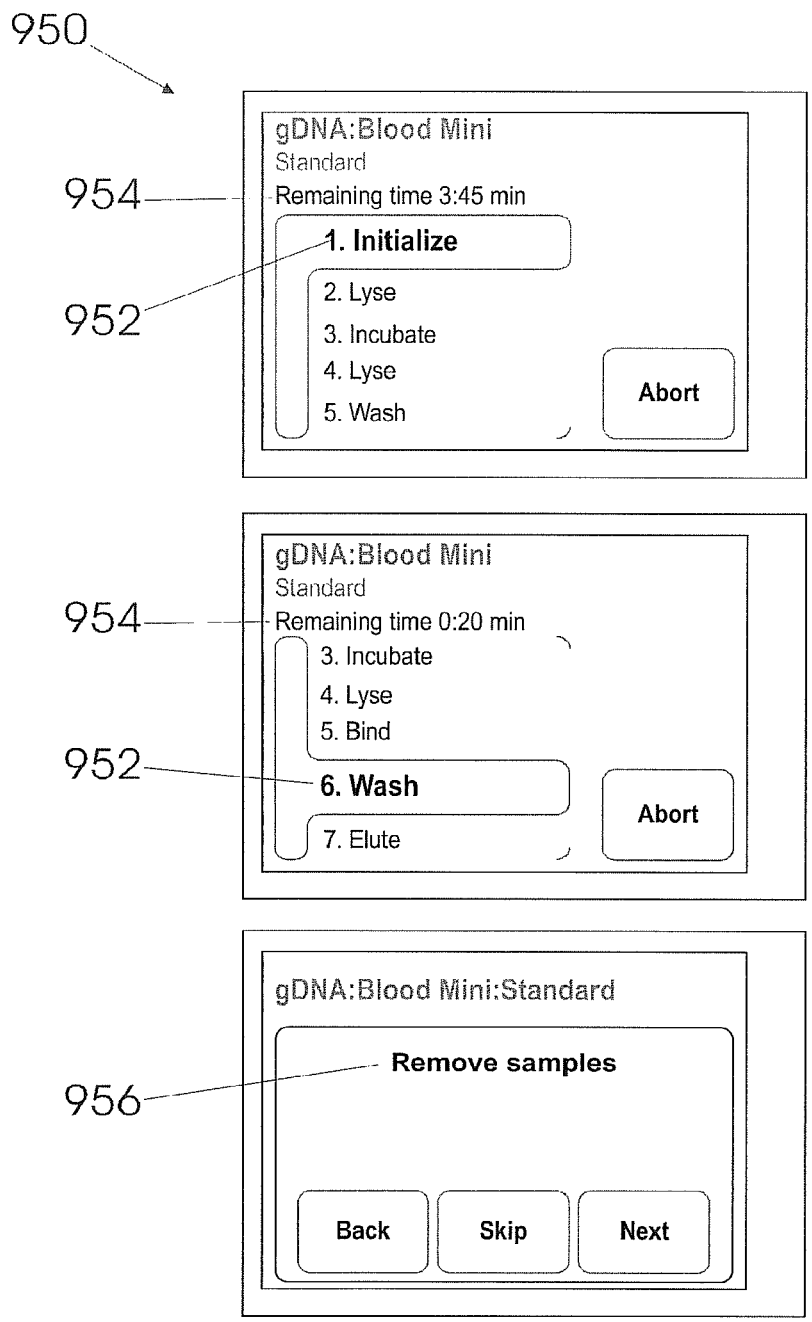

For example, FIGS. 18a and 18b show a typical operating procedure for running a protocol. The first screen 920 is the start screen shown in FIG. 17a. When the quick start key is pressed 911, one or more screens 940 appear with instructions 946 for loading the apparatus with consumable materials and other preparations for the protocol.

The screen 940 displayed shows the liquids and liquid levels 944 required for the specified protocol, for various positions 942 of the container 710 for buffer liquids. FIG. 18a shows an overview screen 940. Here the liquids are colour coded and the necessary liquid levels are displayed graphically. Detailed information on loading is obtained by pressing the key "next" (not shown). By pressing the "skip" key this part of the user guide is skipped.

As soon as the centrifuge lid is opened the user interface also displays instructions for loading the centrifuge (not shown).

In the example shown the "skip" key is pressed 911. The subsequent third screen 950 in FIG. 18a shows an overview of the protocol steps to be carried out. The steps are shown as elements of a progress bar 951. On the screen displayed the following protocol steps are shown: initialising, lysing, incubating, lysing, binding. Other steps which cannot be displayed for reasons of space are not shown, are shown at alternative times or indicated by an element such as dots, for example, (not shown), while the further steps can be indicated by touching the element.

Using the "edit" key it is possible to adapt variable parameters of the protocol, e.g. the type or quantity of buffer, double illusion, the starting volume, RNase treatment etc. Pressing the start key 911 causes the protocol to start up.

The screens 950 displayed while the protocol is running are shown in FIG. 18b. This shows the estimated time remaining 954 and the protocol step 952 which has actually run, in a progress display. The protocol can be stopped at any time but not continued again. The Interrupt key is not an emergency off button. Various processes are concluded before the final program end and the spindles return to their starting position.

Furthermore, the centrifuge and the shaker can be operated on their own, i.e. independently of protocols. These functions can be accessed for example using the tools menu 926 of the start screen in FIG. 17a or using a special key.

Various equipment settings can be selected after pressing the tools button 926 on the start screen (see FIG. 17a). A menu then appears containing the following setting options.
  using the centrifuge 200 independently of protocols;
  heating and/or shaking independently of protocols;
  maintenance, e.g. resetting of movable parts; opening or closing the centrifuge lid;
  settings, e.g. screen brightness, sound signals;
  system control, e.g. storing log files, equipment characteristics (serial number, specification, etc.), playing updates; and
  system settings, e.g. temperature, voltage, error messages, etc.

The order of the menu items may depend on the frequency of use: the more often a function is needed the further up it appears on the menu. Basically a "Standard" key is also available. This key sets standard values for a selected element.

The apparatus has a USB interface 870c configured as a USB master. With this data can be read from a USB memory stick and written thereon. The USB memory stick can thus act as a medium between a PC and the apparatus. Alternatively, another interface, such as Ethernet or RS232 may also be used and other functions such as a Web server may be carried out.

The following data may be exchanged with the USB memory stick using the USB interface:
  protocols (loading and storing individual protocols or a number of protocols simultaneously);
  securing equipment information (e.g. diagnosis information, log files with service data or error data, status files etc.); and
  updates of the firmware or software.

In addition, protocols and other files can be deleted (individual protocols or a number of protocols simultaneously). Protocols are protected as SPS algorithms and stored as xml files.

Each type of file (e.g. protocols to be load or stored, firmware, etc.) is associated in the index structure of the USB memory stick with an index showing the predetermined name. The transfer of file from or to the USB memory stick is carried out using a special assistant program which provides a menu of its own. The user has the choice of overwriting files already present on the target equipment or transferring only the files which are not already present.

Other service functions may be carried out if the apparatus is connected to a PC through the RS232 interface 870d which is equipped with special service software.

The operation is designed for the easiest possible use for the most common applications. These are usually the running of new protocols and the deleting of protocols.

Protocols

Partial steps which may be carried out when processing biological material in an apparatus having the partial modules described above will now be described with reference to a protocol by way of example. First, as shown in FIG. 18a, a desired protocol is looked up and optionally protocol parameters are selected. The apparatus then gives instructions 940 for loading the apparatus. The apparatus is loaded by hand in accordance with these instruction. Alternatively, it may be loaded automatically or partly automatically. In particular:
  the consumable goods station 701 (see FIG. 12) is loaded with consumable goods such as pipette tips 730 and containers containing buffer liquid 712, 714, 716;
  the centrifuge 200 is loaded with suitable vessel holders 120 and vessels 160, 170;
  the heater/agitator 600 is loaded with sample vessels 170. The samples to be processed are contained in the sample vessels 170.

Alternatively, the loading may be carried out for example by inserting a prepared station 701 or a vessel carrier 610 in the apparatus.

The loading is then checked by the apparatus for consistency and completeness. As described previously, the check may be carried out, for example, by means of a light sensor 810 which is movable over the working platform and/or by means of an ultrasound unit 830. Other process parameters (e.g. the number of samples to be processed from the number of sample vessels 170 detected) can also be derived from the check.

Then protocol steps are carried out for processing the samples. By way of example, the automated running of a protocol for purifying biomolecules from cells is described, comprising the steps of lysing, pelletting, binding, washing and eluting. The processing may also comprise other protocols as described for example in the publications "QIAGEN Bench Guide", the "QIAGEN Guide to Template Purification and DNA Sequencing" and the "QIAGEN QIAprep® Miniprep Handbook" (Second Edition, June 2005). Furthermore, the protocol steps carried out may include only some of the steps or may include other steps in addition to them or instead of them.

For the lysing step the sample material is manually transferred into the heater/agitator with the sample vessel or optionally by means of the gripper 400 or the pipette unit 500 is transferred into it. Buffer liquid is pipetted into the sample material. The same pipette tip may be used for all the samples, provided for example that the pipette tip is at a sufficient height to ensure that the pipette tip is not contaminated during the pipetting process.

The buffer liquid and the sample material are mixed by shaking the heater/agitator. The sample is optionally brought to a defined temperature by heating in the heater/agitator and kept at the temperature for a given time (incubation). Optionally, other buffer liquids are added. The desired biomolecules are now dissolved in the buffer liquid (lysate).

The lysate is then transferred into the centrifuge by pipetting, as described with reference to FIG. 7. A separate pipette tip is used for each sample and then discarded in the waste disposal station 740.

Optionally a pelletting step is then carried out. In this, the sample is centrifuged to achieve a better separation of the lysate and cell debris. The sample is transferred by pipetting into a vessel in the centrifuge. Such a vessel may for example be an Eppendorf vessel 170 held in a holding position 140 or a vessel 150 integral with a vessel holder 120 (cf. for example FIG. 11c). Alternatively the sample vessel 170 with the sample therein may be transferred by the gripper 400 into a holding position 140 in the centrifuge. Then the sample is centrifuged in the centrifuge 200 so that the cell debris collects mainly on the floor of the vessel. During the centrifuging the lid 240 of the centrifuge is closed by the lid control 260. It is then opened again to allow access to the interior of the centrifuge.

A binding step then follows. In this, the lysate is transferred by pipetting into a filter vessel 160 or into a vessel 160 containing carrier material, e.g. a membrane. The part of the lysate on the base of the vessel which has an increased content of cell debris is not transferred.

The vessel 160 containing carrier material is in a holding position 130 (or 150) of the vessel holder 120. By centrifuging, the lysate is forced through or along the carrier material, the biomolecules preferably remaining on the carrier material. The remaining lysate is rinsed into a waste volume 122 of the vessel holder 120 (see FIG. 11 c).

A washing step is then carried out: after the addition of one or more washing liquids to the vessel 160 using the pipette unit 500 the vessel 160 is centrifuged to force the washing liquid through or along the carrier material. This removes unwanted constituents from the carrier material. The washing liquid containing the dissolved ingredients is rinsed into the waste volume 122 of the vessel holder 120. Washing steps may optionally be repeated.

In order to prepare the elusion step the vessel 160 is transferred. Generally, and independently of the other protocol steps, the vessel 160 is transferred before the elusion step, using the gripper, into another vessel 170 for receiving biological material, particularly a liquid. Preferably, the vessel is transferred using a gripper 400. The gripper preferably has some of the features described in conjunction with FIGS. 6, 8 and/or 9. Particularly preferably, the additional vessel 170 is arranged in a centrifuge 200, and most preferably the additional vessel 170 is removably arranged in a holding position 140 of a vessel holder 120 in the centrifuge. It is also preferable that the vessel 160 should have an outlet opening for the escape of the liquid and that the vessel 160 after the transfer should be arranged relative to the additional vessel 170 such that during the centrifuging any liquid passing out through the outlet opening of the vessel 160 is collected in the additional vessel 170.

It is assumed hereinafter, in a nonrestrictive capacity, that the vessel 160 to be transferred is arranged in a first holding position 130 and that the additional vessel 170 is arranged in a second holding position 140 of a vessel holder 120 in the centrifuge (see FIG. 11c). Then, independently of the other steps of the protocol, a vessel transfer can be carried out by the gripper into another vessel, as follows, for example: the gripper unit 400 is positioned in relation to the vessel holder 120, the positioning element 452 interacting with the positioning counter-element 124 of the vessel holder, as illustrated in the description of FIGS. 8 and 9. If necessary the gripper 410 is pivoted about the axis 436a by the drive 431 so that the gripper can grip the vessel 160. It grips the vessel and removes it from the holding position 130. The gripper is pivoted about the axis 436a by the drive 431. Finally, the gripper places the vessel 160 in the additional vessel 170 and releases the vessel. Throughout the course of this movement it is preferable for the positioning element 452 to interact with the positioning counter-element 124 of the vessel holder. This can be ensured by means of the spring 458, for example.

Alternatively, the vessel 160 can also be transferred from a first holding position 130 of a first vessel holder 120 into a further vessel 170, the further vessel being arranged in another vessel holder in the centrifuge which is different from the first vessel holder 120. Then, between the removal and the insertion, a further step of positioning the gripper unit in relation to the further vessel holder has to take place.

Further details of the gripper 410 and the movements mentioned above are described above in connection with FIGS. 8 and 9.

For the elusion step eluting fluid is added to the vessel 160 (pipetted in), and the vessel 160 is centrifuged. The eluting fluid dissolves the desired ingredient out of the carrier material and washes it into the additional vessel. There the desired ingredient is held in readiness, dissolved in the eluting liquid.

Finally, for a last step of "clearing", vessels which have been used for intermediate steps of the procedure are disposed of manually or automatically, for example by being taken to the waste disposal station 740.

The invention claimed is:

1. An apparatus for processing biological material, comprising:
   a centrifuge having a rotatable centrifuge rotor with at least one vessel holder comprising a holding member for holding a vessel for biological material, at least one lid receptor for holding a lid attached to the vessel, and a positioning counter-element shaped for engaging with a positioning element, and
   a gripper with a lid holder attached thereto, wherein the gripper is capable of being used for transferring a vessel from a first holding position of the vessel holder to a second holding position of the vessel holder,
wherein the at least one lid receptor is shaped to allow access to the lid by the lid holder, wherein the access to the lid of the lid holder comprises mechanical contacting of the lid by the lid holder, wherein the lid receptor has an opening which allows access by the lid holder to the lid, wherein the lid receptor is constructed so as to fix the lid in a secure position during centrifuging, and wherein the lid holder is adapted to make contact with the lid through the opening and provide a stop for it, so that during removal of the vessel from the vessel holder or during insertion of the vessel therein the lid can be removed from the lid receptor or placed therein while retaining the position defined by the lid holder.

2. The apparatus for processing biological material according to claim 1, wherein the gripper further comprises a positioning element for positioning an angular position or a deflection angle of the vessel holder by interaction with the positioning counter-element.

3. An apparatus for processing biological material according to claim 2, wherein the centrifuge rotor is rotatable about a rotor axis, said apparatus further comprising a drive for the centrifuge rotor,
wherein the positioning element is not co-rotatable with the rotor, and
wherein the positioning counter-element is co-rotatable with the rotor.

4. An apparatus for processing biological material according to claim 2, further comprising a suspension means which can be suspended in the centrifuge rotor and into which the vessel holder is insertable,
wherein the suspension means comprises a first stop for the pivoting movement of the vessel holder insertable thereinto,
wherein the positioning element is suitable for securing the vessel holder at a deflection angle at the stop by interaction with the positioning counter-element of the vessel holder,
wherein the centrifuge rotor is rotatable about a rotor axis, which is suitable for the pivotal mounting of the vessel holder.

5. An apparatus for processing biological material of claim 1, further comprising a vessel,
wherein the vessel comprises at least one vessel part of increased recognisability, and wherein said apparatus comprises
a radiation source for irradiating a registration area in the vessel holder, wherein the registration area is associated with the vessel part of increased recognisability;
a sensor for measuring the intensity of radiation coming from the registration area;
an evaluating unit which is equipped to register the presence or absence of the vessel by running a comparison between the intensity measured and a defined threshold.

6. The apparatus according to claim 5, wherein the sensor is movable.

7. An apparatus for processing biological material according to claim 1, further comprising:
a sensor unit with an ultrasound source and an ultrasound sensor; and
an evaluating unit for determining, as a function of sensor data of the ultrasound sensor, the state of opening of the vessel, and for determining, as a function of sensor data of the ultrasound sensor and with the vessel open, the presence of a substance in the vessel.

8. The apparatus according to claim 7, wherein the sensor unit is movable and further comprises:
a radiation sensor, and
a positioner for positioning the sensor unit in relation to the vessel as a function of sensor data of the radiation sensor.

9. An apparatus for processing biological material according to claim 1, further comprising
a container station for keeping a supply of vessels;
a marking on the container station, which contains information as to the nature of the vessels; and
a radiation sensor for reading the marking.

10. The apparatus according to claim 9, further comprising a radiation source for irradiating the marking.

* * * * *